United States Patent
Presz, Jr. et al.

(10) Patent No.: US 10,106,770 B2
(45) Date of Patent: *Oct. 23, 2018

(54) METHODS AND APPARATUS FOR PARTICLE AGGREGATION USING ACOUSTIC STANDING WAVES

(71) Applicant: FloDesign Sonics, Inc., Wilbraham, MA (US)

(72) Inventors: Walter M. Presz, Jr., Wilbraham, MA (US); Kedar Chitale, West Hartford, CT (US); Bart Lipkens, Hampden, MA (US)

(73) Assignee: FloDesign Sonics, Inc., Wilbraham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/397,326

(22) Filed: Jan. 3, 2017

(65) Prior Publication Data
US 2017/0166860 A1    Jun. 15, 2017

Related U.S. Application Data

(63) Continuation-in-part of application No. 15/080,354, filed on Mar. 24, 2016, now Pat. No. 9,533,241.
(Continued)

(51) Int. Cl.
*C02F 1/36* (2006.01)
*C12M 1/00* (2006.01)
(Continued)

(52) U.S. Cl.
CPC .............. *C12M 47/02* (2013.01); *B01D 15/08* (2013.01); *B01D 21/283* (2013.01); *B01D 21/34* (2013.01);
(Continued)

(58) Field of Classification Search
CPC ...... B01D 29/115; B01D 37/00; B01D 29/52; B01D 2201/0446; B01D 2201/127; B01D 29/865; B01D 2201/0415
See application file for complete search history.

(56) References Cited

U.S. PATENT DOCUMENTS

| 2,473,971 A | 6/1949 | Ross |
| 2,667,944 A | 2/1954 | Crites |

(Continued)

FOREIGN PATENT DOCUMENTS

| DE | 30 27 433 A1 | 2/1982 |
| DE | 32 18 488 A1 | 11/1983 |

(Continued)

OTHER PUBLICATIONS

Alvarez et al.; Shock Waves, vol. 17, No. 6, pp. 441-447, 2008.
(Continued)

*Primary Examiner* — Walter Dean Griffin
*Assistant Examiner* — Cameron J Allen
(74) *Attorney, Agent, or Firm* — Rick Klein, Esq.; Fay Sharpe, LLP

(57) ABSTRACT

Methods for generating particulate clusters and nodal trapping lines having desired widths are disclosed. The devices include an acoustic chamber having an inlet and an outlet. An ultrasonic transducer and reflector create a multi-dimensional acoustic standing wave that generates particulate clusters separated by a channel of fluid running therebetween and creates nodal trapping lines. The frequency of the multi-dimensional acoustic standing wave can be selectively tuned so as to selectively control at least one of (a) a width of each particulate cluster, or (b) a width of each channel of fluid. The frequency of the multi-dimensional acoustic standing wave can also be selectively tuned so as to selectively control the width of each nodal trapping line. Also
(Continued)

disclosed are particulate clusters separated by a channel of fluid, wherein a ratio of the widths of the particulate clusters and the channel of fluid can be varied as desired.

12 Claims, 34 Drawing Sheets

Related U.S. Application Data

(60) Provisional application No. 62/162,831, filed on May 18, 2015, provisional application No. 62/137,795, filed on Mar. 24, 2015.

(51) Int. Cl.
    *C02F 1/00*     (2006.01)
    *B01D 21/28*     (2006.01)
    *B01D 21/34*     (2006.01)
    *B01D 15/08*     (2006.01)
    *C12N 13/00*     (2006.01)
    *B06B 1/06*     (2006.01)
    *C12M 1/42*     (2006.01)
    *C02F 101/32*     (2006.01)

(52) U.S. Cl.
    CPC ............... *B06B 1/06* (2013.01); *C02F 1/008* (2013.01); *C02F 1/36* (2013.01); *C12M 29/04* (2013.01); *C12M 35/04* (2013.01); *C12N 13/00* (2013.01); *C02F 2101/32* (2013.01)

(56) References Cited

U.S. PATENT DOCUMENTS

| | | | |
|---|---|---|---|
| 3,372,370 A | 3/1968 | Cyr |
| 3,555,311 A | 1/1971 | Weber |
| 4,055,491 A | 10/1977 | Porath-Furedi |
| 4,065,875 A | 1/1978 | Srna |
| 4,118,649 A | 10/1978 | Schwartzman et al. |
| 4,158,629 A | 6/1979 | Sawyer |
| 4,165,273 A | 8/1979 | Azarov et al. |
| 4,173,725 A | 11/1979 | Asai et al. |
| 4,204,096 A | 5/1980 | Barcus et al. |
| 4,254,661 A | 3/1981 | Kossoff et al. |
| 4,320,659 A | 3/1982 | Lynnworth et al. |
| 4,344,448 A | 8/1982 | Potts |
| 4,398,325 A | 8/1983 | Piaget et al. |
| 4,552,669 A | 11/1985 | Sekellick |
| 4,666,595 A | 5/1987 | Graham |
| 4,673,512 A | 6/1987 | Schram |
| 4,699,588 A | 10/1987 | Zinn et al. |
| 4,743,361 A | 5/1988 | Schram |
| 4,759,775 A | 7/1988 | Peterson et al. |
| 4,800,316 A | 1/1989 | Wang |
| 4,821,838 A | 4/1989 | Chen |
| 4,836,684 A | 6/1989 | Javorik et al. |
| 4,860,993 A | 8/1989 | Goode |
| 4,878,210 A | 10/1989 | Mitome |
| 4,983,189 A | 1/1991 | Peterson et al. |
| 5,059,811 A | 10/1991 | King et al. |
| 5,062,965 A | 11/1991 | Bernou et al. |
| 5,085,783 A | 2/1992 | Feke et al. |
| 5,164,094 A | 11/1992 | Stuckart |
| 5,225,089 A | 7/1993 | Benes et al. |
| 5,371,729 A | 12/1994 | Manna |
| 5,395,592 A | 3/1995 | Bolleman et al. |
| 5,431,817 A | 7/1995 | Braatz et al. |
| 5,443,985 A | 8/1995 | Lu et al. |
| 5,452,267 A | 9/1995 | Spevak |
| 5,475,486 A | 12/1995 | Paoli |
| 5,484,537 A | 1/1996 | Whitworth |
| 5,527,460 A | 6/1996 | Trampler et al. |
| 5,560,362 A | 10/1996 | Sliwa, Jr. et al. |
| 5,594,165 A | 1/1997 | Madanshetty |
| 5,604,301 A | 2/1997 | Mountford et al. |
| 5,626,767 A | 5/1997 | Trampler et al. |
| 5,688,405 A | 11/1997 | Dickinson et al. |
| 5,711,888 A | 1/1998 | Trampler et al. |
| 5,831,166 A | 11/1998 | Kozuka et al. |
| 5,834,871 A | 11/1998 | Puskas |
| 5,902,489 A | 5/1999 | Yasuda et al. |
| 5,912,182 A | 6/1999 | Coakley et al. |
| 5,947,299 A | 9/1999 | Vazquez et al. |
| 5,951,456 A | 9/1999 | Scott |
| 6,090,295 A | 6/2000 | Raghavarao et al. |
| 6,166,231 A | 12/2000 | Hoeksema |
| 6,216,538 B1 | 4/2001 | Yasuda et al. |
| 6,205,848 B1 | 6/2001 | Faber et al. |
| 6,273,262 B1 | 8/2001 | Yasuda et al. |
| 6,332,541 B1 | 12/2001 | Coakley et al. |
| 6,391,653 B1 | 5/2002 | Letcher et al. |
| 6,475,151 B2 | 11/2002 | Koger et al. |
| 6,482,327 B1 | 11/2002 | Mori et al. |
| 6,487,095 B1 | 11/2002 | Malik et al. |
| 6,592,821 B1 | 7/2003 | Wada et al. |
| 6,641,708 B1 | 11/2003 | Becker et al. |
| 6,649,069 B2 | 11/2003 | DeAngelis |
| 6,699,711 B1 | 3/2004 | Hahn et al. |
| 6,727,451 B1 | 4/2004 | Fuhr et al. |
| 6,763,722 B2 | 7/2004 | Fjield et al. |
| 6,881,314 B1 | 4/2005 | Wang et al. |
| 6,929,750 B2 | 8/2005 | Laurell et al. |
| 6,936,151 B1 | 8/2005 | Lock et al. |
| 7,008,540 B1 | 3/2006 | Weavers et al. |
| 7,010,979 B2 | 3/2006 | Scott |
| 7,061,163 B2 | 6/2006 | Nagahara et al. |
| 7,081,192 B1 | 7/2006 | Wang et al. |
| 7,093,482 B2 | 8/2006 | Berndt |
| 7,108,137 B2 | 9/2006 | Lal et al. |
| 7,150,779 B2 | 12/2006 | Meegan, Jr. |
| 7,186,502 B2 | 3/2007 | Vesey |
| 7,191,787 B1 | 3/2007 | Redeker et al. |
| 7,322,431 B2 | 1/2008 | Ratcliff |
| 7,331,233 B2 | 2/2008 | Scott |
| 7,340,957 B2 | 3/2008 | Kaduchak et al. |
| 7,373,805 B2 | 5/2008 | Hawkes et al. |
| 7,541,166 B2 | 6/2009 | Belgrader et al. |
| 7,601,267 B2 | 10/2009 | Haake et al. |
| 7,673,516 B2 | 3/2010 | Janssen et al. |
| 7,837,040 B2 | 11/2010 | Ward et al. |
| 7,846,382 B2 | 12/2010 | Strand et al. |
| 7,968,049 B2 | 6/2011 | Takahashi et al. |
| 8,075,786 B2 | 12/2011 | Bagajewicz |
| 8,080,202 B2 | 12/2011 | Takahashi et al. |
| 8,134,705 B2 | 3/2012 | Kaduchak et al. |
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,592,204 B2 | 11/2013 | Lipkens et al. |
| 8,679,338 B2 | 3/2014 | Rietnnan et al. |
| 8,691,145 B2 | 4/2014 | Dionne et al. |
| 8,873,051 B2 | 10/2014 | Kaduchak et al. |
| 8,889,388 B2 | 11/2014 | Wang et al. |
| 9,272,234 B2 | 3/2016 | Lipkens et al. |
| 9,357,293 B2 | 5/2016 | Claussen |
| 9,365,815 B2 | 6/2016 | Miyazaki et al. |
| 9,368,110 B1 | 6/2016 | Hershey et al. |
| 9,388,363 B2 | 7/2016 | Goodson et al. |
| 9,391,542 B2 | 7/2016 | Wischnewskiy |
| 9,403,114 B2 | 8/2016 | Kusuura |
| 9,410,256 B2 | 8/2016 | Dionne et al. |
| 9,416,344 B2 | 8/2016 | Lipkens et al. |
| 9,421,553 B2 | 8/2016 | Dionne et al. |
| 9,422,328 B2 | 8/2016 | Kennedy, III et al. |
| 9,457,139 B2 | 10/2016 | Ward et al. |
| 9,457,302 B2 | 10/2016 | Lipkens et al. |
| 9,458,450 B2 | 10/2016 | Lipkens et al. |
| 9,464,303 B2 | 10/2016 | Burke |

(56) References Cited

U.S. PATENT DOCUMENTS

| | | |
|---|---|---|
| 9,476,385 B2 | 10/2016 | Ward et al. |
| 9,480,375 B2 | 11/2016 | Marshall et al. |
| 9,480,935 B2 | 11/2016 | Mariella, Jr. et al. |
| 9,488,621 B2 | 11/2016 | Kaduchak et al. |
| 9,504,780 B2 | 11/2016 | Spain et al. |
| 9,512,395 B2 | 12/2016 | Lipkens et al. |
| 9,513,205 B2 | 12/2016 | Yu et al. |
| 9,514,924 B2 | 12/2016 | Morris et al. |
| 9,517,474 B2 | 12/2016 | Mao et al. |
| 2002/0038662 A1 | 4/2002 | Schuler et al. |
| 2002/0134734 A1 | 9/2002 | Campbell et al. |
| 2003/0015035 A1 | 1/2003 | Kaduchak et al. |
| 2003/0028108 A1 | 2/2003 | Miller et al. |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2004/0035208 A1 | 2/2004 | Diaz et al. |
| 2004/0112841 A1 | 6/2004 | Scott |
| 2004/0124155 A1 | 7/2004 | Meegan, Jr. |
| 2004/0149039 A1 | 8/2004 | Cardelius |
| 2005/0031499 A1 | 2/2005 | Meier |
| 2005/0121269 A1 | 6/2005 | Namduri |
| 2005/0145567 A1 | 7/2005 | Quintel et al. |
| 2005/0196725 A1 | 9/2005 | Fu |
| 2006/0037915 A1 | 2/2006 | Strand et al. |
| 2006/0037916 A1 | 2/2006 | Trampler |
| 2006/0050615 A1 | 3/2006 | Swisher |
| 2007/0053795 A1 | 3/2007 | Laugharn, Jr. et al. |
| 2007/0224676 A1 | 9/2007 | Haq |
| 2007/0267351 A1 | 11/2007 | Roach et al. |
| 2007/0272618 A1 | 11/2007 | Gou et al. |
| 2007/0284299 A1 | 12/2007 | Xu et al. |
| 2008/0011693 A1 | 1/2008 | Li et al. |
| 2008/0067128 A1 | 3/2008 | Hoyos et al. |
| 2008/0105625 A1 | 5/2008 | Rosenberg et al. |
| 2008/0181838 A1 | 7/2008 | Kluck |
| 2008/0217259 A1 | 9/2008 | Siversson |
| 2008/0245709 A1 | 10/2008 | Kaduchak et al. |
| 2008/0245745 A1 | 10/2008 | Ward et al. |
| 2008/0264716 A1 | 10/2008 | Kuiper et al. |
| 2008/0272034 A1 | 11/2008 | Ferren et al. |
| 2008/0272065 A1 | 11/2008 | Johnson |
| 2008/0316866 A1 | 12/2008 | Goodemote et al. |
| 2009/0029870 A1 | 1/2009 | Ward et al. |
| 2009/0053686 A1 | 2/2009 | Ward et al. |
| 2009/0087492 A1 | 4/2009 | Johnson et al. |
| 2009/0098027 A1 | 4/2009 | Tabata et al. |
| 2009/0104594 A1 | 4/2009 | Webb |
| 2009/0126481 A1 | 5/2009 | Burris |
| 2009/0178716 A1 | 7/2009 | Kaduchak et al. |
| 2009/0194420 A1 | 8/2009 | Mariella, Jr. et al. |
| 2009/0227042 A1 | 9/2009 | Gauer et al. |
| 2009/0045107 A1 | 12/2009 | Ward et al. |
| 2009/0295505 A1 | 12/2009 | Mohammadi et al. |
| 2010/0000945 A1 | 1/2010 | Gavalas |
| 2010/0078323 A1 | 4/2010 | Takahashi et al. |
| 2010/0078384 A1 | 4/2010 | Yang |
| 2010/0124142 A1 | 5/2010 | Laugham et al. |
| 2010/0139377 A1 | 6/2010 | Huang et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0092726 A1 | 4/2011 | Clarke |
| 2011/0095225 A1 | 4/2011 | Eckelberry et al. |
| 2011/0123392 A1 | 5/2011 | Dionne et al. |
| 2011/0125024 A1 | 5/2011 | Mueller |
| 2011/0146678 A1 | 6/2011 | Ruecroft et al. |
| 2011/0154890 A1 | 6/2011 | Holm et al. |
| 2011/0166551 A1 | 7/2011 | Schafer |
| 2011/0189732 A1 | 8/2011 | Weinand et al. |
| 2011/0245750 A1 | 10/2011 | Lynch et al. |
| 2011/0262990 A1 | 10/2011 | Wang et al. |
| 2011/0278218 A1 | 11/2011 | Dionne et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0145633 A1 | 6/2012 | Polizzotti et al. |
| 2012/0163126 A1 | 6/2012 | Campbell et al. |
| 2012/0175012 A1 | 7/2012 | Goodwin et al. |
| 2012/0231504 A1 | 9/2012 | Niazi |
| 2012/0267288 A1 | 10/2012 | Chen et al. |
| 2012/0325727 A1 | 12/2012 | Dionne et al. |
| 2012/0325747 A1 | 12/2012 | Reitman et al. |
| 2012/0328477 A1 | 12/2012 | Dionne et al. |
| 2012/0329122 A1 | 12/2012 | Lipkens et al. |
| 2013/0017577 A1 | 1/2013 | Arunakumari et al. |
| 2013/0115664 A1 | 5/2013 | Khanna et al. |
| 2013/0175226 A1 | 7/2013 | Coussios et al. |
| 2013/0217113 A1 | 8/2013 | Srinivasan et al. |
| 2013/0277316 A1 | 10/2013 | Dutra et al. |
| 2013/0277317 A1 | 10/2013 | LoRicco et al. |
| 2013/0284271 A1 | 10/2013 | Lipkens et al. |
| 2014/0011240 A1 | 1/2014 | Lipkens et al. |
| 2014/0017758 A1 | 1/2014 | Kniep et al. |
| 2014/0102947 A1 | 4/2014 | Baym et al. |
| 2014/0141413 A1 | 5/2014 | Laugham, Jr. et al. |
| 2014/0319077 A1 | 10/2014 | Lipkens et al. |
| 2014/0377834 A1 | 12/2014 | Presz, Jr. et al. |
| 2015/0053561 A1 | 2/2015 | Ward et al. |
| 2015/0060581 A1 | 3/2015 | Santos et al. |
| 2015/0274550 A1 | 10/2015 | Lipkens et al. |
| 2015/0321129 A1 | 11/2015 | Lipkens et al. |
| 2016/0121331 A1 | 5/2016 | Kapur et al. |
| 2016/0123858 A1 | 5/2016 | Kapur et al. |
| 2016/0145563 A1 | 5/2016 | Berteau et al. |
| 2016/0153249 A1 | 6/2016 | Mitri |
| 2016/0175198 A1 | 6/2016 | Warner et al. |
| 2016/0184790 A1 | 6/2016 | Sinha et al. |
| 2016/0202237 A1 | 7/2016 | Zeng et al. |
| 2016/0208213 A1 | 7/2016 | Doyle et al. |
| 2016/0230168 A1 | 8/2016 | Kaduchak et al. |
| 2016/0237110 A1 | 8/2016 | Gilmanshin et al. |
| 2016/0237394 A1 | 8/2016 | Lipkens et al. |
| 2016/0237395 A1 | 8/2016 | Lipkens et al. |
| 2016/0252445 A1 | 9/2016 | Yu et al. |
| 2016/0279540 A1 | 9/2016 | Presz, Jr. et al. |
| 2016/0279551 A1 | 9/2016 | Foucault |
| 2016/0312168 A1 | 10/2016 | Pizzi |
| 2016/0314868 A1 | 10/2016 | El-Zahab et al. |
| 2016/0319270 A1 | 11/2016 | Lipkens et al. |
| 2016/0325206 A1 | 11/2016 | Presz, Jr. et al. |
| 2016/0332159 A1 | 11/2016 | Dual et al. |
| 2016/0339360 A1 | 11/2016 | Lipkens et al. |
| 2016/0347628 A1 | 12/2016 | Dionne et al. |
| 2016/0355776 A1 | 12/2016 | Lipkens et al. |
| 2016/0361670 A1 | 12/2016 | Lipkens et al. |
| 2016/0363579 A1 | 12/2016 | Lipkens et al. |
| 2017/0049949 A1* | 2/2017 | Gilmanshin ........ A61M 1/3678 |

FOREIGN PATENT DOCUMENTS

| | | |
|---|---|---|
| DE | 196 48 519 A1 | 6/1998 |
| DE | 103 19 467 B3 | 7/2004 |
| DE | 10 2008 006 501 A1 | 9/2008 |
| EP | 0 292 470 B1 | 11/1988 |
| EP | 0 641 606 | 3/1995 |
| EP | 1 175 931 A1 | 1/2002 |
| EP | 1 254 669 B1 | 11/2002 |
| GB | 2 420 510 A | 5/2006 |
| JP | 9-136090 | 5/1997 |
| RU | 2085933 | 7/1997 |
| SU | 629496 | 10/1978 |
| WO | WO 1987/07178 A1 | 12/1987 |
| WO | WO 89/11899 A1 | 12/1989 |
| WO | WO 90/05008 | 3/1990 |
| WO | WO 97/34643 | 9/1997 |

(56) References Cited

FOREIGN PATENT DOCUMENTS

| | | |
|---|---|---|
| WO | WO 1998/017373 | 4/1998 |
| WO | WO 98/50133 A1 | 11/1998 |
| WO | WO 02/072234 A1 | 9/2002 |
| WO | WO 03/089567 | 10/2003 |
| WO | WO 2004/079716 A1 | 9/2004 |
| WO | WO 2009/063198 | 5/2009 |
| WO | WO 2009/111276 A1 | 9/2009 |
| WO | WO 2009/144709 A1 | 12/2009 |
| WO | WO 2010/024753 A1 | 4/2010 |
| WO | WO 2010/040394 A1 | 4/2010 |
| WO | WO 2011/023949 A2 | 3/2011 |
| WO | WO 2011/025890 A1 | 3/2011 |
| WO | WO 2011/027146 A2 | 3/2011 |
| WO | WO 2011/131947 A2 | 10/2011 |
| WO | WO 2011/161463 A2 | 12/2011 |
| WO | WO 2013/043297 A1 | 3/2013 |
| WO | WO 2013/055517 A1 | 4/2013 |
| WO | WO 2013/138797 A1 | 9/2013 |
| WO | WO 2013/148376 | 10/2013 |
| WO | WO 2013/159014 A1 | 10/2013 |
| WO | WO 2014/014941 A1 | 1/2014 |
| WO | WO 2014/029505 | 2/2014 |
| WO | WO 2014/055219 A2 | 4/2014 |
| WO | WO 2014/124306 A1 | 8/2014 |
| WO | WO 2014/153651 | 10/2014 |
| WO | WO 2015/006730 | 1/2015 |

OTHER PUBLICATIONS

Benes et al.; Ultrasonic Separation of Suspended Particles, 2001 IEEE Ultrasonics Symposium; Oct. 7-10, 2001; pp. 649-659; Atlanta, Georgia.

Castilho et al.; Animal Cell Technology: From Biopharmaceuticals to Gene Therapy; 11—Animal Cell Separation; 2008.

Castro; Tunable gap and quantum quench dynamics in bilayer graphene; Jul. 13, 2010; Mathematica Summer School.

Cravotto et al.; Ultrasonics Sonochemistry, vol. 15, No. 5, pp. 898-902, 2008.

Garcia-Lopez, et al; Enhanced Acoustic Separation of Oil-Water Emulsion in Resonant Cavities. The Open Acoustics Journal. 2008, vol. 1, pp. 66-71.

Hill et al.; Ultrasonic Particle Manipulation; Microfluidic Technologies for Miniaturized Analysis Systems, Jan. 2007, pp. 359-378.

Ilinskii et al.; Acoustic Radiation Force on a Sphere in Tissue; AIP Conference Proceedings; 2012.

Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.

Latt et al.; Ultrasound-membrane hybrid processes for enhancement of filtration properties; Ultrasonics sonochemistry 13.4 (2006): 321-328.

Li et al.; Electromechanical behavior of PZT-brass unimorphs; J. Am. Ceram. Soc. vol. 82; No. 7; pp. 1733-1740, 1999.

Lipkens et al.; Frequency sweeping and fluid flow effects on particle trajectories in ultrasonic standing waves; Acoustics 08, Paris, Jun. 29-Jul. 4, 2008.

Lipkens et al.; Prediction and measurement of particle velocities in ultrasonic standing waves; J. Acoust. Soc. Am., 124 No. 4, pp. 2492 (A) 2008.

Lipkens et al.; Separation of micron-sized particles in macro-scale cavities by ultrasonic standing waves; Presented at the International Congress on Ultrasonics, Santiago; Jan. 11-17, 2009.

Lipkens et al.; The effect of frequency sweeping and fluid flow on particle trajectories in ultrasonic standing waves; IEEE Sensors Journal; vol. 8, No. 6, pp. 667-677, 2008.

Lipkens et al.; Separation of bacterial spores from flowering water in macro-scale cavities by ultrasonic standing waves; submitted/uploaded to http://arxiv.org/abs/1006.5467 on Jun. 28, 2010.

Lipkens et al., Macro-scale acoustophoretic separation of lipid particles from red blood cells, The Journal of the Acoustical Society of America, vol. 133, Jun. 2, 2013, p. 045017, XP055162509, New York, NY.

Meribout et a.; An Industrial-Prototype Acoustic Array for Real-Time Emulsion Layer Detection in Oil Storage Tanks; IEEE Sensors Journal, vol. 9, No. 12, Dec. 2009.

Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.

Pangu et al.; Droplet transport and coalescence kinetics in emulsions subjected to acoustic fields; Ultrasonics 46, pp. 289-302 (2007).

Ponomarenko et al.; Density of states and zero Landau level probed through capacitance of graphene; Nature Nanotechnology Letters, Jul. 5, 2009; DOI: 10.1038/NNANO.2009.177.

Ryll et al.; Performance of Small-Scale CHO Perfusion Cultures Using an Acoustic Cell Filtration Device for Cell Retention: Characterization of Separation Efficiency and Impact of Perfusion on Product Quality; Biotechnology and Bioengineering; vol. 69; Iss. 4; pp. 440-449; Aug. 2000.

Seymour et al, J. Chem. Edu., 1990, 67(9), p. 763, published Sep. 1990.

Volpin et al.; Mesh simplification with smooth surface reconstruction; Computer-Aided Design; vol. 30; No. 11; 1998.

Wang et al.; Retention and Viability Characteristics of Mammalian Cells in an Acoustically Driven Polymer Mesh; Biotechnol. Prog. 2004, pp. 384-387 (2004).

Wicklund et al.; Ultrasonic Manipulation of Single Cells; Methods in Molecular Biology; vol. 853; pp. 1777-196; 2012.

Annex to Form PCT/ISA/206—Communication Relating to the Results of the Partial International Search Report, dated Jul. 18, 2013.

European Search Report of European Application No. 11769474.5, dated Sep. 5, 2013.

European Search Report of European Application No. 13760840.2, dated Feb. 4, 2016.

European Search Report of European Application No. 13721179.3 dated Feb. 23, 2016.

International Search Report and Written Opinion dated Dec. 20, 2011, for corresponding PCT application No. PCT/US2011/032181.

International Search Report and Written Opinion dated Feb. 27, 2012, for PCT application No. PCT/US2011/040787.

International Search Report and Written Opinion of International Application No. PCT/US2012/051804 dated Nov. 16, 2012.

International Search Report and Written Opinion of International Application No. PCT/US2013/037404 dated Jun. 21, 2013.

International Search Report and Written Opinion of International Application No. PCT/US2013/032705 dated Jul. 26, 2013.

International Search Report and Written Opinion of International Application No. PCT/US2013/050729 dated Sep. 25, 2013.

International Search Report dated Feb. 18, 2014 in corresponding PCT Application No. PCT/US2013/059640.

International Search Report for corresponding PCT Application Serial No. PCT/US2014/015382 dated May 6, 2014.

International Search Report for PCT/US2014/035557 dated Aug. 27, 2014.

International Search Report for PCT/US2014/043930 dated Oct. 22, 2014.

International Search Report for PCT/US2014/046412 dated Oct. 27, 2014.

International Search Report for PCT/US2014/064088 dated Jan. 30, 2015.

Extended European Search Report for Application No. EP 12833859.7 dated Mar. 20, 2015.

International Search Report and Written Opinion for International Application No. PCT/US2015/010595 dated Apr. 15, 2015.

International Search Report for PCT/US2015/019755 dated May 4, 2015.

International Search Report dated Jul. 30, 2015 for International Application No. PCT/US2015/030009.

(56) References Cited

OTHER PUBLICATIONS

International Search Report for PCT/US2015/039125 dated Sep. 30, 2015.
International Search Report and Written Opinion for PCT Application Serial No. PCT/US2015/053200 dated Dec. 28, 2015.
European Search Report of European Application No. 11796470.0 dated Jan. 5, 2016.
International Search Report and Written Opinion for International Application No. PCT/US2015/066884, dated Mar. 22, 2016.
International Search Report and Written Opinion for International Application No. PCT/US2016/024082 dated Jun. 27, 2016.
International Search Report and Written Opinion for International Application No. PCT/US2016/044586 dated Oct. 21, 2016.
International Search Report and Written Opinion for International Application No. PCT/US2016/031357 dated Jul. 26, 2016.
International Search Report and Written Opinion for International Application No. PCT/US2015/024365 dated Oct. 13, 2016.
International Search Report and Written Opinion for International Application No. PCT/US2016/041664 dated Oct. 18, 2016.
International Search Report and Written Opinion for International Application No. PCT/US2016/049088 dated Nov. 28, 2016.
International Search Report and Written Opinion for International Application No. PCT/US2016/050415 dated Nov. 28, 2016.
International Search Report and Written Opinion for International Application No. PCT/US2016/037104 dated Dec. 16, 2016.
Phys. Org. "Engineers develop revolutionary nanotech water desalination membrane." Nov. 6, 2006. http://phys.org/news82047372.html.
"Proceedings of the Acoustics 2012 Nantes Conference," Apr. 23-27, 2012, Nantes, France, pp. 278-282.
Sony New Release: <http://www.sony.net/SonyInfo/News/Press/201010/10-137E/index.html>.
Chitale et al.; Understanding the Fluid Dynamics Associated with Macro Scale Ultrasonic Separators; Proceedings of Meetings on Acoustics, May 2015.
Musiak et al.; Design of a Control System for Acoustophoretic Separation, 2013 IEEE 56$^{th}$ International Midwest Symposium on Circuits and Systems (MWSCAS), Aug. 2013, pp. 1120-1123.
International Search Report and Written Opinion for International Application No. PCT/US2017/017788 dated May 8, 2017.

\* cited by examiner

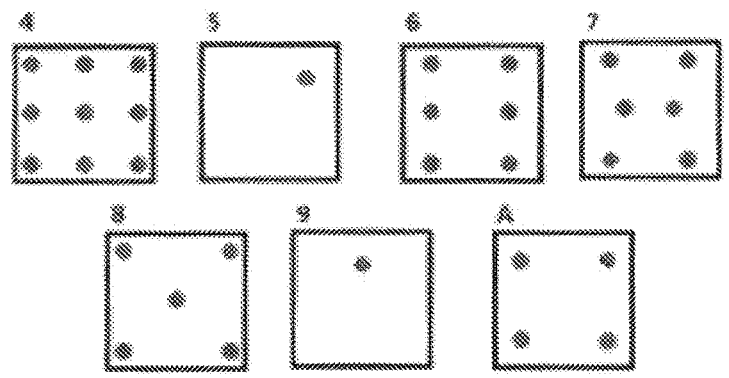
Figure 14A
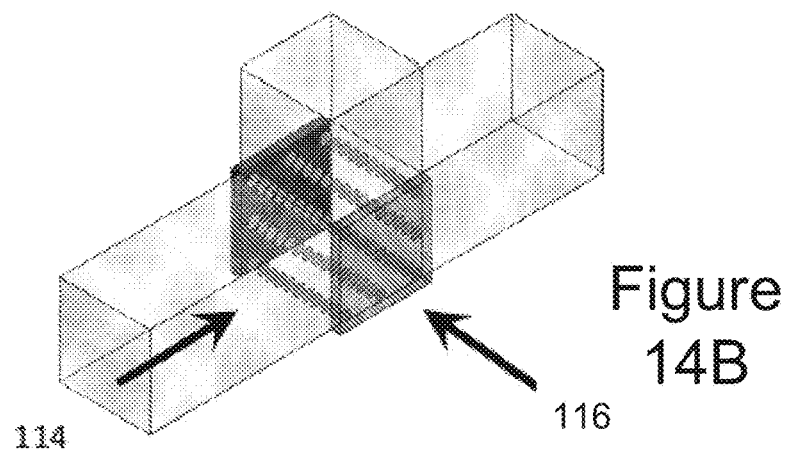
Figure 14B
114     116
Figure 14C
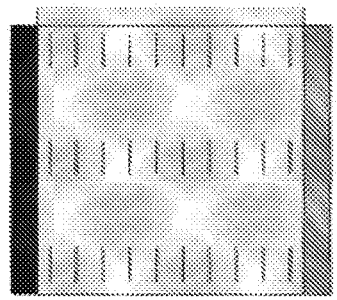
Figure 14D
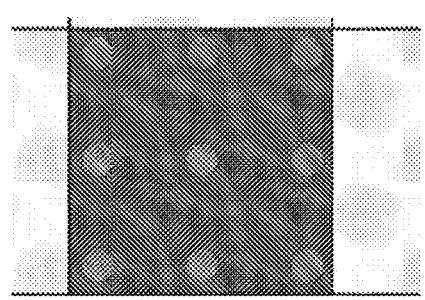

$$F_{DF} = F_{DG}$$

$$F_{DF} = C_D \frac{1}{2}\rho V_D^2 HD$$

$$F_{DG} = \frac{\varphi}{2}(\rho_P - \rho_F)g\frac{\pi D^2}{4}H$$

$$C_D \frac{1}{2}\rho V_D^2 HD = \frac{\varphi}{2}(\rho_P - \rho_F)g\frac{\pi D^2}{4}H$$

$$C_D V_D^2 = \varphi\left(\frac{\rho_P}{\rho_F} - 1\right)g\frac{\pi D}{4}$$

METHODS AND APPARATUS FOR PARTICLE AGGREGATION USING ACOUSTIC STANDING WAVES

CROSS-REFERENCE TO RELATED APPLICATIONS

This application is a continuation-in-part of U.S. patent application Ser. No. 15/080,354, filed on Mar. 24, 2016, now U.S. Pat. No. 9,533,241, which claims priority to U.S. Provisional Patent Application Ser. No. 62/162,831, filed on May 18, 2015, and to U.S. Provisional Patent Application Ser. No. 62/137,795, filed on Mar. 24, 2015, the disclosures of which are hereby fully incorporated by reference in their entireties.

BACKGROUND

When particles are entrained or dispersed in a flowing fluid, aggregation and/or agglomeration of the particles to form larger clumps is typically due to some attraction or adhesion between the particles or the addition of a flocculating agent that aids in attracting and aggregating the particles. Attractive forces between the particles may be ionic or physical entanglement. Some flocculating agents, such as chitosan, may also be directly attractive to the particles and thus form clumps of particles in the fluid medium.

Typically, after the clumps of particles are formed in the fluid medium, a physical filtration process is utilized to separate the aggregated, agglomerated, flocculated or otherwise process-formed particle clumps from the fluid. In a filter separation process, the physical filter media and the clumps of particles that have been separated from the fluid media are typically discarded, thus creating additional waste and increasing costs. Also, with the use of this physical filtration process, the yield of the filtrate is lessened, as some of it is used to saturate the filtering material. Further, as the filter fills up, filtration capacity is reduced, and the process is stopped to remove and replace the filter or otherwise remove the particles trapped thereon.

An example of this type of filtration is the filtering of a bioreactor to separate the cells and cell debris from the expressed products of the cells, such as monoclonal antibodies and recombinant proteins. In some applications, the filter process entails the use of a diatomaceous earth (DE) filter. The DE filters become filled quickly with the cellular waste from the bioreactor during the filtration process. This decreases the flux rate, the ability of the filter to trap materials and allow the fluid to pass through the filter, and increases the pressure differential between the material to be filtered and the post-filter material. As a result, some of the product from the bioreactor (monoclonal antibodies and recombinant proteins) is lost, thus decreasing the yield of the bioreactor. Also, any high pressure differential generated by the filter blockage can generate product damage.

Thus, methods are sought where continuous filtration may be carried out with little or no loss of the expressed monoclonal antibodies and recombinant proteins while separating most or all of the cells and cell debris that are in the bioreactor fluid. Such continuous methods would also be useful in other filtration applications such as the filtering of oil from water, components from blood, tailings from water in tailing ponds, and, generally, particles from a fluid stream and immiscible or emulsified fluids from a fluid stream.

Acoustophoresis is the separation of particles and secondary fluids from a primary or host fluid using acoustics, such as acoustic standing waves. It has been known that acoustic standing waves can exert forces on particles in a fluid when there is a differential in both density and/or compressibility, otherwise known as the acoustic contrast factor. The pressure profile in a standing wave contains areas of local minimum pressure amplitudes at standing wave nodes and local maxima at standing wave anti-nodes. Depending on their density and compressibility, the particles can be trapped at the nodes or anti-nodes of the standing wave. Generally, the higher the frequency of the standing wave, the smaller the particles that can be trapped.

At the MEMS (micro-electromechanical systems) scale, conventional acoustophoresis systems tend to use half or quarter wavelength acoustic chambers, which at frequencies of a few megahertz are typically less than a millimeter in thickness, and operate at very slow flow rates (e.g., µL/min). Such systems are not scalable since they benefit from extremely low Reynolds number, laminar flow operation, and minimal fluid dynamic optimization.

At the macro-scale, planar acoustic standing waves have been used in separation processes. However, a single planar wave tends to trap the particles or secondary fluid such that separation from the primary fluid is achieved by turning off the planar standing wave. The removal of the planar standing wave may hinder continuous operation. Also, the amount of power that is used to generate the acoustic planar standing wave tends to heat the primary fluid through waste energy, which may be disadvantageous for the material being processed.

Conventional acoustophoresis devices have thus had limited efficacy due to several factors including heat generation, use of planar standing waves, limits on fluid flow, and the inability to capture different types of materials. It would therefore be desirable to provide systems and methods for generating optimized particle clusters to improve gravity separation and collection efficiency. Improved acoustophoresis devices using improved fluid dynamics would also be desirable, as would making the acoustophoresis process continuous.

BRIEF DESCRIPTION

The present disclosure relates, in various embodiments, to acoustophoretic systems and methods with improved fluid dynamics that can be used to improve the separation of particles from a particle/fluid mixture. More particularly, the systems and methods disclosed herein use reduced frequencies to enhance particle concentration in optimal shapes to improve their separation by gravity and subsequent collection. The systems and/or methods include an acoustic chamber containing an ultrasonic transducer and reflector that set up a multi-dimensional acoustic standing wave.

The systems and/or methods described herein can use a substantially vertical flow path for the fluid mixture through the acoustic chamber to improve separation of particles/secondary fluid from a primary fluid using fluid dynamics. The vertical flow path reduces velocity non-uniformities in the acoustic chamber resulting from gravity forces. In some examples, a dump diffuser is used to make the incoming flow more uniform, so that the efficiency of the acoustophoretic system is maximized. However, the presently disclosed examples are not limited to vertical flow.

Disclosed herein are acoustophoretic devices and methods for employing the devices in a separation process. An example device may include a housing having a sidewall that defines an acoustic chamber; at least one outlet in the acoustic chamber; at least one inlet in the acoustic chamber;

and at least one ultrasonic transducer coupled to the acoustic chamber (e.g., on or in the sidewall of the acoustic chamber or external to the acoustic chamber) to permit generation of an acoustic wave in the acoustic chamber, and at least one reflector located opposite to the at least one ultrasonic transducer (e.g., in or on the sidewall of the housing opposite the at least one ultrasonic transducer, or external to the acoustic chamber). The transducer may include piezoelectric material, such as a piezoelectric crystal or poly-crystal. The transducer can be driven by a signal, such as a voltage signal, a current signal, a magnetic signal, an electromagnetic signal, a capacitive signal, or any other type of signal to which the transducer is responsive to create a multi-dimensional acoustic standing wave in the acoustic chamber. The multi-dimensional acoustic standing wave may be formed with one or more secondary transducers that have an active portion that is directed to another transducer to generate an acoustic standing wave through their interactive operation. For example, the frequency, phase, amplitude or other parameters of the transducers may be controlled to cooperatively generate an acoustic standing wave therebetween. Such an acoustic standing wave may result from constructive/destructive interference between the acoustic waves generated by the respective transducers.

Also disclosed are methods of separating a host fluid from a second fluid or particulate, the methods comprising: flowing a mixture of the host fluid and the second fluid or particulate through an acoustophoresis device in a uniform flow, the device comprising: a housing having a sidewall that defines an acoustic chamber; at least one outlet from the acoustic chamber; at least one inlet to the acoustic chamber; and at least one ultrasonic transducer located in the acoustic chamber (e.g., on the sidewall of the acoustic chamber) and at least one reflector located in the acoustic chamber opposite the at least one ultrasonic transducer (e.g., on the sidewall of the housing opposite the at least one ultrasonic transducer), the transducer including a piezoelectric material driven by a voltage signal to create a multi-dimensional acoustic standing wave in the acoustic chamber; and trapping smaller particles of the second fluid or particulate in the acoustic standing wave to generate particle clusters that subsequently fall into the at least one lower outlet; wherein the acoustic standing wave has a ratio of lateral radiation force to axial radiation force of the same order of magnitude.

The piezoelectric material may be operated to produce a single trapping line, or to produce a set of vertically-staggered trapping lines. The at least one ultrasonic transducer may be driven at a frequency of about 0.5 MHz to about 4 MHz, or at a frequency below about 1.5 MHz.

In particular constructions, the at least one inlet is part of a dump diffuser. The at least one inlet may be located at a height between 5% and 75% of a height of the acoustic chamber. The at least one inlet may be in the shape of holes or slots that provide an initial flow direction parallel to the multi-dimensional acoustic standing wave generated by the at least one ultrasonic transducer. The device may include a shallow wall below the at least one inlet and leading to the at least one outlet, wherein the shallow wall has an angle of 60° or less relative to a horizontal plane.

The acoustophoresis device may be reflectionally symmetrical through a vertical plane. The at least one inlet may include a plurality of inlets located about the housing, such that the inflow of the mixture into the acoustic chamber is uniform and symmetrical.

In particular embodiments, the piezoelectric material is oriented to minimize cross-sectional area for straight vertical channels between trapping lines generated by the acoustic standing wave. The mixture of the host fluid and the second fluid or particulate is flowed through the acoustophoresis device at a rate of at least 4.65 mL/minute per $cm^2$.

The particulate may be Chinese hamster ovary (CHO) cells, NS0 hybridoma cells, baby hamster kidney (BHK) cells, or human cells, T cells, B cells, NK cells, algae, bacteria, viruses, or microcarriers.

Also disclosed in various embodiments herein are acoustophoresis devices comprising: a housing having a sidewall that defines an acoustic chamber; and at least one ultrasonic transducer coupled to the acoustic chamber (e.g., on the sidewall of the acoustic chamber) and at least one reflector coupled to the acoustic chamber opposite the at least one ultrasonic transducer (e.g., on the sidewall of the housing opposite the at least one ultrasonic transducer), the transducer including a piezoelectric material driven by a voltage signal to create a multi-dimensional acoustic standing wave in the acoustic chamber, resulting in a set of trapping lines in the acoustic chamber, the transducer being oriented to minimize cross-sectional area for straight vertical channels between the trapping lines. This can be done as described herein.

Also disclosed are methods of separating a host fluid from a second fluid or particulate, the method comprising: flowing a mixture of the host fluid and the second fluid or particulate through an acoustophoresis device in a uniform fashion, the device comprising: a housing having a sidewall that defines an acoustic chamber; at least one ultrasonic transducer coupled to the acoustic chamber (e.g., on the sidewall of the acoustic chamber) and at least one reflector coupled to the acoustic chamber opposite the at least one ultrasonic transducer (e.g., on the sidewall of the housing opposite the at least one ultrasonic transducer), the transducer including a piezoelectric material driven by a voltage signal to create a multi-dimensional acoustic standing wave in the acoustic chamber, resulting in a set of trapping lines in the acoustic chamber, the transducer being oriented to minimize cross-sectional area for straight vertical channels between the trapping lines; and capturing smaller particles of the second fluid or particulate in the trapping lines to cluster and continuously gravity separate the second fluid or particulate from the host fluid.

The at least one ultrasonic transducer may be driven at or below a frequency of about 1.5 MHz, and in particular at a frequency of about 1 MHz. In particular embodiments, the piezoelectric material of the at least one ultrasonic transducer can be PZT-8. The piezoelectric material can be mounted on a polymer film (e.g., poly etherether ketone). The piezoelectric material can be mounted on the polymer film with a pressure sensitive adhesive, such as an acrylic polymer (e.g., 2-ethyl hexyl acrylate).

Disclosed herein are various methods of generating particulate clusters. A mixture of a host fluid and particulate is flowed through an acoustophoretic device. The device comprises: a housing having a sidewall that defines an acoustic chamber; at least one outlet from the acoustic chamber; at least one inlet to the acoustic chamber; and at least one ultrasonic transducer located in the acoustic chamber (e.g., coupled to the sidewall of the acoustic chamber) and at least one reflector located in the acoustic chamber opposite the at least one ultrasonic transducer (e.g., coupled to the sidewall of the housing opposite the at least one ultrasonic transducer), the transducer including a piezoelectric material driven by a signal, which may be a voltage signal, to create an acoustic standing wave, which may be a planar or a multi-dimensional acoustic standing wave, in the acoustic chamber. For example, a voltage signal of a certain frequency is sent to drive the at least one ultrasonic transducer to create a multi-dimensional acoustic standing wave in the acoustic chamber to generate at least a first particulate cluster or group of clusters or one or more nodal planes or lines, and a second particulate cluster or group of clusters or one or more nodal planes or lines, that are each or in groups separated by a fluid channel running therebetween. The parameters of the signal, such as frequency, phase or amplitude, may be selectively tuned so as to selectively control, among other attributes, (a) a dimension, for example a diameter or a height, width or depth, of each particulate cluster or group of clusters or one or more nodal planes or lines, and/or (b) a dimension, for example a diameter or a height, width or depth, of the fluid channel. In some examples, the acoustic standing wave is a multi-dimensional acoustic standing wave with a lateral radiation force and an axial radiation force that are of the same order of magnitude. The acoustic standing wave may also be a planar standing wave, which may generate little or no lateral radiation force.

The parameters of the driving signal of the transducer(s), such as frequency, phase and/or amplitude, can be selectively tuned such that the first and second particulate clusters or group of clusters or one or more nodal planes or lines each have a dimension, for example a height, of from about 150 micrometers to about 1200 micrometers. The parameters of the drive signal can be selectively tuned such that the fluid channel has a dimension, for example a height, of from about 50 micrometers to about 500 micrometers. The parameters of the drive signal can be selectively tuned such that a ratio of a dimension, for example a height, of the first and second particulate clusters or group of clusters or one or more nodal planes or lines to a corresponding dimension, for example a height, of the fluid channel is from about 1:1 to about 5:1. The formation and control of the first and second particulate clusters or group of clusters or one or more nodal planes or lines and the fluid channel provides for a secondary physical filtration of materials, for example, in addition to the acoustic filtering. For example, the dimensions of the channels allow particles of a certain size to flow through, and causes particles larger than the channels to be blocked or retained.

In particular embodiments, the frequency of the voltage signal applied to the transducer is selectively tuned such that: the first and second particulate clusters each have a height of from about 150 micrometers to about 1200 micrometers, including from about 200 micrometers to about 600 micrometers; and the fluid channel has a height of from about 50 micrometers to about 500 micrometers, including from about 100 micrometers to about 250 micrometers; and a ratio of the height of the first and second particulate clusters to the height of the fluid channel is from about 1:1 to about 5:1.

In certain systems and/or methods, the acoustophoretic device is part of a filter train and can be configured to feed back separated fluid or particles to a fluid mixture source, such as a bioreactor. The methods disclosed herein can further comprise collecting the particulate clusters and sending the particulate clusters through at least one additional downstream filtration stage. The methods can also further comprise separating the particulate clusters from the host fluid to obtain a clarified host fluid, and sending the clarified host fluid through at least one additional downstream filtration stage.

The lateral radiation force mentioned above can be applied to the flowing fluid mixture to continuously trap the particulates in the nodal trapping lines. The particulates trapped in the nodal trapping lines may tend to cluster, agglomerate, aggregate, clump, or coalesce together, for example into cylindrical particulate clusters, and subsequently rise or settle out of the host fluid due to buoyancy or gravity forces. The so separated material, either clarified fluid and/or particulates, may exit the acoustic chamber.

Also disclosed are sets of particulate clusters generated by the methods described above, and nodal trapping lines generated by the methods described above.

Also disclosed herein are nodal trapping lines, comprising: a plurality of particulate clusters, adjacent particulate clusters and/or planar or nodal trapping lines being separated by a fluid channel running therebetween; wherein a ratio of a height of the particulate cluster to a width of the fluid channel is from about 1:1 to about 5:1.

Each particulate cluster may have a height of from about 150 micrometers to about 1200 micrometers. Each fluid channel may have a height of from about 50 micrometers to about 500 micrometers. Each of the first and second particulate clusters can be cylindrical.

Also disclosed herein are filter trains comprising a fluid mixture source, such as a vessel (e.g., a reaction vessel of a bioreactor), an acoustophoretic device, and a filtration device. The acoustophoretic device can be constructed as described herein, and may be configured to feed back separated primary (host) fluid or secondary fluid or particles to the fluid source. The acoustophoretic device may particularly include an acoustic chamber and at least one ultrasonic transducer coupled to the acoustic chamber, the transducer including a piezoelectric material driven by a drive signal to create a multi-dimensional acoustic standing wave in the acoustic chamber. The acoustophoretic device and the filtration device are fluidly connected to the vessel in series. In particular embodiments, the acoustophoretic device is located upstream of the filtration device (i.e., the acoustophoretic device is fluidly connected between the vessel and the filtration device). In other embodiments, the acoustophoretic device is located downstream of the filtration device (i.e., the filtration device is fluidly connected between the vessel and the acoustophoretic device). The filtration device can be selected from the group consisting of a depth filter, a sterile filter, a size exclusion filter, or a chromatography column.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 14A illustrates the trapping line configurations for seven peak amplitudes of an ultrasonic transducer of the present disclosure. FIG. 14B is a perspective view illustrating a separator of the present disclosure. The fluid flow direction and the trapping lines are shown. FIG. 14C is a view from the fluid inlet along the fluid flow direction (arrow 114) of FIG. 14B, showing the trapping nodes of the standing wave where particles would be captured. FIG. 14D is a view taken through the transducers face at the trapping line configurations, along arrow 116 as shown in FIG. 14B.

FIG. 19 shows the calculation of the cluster terminal velocity of a cylindrical cluster from the cluster drag and gravitational forces.

DETAILED DESCRIPTION

Figure 1:
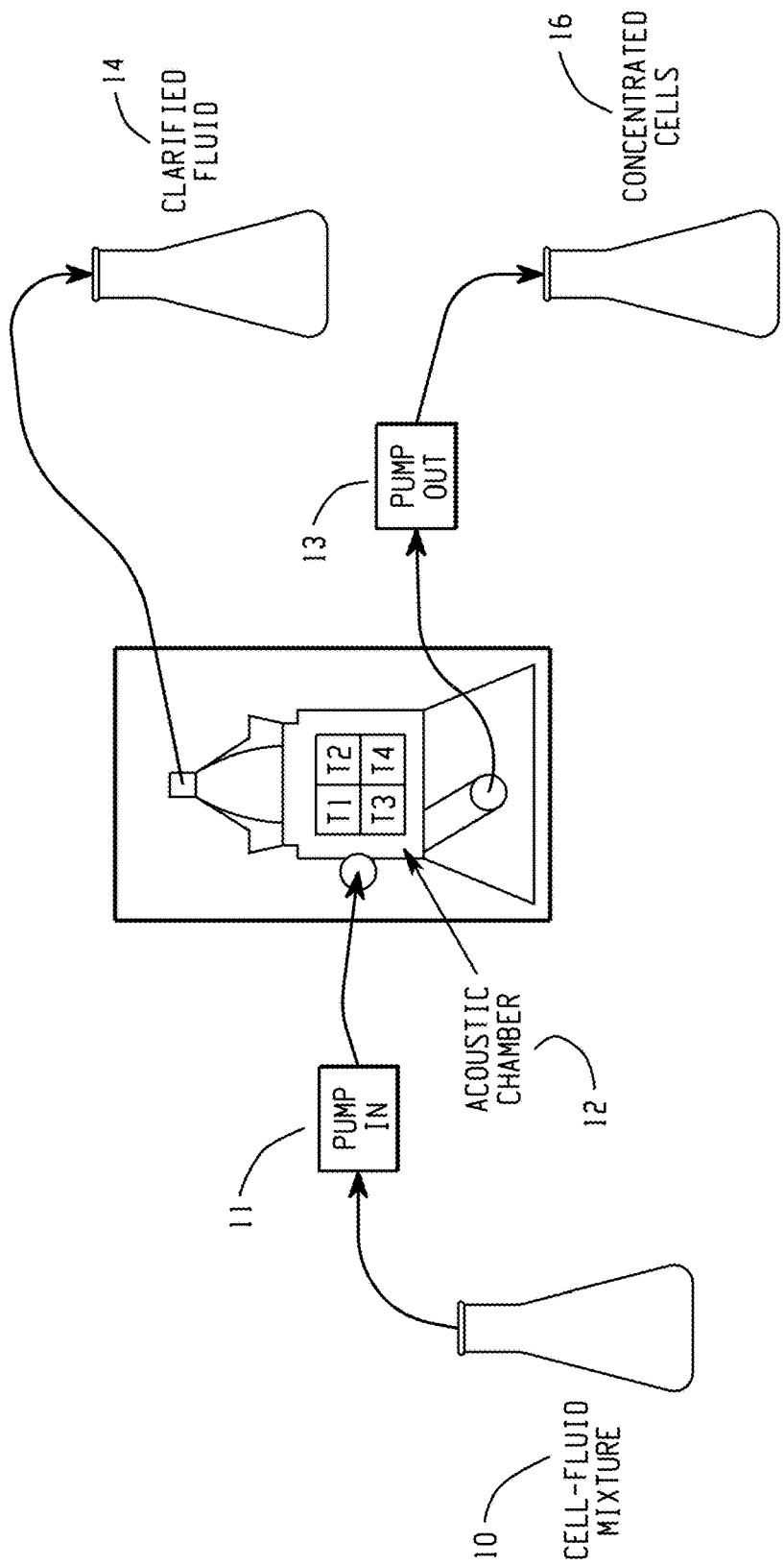
FIG. 1 illustrates an exemplary acoustophoretic separation system in which a cell-fluid mixture is clarified, such that clarified fluid and concentrated cells are removed therefrom in different containers.

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

The term "comprising" is used herein as requiring the presence of the named component and allowing the presence of other components. The term "comprising" should be construed to include the term "consisting of", which allows the presence of only the named component, along with any impurities that might result from the manufacture of the named component.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

The modifier "about" used in connection with a quantity is inclusive of the stated value and has the meaning dictated by the context. When used in the context of a range, the modifier "about" should also be considered as disclosing the range defined by the absolute values of the two endpoints. For example, the range of "from about 2 to about 10" also discloses the range "from 2 to 10." The term "about" may refer to plus or minus 10% of the indicated number. For example, "about 10%" may indicate a range of 9% to 11%, and "about 1" may mean from 0.9-1.1.

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "top" and "bottom" or "base" are used to refer to surfaces where the top is always higher than the bottom/base relative to an absolute reference, i.e. the surface of the earth. The terms "upwards" and "downwards" are also relative to an absolute reference; upwards is always against the gravity of the earth.

The term "parallel" should be construed in its lay sense of two surfaces that maintain a generally constant distance between them, and not in the strict mathematical sense that such surfaces will never intersect when extended to infinity.

The present application refers to "the same order of magnitude." Two numbers are of the same order of magnitude if the quotient of the larger number divided by the smaller number is a value of at least 1 and less than 10.

The present disclosure relates to acoustophoretic devices, methods and systems that employ multi-dimensional ultrasonic acoustic standing waves to trap, i.e., hold stationary, particles or a secondary fluid in a host fluid stream. The multi-dimensional acoustic standing wave generates tightly packed clusters of suspended fluid or particulate which continuously drop out or rise out of a flowing fluid mixture due to gravity or buoyancy forces. Systems employing the disclosed acoustophoretic devices and methods can operate at high flowrates with optimized fluid dynamics.

FIG. 1 is a broad overview of an acoustic wave separator system. A mixture 10 of a host fluid and a secondary phase (e.g. particles, cells, or a second different fluid) is sent via a pump 11 into an acoustic chamber 12. Here, the mixture is a cell-fluid mixture. In the acoustic chamber, the secondary phase is concentrated out of the host fluid. The concentrated cells 16 are sent by another pump 13 to be collected. The host fluid, which is more clarified due to the removal of the concentrated cells, is separately collected (indicated by reference numeral 14). Generally speaking, the acoustic chamber has at least one inlet and at least one outlet.

Figure 2:
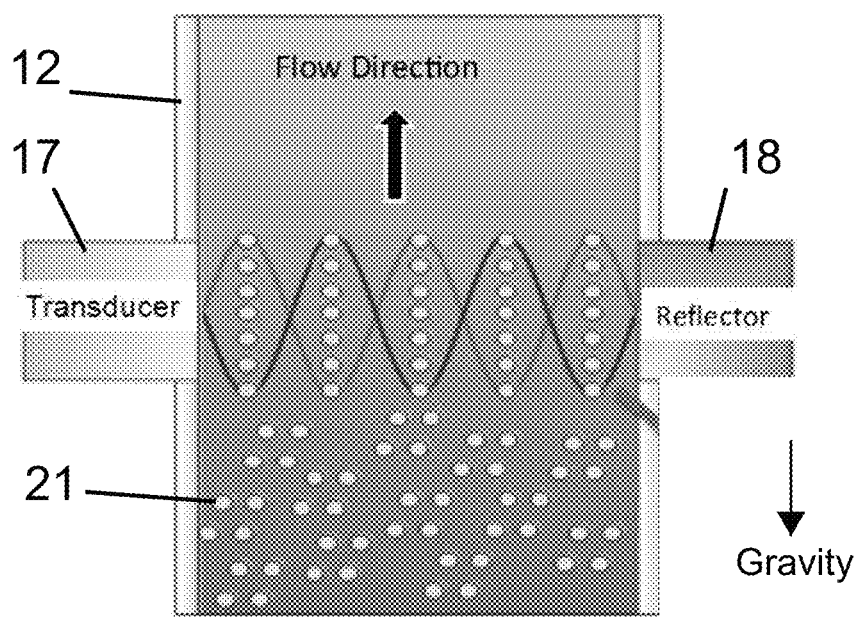
FIG. 2 illustrates standing acoustic wave(s) generated by an ultrasonic transducer and a reflector perpendicular to a direction of flow.

The acoustic chamber operates as shown in FIG. 2. One or more multi-dimensional acoustic standing waves are created between an ultrasonic transducer 17 and a reflector 18. The standing wave is illustrated as beginning and ending with local minima, however, other implementations are possible. For example, the standing wave can be offset at the transducer or the reflector so that local minima or maxima are spaced from the transducer or from the reflector. The reflected wave (or wave generated by an opposing transducer) can be in or out of phase with the transducer generated wave. The characteristics of the standing wave can be modified and/or controlled by the drive signal applied to the transducer, such as by modifying and/or controlling the phase, amplitude or frequency of the drive signal. Acoustically transparent or responsive materials may also be used with the transducer or reflector to modify and/or control the standing wave.

As the fluid mixture flows through acoustic chamber 12 with ultrasonic transducer 17 active, particles or secondary fluid 21 cluster, collect, agglomerate, aggregate, clump, or coalesce at the nodes or anti-nodes of the multi-dimensional acoustic standing wave, depending on the particles' or secondary fluid's acoustic contrast factor relative to the host fluid. The particles form clusters that eventually exit the multi-dimensional acoustic standing wave nodes or anti-nodes when the clusters have grown to a size large enough to overcome the holding force of the multi-dimensional acoustic standing wave (e.g. coalescence or agglomeration overcomes gravity or buoyancy forces). For fluids/particles that are more dense than the host fluid (such as the cells of FIG. 1), the clusters sink to the bottom and can be collected separately from the clarified host fluid. For fluids/particles that are less dense than the host fluid, the buoyant clusters float upwards and can be collected.

The scattering of the acoustic field off the particles results in a three dimensional acoustic radiation force, which acts as a three-dimensional trapping field. The acoustic radiation force is proportional to the particle volume (e.g. the cube of the radius) when the particle is small relative to the wavelength. The force is proportional to frequency and the acoustic contrast factor. The force scales with acoustic energy (e.g. the square of the acoustic pressure amplitude). When the acoustic radiation force exerted on the particles is stronger than the combined effect of fluid drag force and buoyancy and gravitational force, the particles are trapped within the acoustic standing wave field. The particle trapping in a multi-dimensional acoustic standing wave results in clustering, concentration, agglomeration and/or coalescence of the trapped particles. Relatively large solids of one material can thus be separated from smaller particles of a different material, the same material, and/or the host fluid through enhanced gravitational/buoyancy separation.

The multi-dimensional standing wave generates acoustic radiation forces in both the axial direction (e.g., in the direction of the standing wave, between the transducer and the reflector, which may be at an angle across the flow direction, and in some instances may be perpendicular to the flow direction) and the lateral direction (e.g., in the flow direction or transverse to the direction between the transducer and the reflector). As the mixture flows through the acoustic chamber, particles in suspension experience a strong axial force component in the direction of the standing wave. Since this acoustic force is across (e.g. perpendicular to) the flow direction and the drag force, it quickly moves the particles to pressure nodal planes or anti-nodal planes, depending on the contrast factor of the particle. The lateral acoustic radiation force acts to move the concentrated particles towards the center of each planar node, resulting in clustering, agglomeration or clumping. The lateral acoustic radiation force component can overcome fluid drag for such clumps of particles, to continually grow the clusters, which can exit the mixture due to gravity or buoyancy. The drop in drag per particle as the particle cluster increases in size, as well as the drop in acoustic radiation force per particle as the particle cluster grows in size, may separately or collectively influence operation of the acoustic separator device. In the present disclosure, the lateral force component and the axial force component of the multi-dimensional acoustic standing wave are of the same order of magnitude. In this regard, it is noted that in a multi-dimensional acoustic standing wave generated by a single transducer, the axial force is stronger than the lateral force, but the lateral force of such a multi-dimensional acoustic standing wave is much higher than the lateral force of a planar standing wave, usually by two orders of magnitude or more.

Particle drag and acoustic radiation force effects may influence optimal operation of the systems and methods of the present disclosure. At low Reynolds numbers of less than 10, laminar flow dominates, and viscous forces are much stronger than inertial forces.

As the particles are trapped by the multi-dimensional ultrasonic acoustic standing wave, they begin to aggregate and form a clump of particles. The drag on this clump of particles is a function of the geometry of the clump and is not merely the sum of the drag of the individual particles that make up the clump.

For laminar flow, the Navier Stokes equation is expressed as:

$$\rho\left(\frac{\partial V}{\partial t} + (V \cdot \nabla)V\right) = -\nabla P + \mu \nabla^2 V$$

where $$\frac{\partial V}{\partial t}$$

represents unsteady motion, $(V \cdot \nabla)V$ represents inertial motion, $-\nabla P$ represents pressure motion, and $\mu \nabla^2 V$ represents viscous motion.

For low Reynolds numbers, the unsteady motion and inertial motion terms can be ignored (i.e. set equal to zero), and the equation can be simplified to:

$$\nabla P = \mu \nabla^2 V$$

For a particle of diameter a, the following equations hold:

$$\nabla P \propto \mu \frac{V}{a}$$

$$F = 6\pi \mu a V$$

where P is pressure, $\mu$ is the dynamic viscosity, a is the particle diameter, V is the flow velocity, and F is the Stoke's drag.

Figure 3:
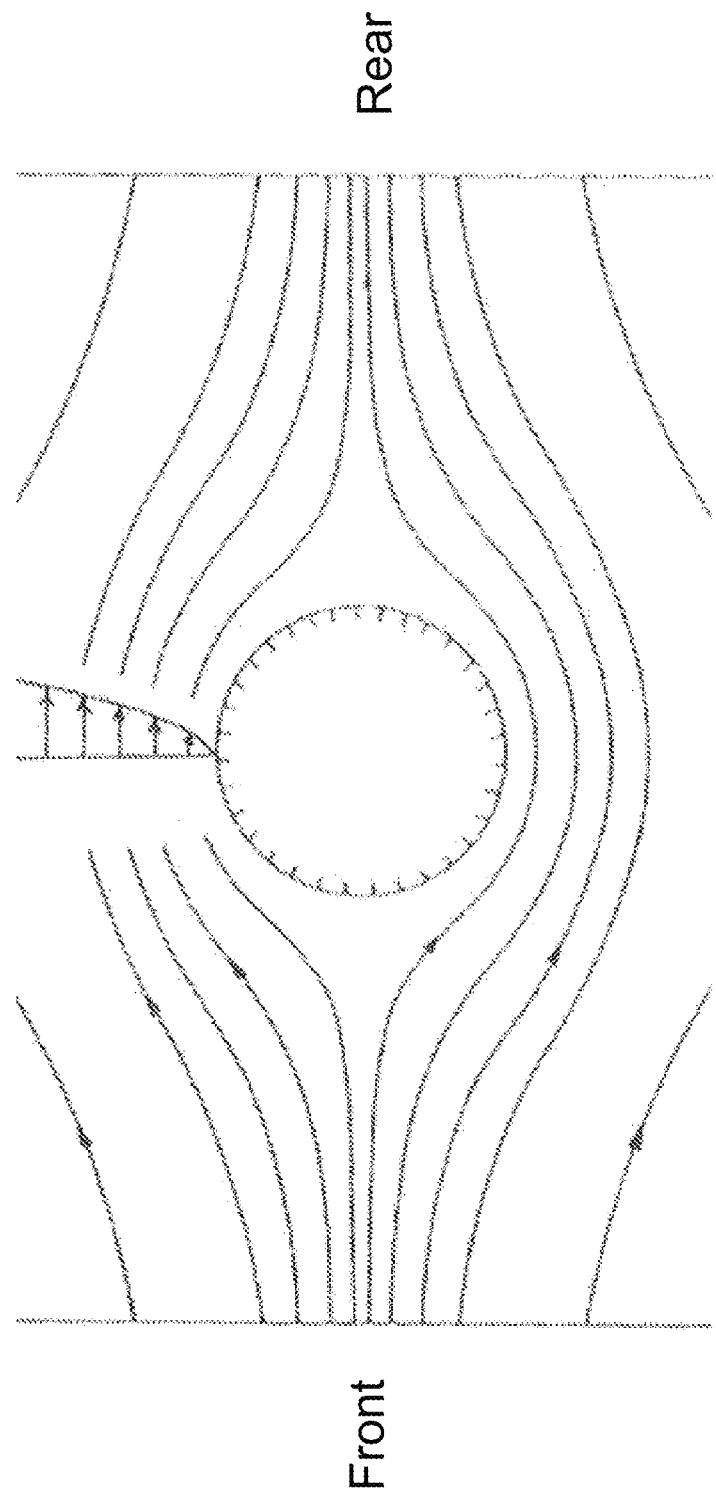
FIG. 3 illustrates the Stokes pressure distribution of a spherical particle cluster.

FIG. 3 is an illustration of fluid flow around a particle and the shear forces resulting therefrom. Fluid flow is from the left-hand side of the figure, and the left-hand side of the figure is also considered the front of the particle. The fluid flows into the front face of the particle, increasing pressure. The shear forces then drag the flow around the body while continually decreasing pressure. Finally, the shear forces drag the fluid away from the back face region lowering pressure. That is, the shear forces generally drag the fluid over the body.

Figure 4:
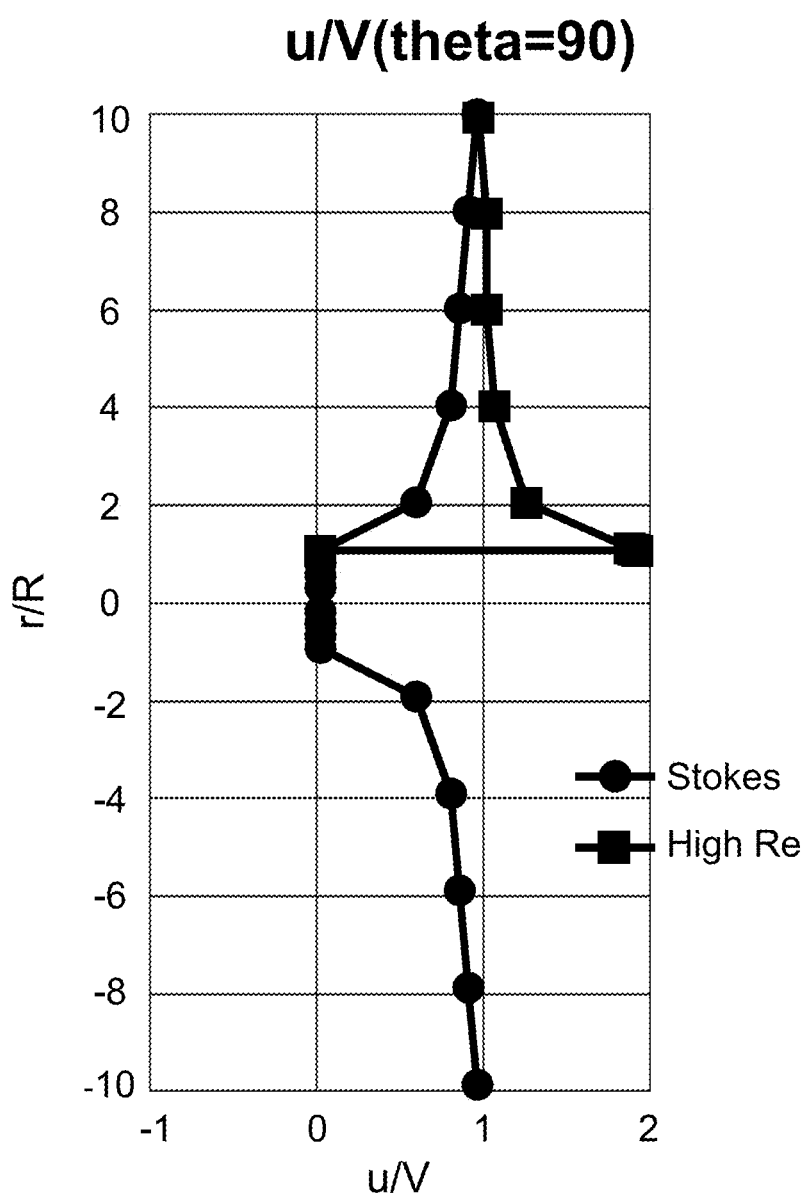
FIG. 4 is a graph illustrating the normalized flow velocity profile (u/V) over a sphere at the 90° location from the flow axis in terms of radiuses from the particle (r/R). The y-axis is r/R, and runs from −10 (at the bottom) to +10 (at the top) in intervals of 2. The x-axis runs from −1 to +2 in intervals of 1.

FIG. 4 is a graph illustrating the difference between Stokes flow (i.e. low Reynolds number, abbreviated Stokes) and flow at high Reynolds numbers (High Re) on the side of the particle (theta=90°). The y-axis is r/R, where r represents the distance from the particle along the flow direction and R is the particle radius, (−10=10 radiuses in front of the particle, 0=the surface of the particle, and +10=10 radiuses behind the particle). The x-axis is u/V, where u is the flow velocity on the particle surface and V is the approaching flow velocity.

Considering FIG. 4, for High Re, a maximum velocity ratio u/V is 2 on the surface. However, for Stokes flow, the velocity ratio is zero on the surface. This result indicates that when two particles come close to each other with a fluid flow at low Reynolds numbers, the flow between the two particles is close to zero. In Stokes flow, there is no velocity increase at the maximum size of the particle, but velocity variations can occur even at 4 radiuses or more.

Figure 5:
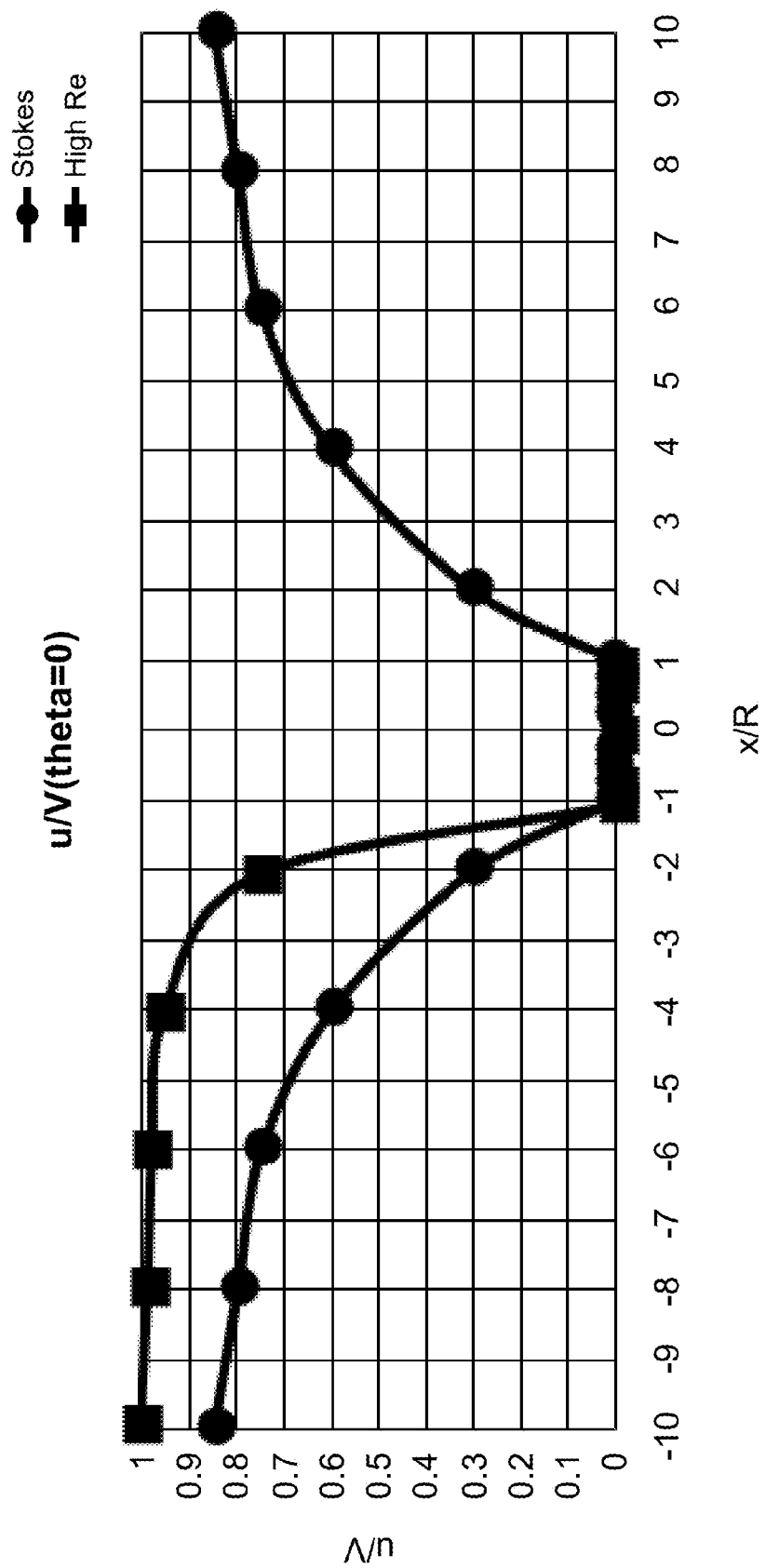
FIG. 5 is a graph illustrating the normalized flow velocity profile (u/V) over a sphere at the 0° location from the flow axis in terms of radiuses from the particle (x/R). The y-axis is u/V, and runs from 0 to 1 in intervals of 0.1. The x-axis is r/R, and runs from −10 to +10 in intervals of 1.

FIG. 5 is a graph illustrating the difference between Stokes flow (i.e. low Reynolds number, abbreviated Stokes) and flow at high Reynolds numbers (High Re) on the front of the particle (theta=0°). For Stokes flow, the flowfield starts changing far in front of the particle, at values of x/R=6, whereas the High Re flow does not start changing until x/R=2.

An approximate analytical model can be developed to compare the fluid drag on an agglomerated cluster of particles versus the fluid drag on the individual particles. Four assumptions are made. First, interior particles on the cluster are shielded from shear forces. Second, there is no fluid flow between particles of the cluster; this assumption is supported by FIG. 4. Third, the cluster of particles can be approximated as a sphere. Fourth, drag on the spherical cluster is Stokes drag.

The analytical model can be developed as follows:

$$\frac{F_D}{F_d} = \frac{\gamma}{\phi}\left(\frac{d}{D}\right)^2$$

where $F_D=6\pi\mu DV$ is the total force on a spherical cluster of diameter D and $Fd=N6\pi\mu dV$ is the sum of all particle forces within the spherical cluster, assuming each particle has diameter d, using Stokes drag if flow passes through the clump at free stream velocity. In these equations, $\mu$ represents fluid viscosity, N represents the number of particles in the cluster, and $F_D/F_d$ is the ratio of the drag on the cluster to the drag on all of the individual particles that form the cluster. © (gamma) is the particle density divided by the fluid density. $\phi$ represents the concentration of particles in the cluster, or the percentage of the volume of the cluster that is occupied by particles. For equal spheres, the densest possible packing is about 74%.

Figure 6:
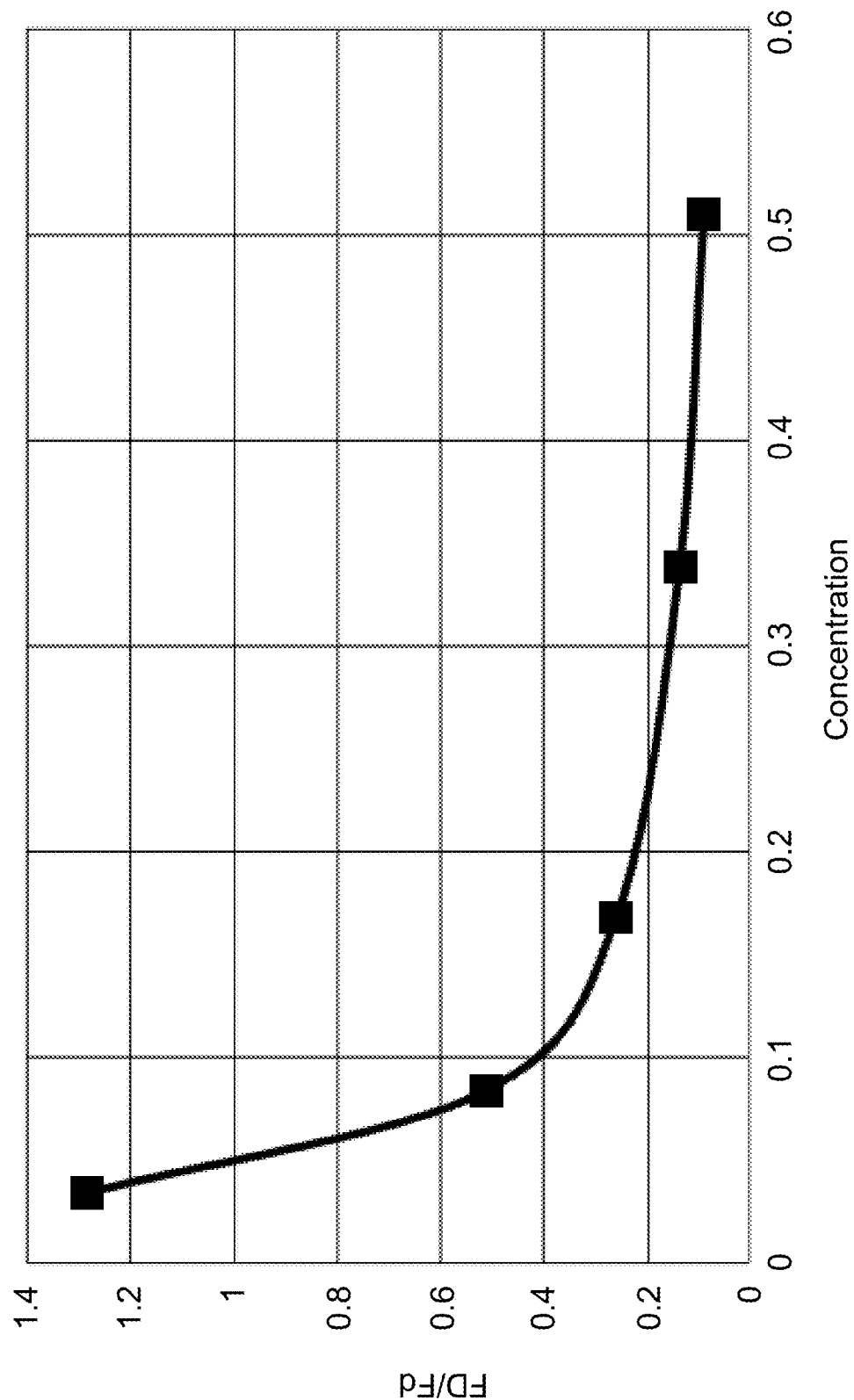
FIG. 6 is a graph of the ratio of the drag on a particle cluster over the total drag on the individual particles in the cluster (FD/Fd) versus the cluster concentration (i.e., the percent of the cluster volume occupied by particles). The y-axis runs from 0 to 1.4 in intervals of 0.2. The x-axis runs from 0 to 0.6 in intervals of 0.1.

FIG. 6 is a graph showing the $F_D/F_d$ versus concentration ($\phi$) when d/D=0.2, $\gamma$=1.1, and the Reynolds number is far less than 1. As seen here, the $F_D/F_d$ ratio is much smaller at higher concentrations. In other words, the reduction in drag increases as the density of the cluster increases.

Next, the effect of the Reynolds number and the particle concentration was tested using computation fluid dynamics (CFD). The cluster was simulated as a cubic cluster of 27 particles (3×3×3) with a spacing of 0.001 meters between particles. The Reynolds numbers tested were 0.01, 0.1, 1, 10, and 100, at a concentration of 11.3%. Particle concentrations were tested at 30%, 19%, 11.3%, 10%, 8%, 6%, 5%, 4%, 3%, 2%, and 1%, at Re=0.01. The particle concentration was varied by changing the spacing between the particles.

Figure 7:
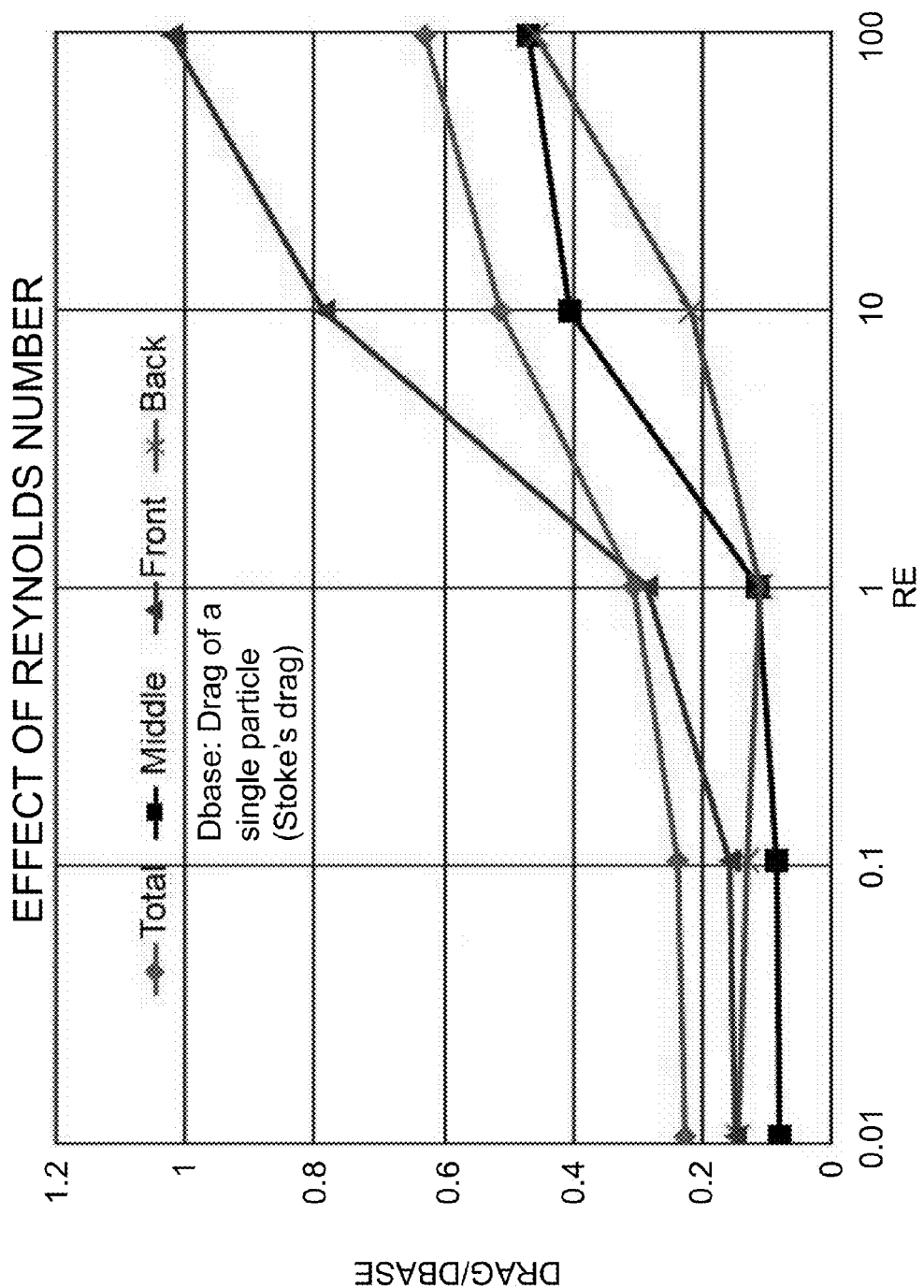
FIG. 7 is a graph showing the Drag/Dbase versus the Reynolds number for a simulation of 27 particles arranged in a 3×3×3 cubical array, with lines representing the ratios for the total drag and the drag on the front, middle, and back sets of particles. The y-axis runs from 0 to 1.2 in intervals of 0.2. The x-axis is logarithmic and is labeled 0.01, 0.1, 1, 10, and 100.

FIG. 7 is a graph showing the drag/Dbase versus the Reynolds number (Re) for four values: total, middle, front, and back. Front, Middle, and Back are the drag for the nine particles in the front, middle, and back locations of the cubic cluster. For these three lines, "Dbase" is the Stokes drag for nine isolated particles. "Total" is the total drag for the entire cluster of 27 particles, and for this value "Dbase" is the Stokes drag for 27 isolated particles. Generally, these results showed that a cluster of particles had less drag than isolated particles, regardless of their position in the cluster, at Re up to 100.

Figure 8:
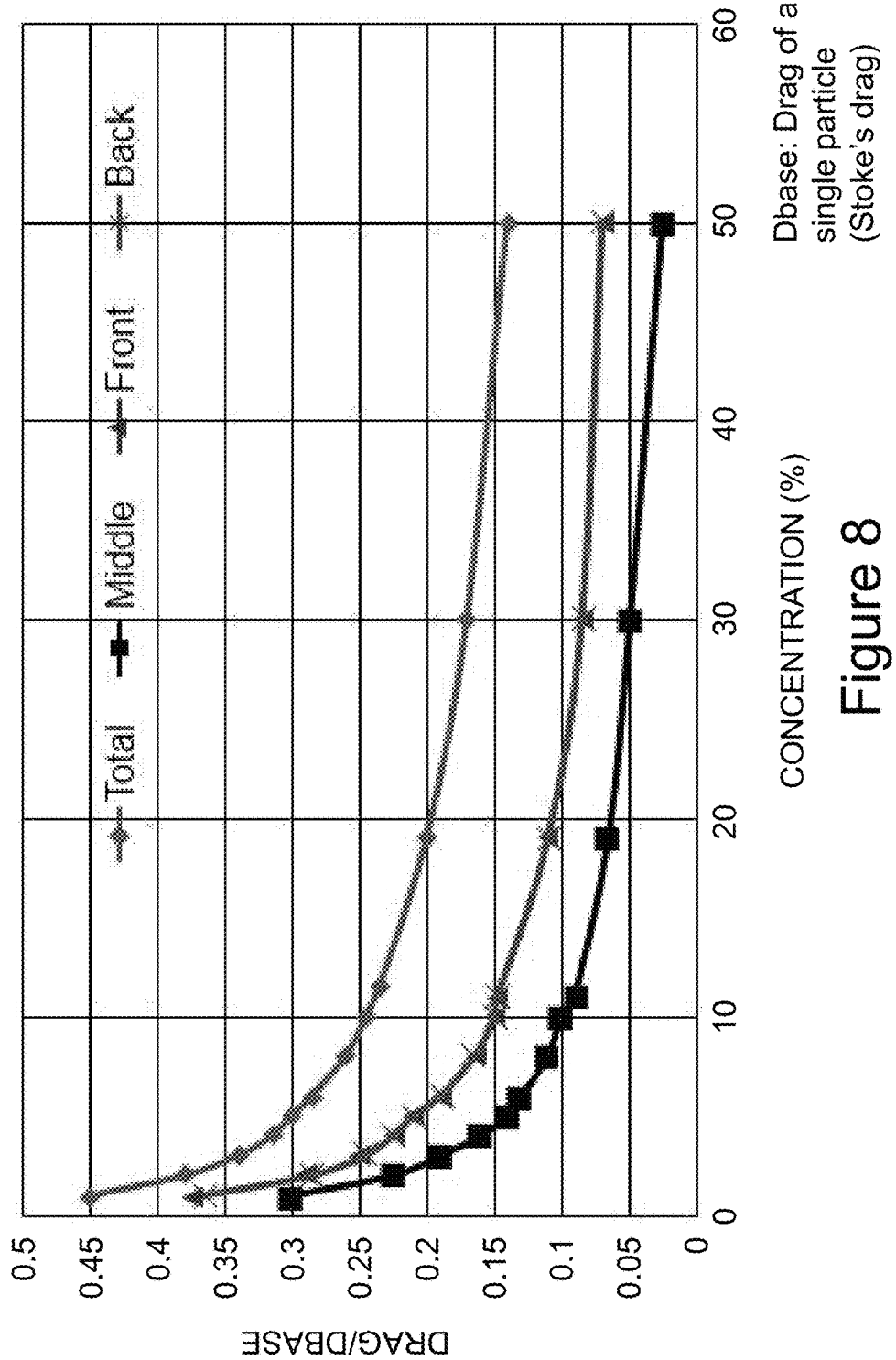
FIG. 8 is a graph showing the Drag/Dbase versus the particle concentration (%) for a simulation of 27 particles arranged in a 3×3×3 cubical array, with lines representing the ratios for the total drag and the drag on the front, middle, and back sets of particles. The y-axis runs from 0 to 0.5 in intervals of 0.05. The x-axis runs from 0 to 60 in intervals of 10.

FIG. 8 is a graph showing drag/Dbase versus the concentration. The lines have the same meaning as in FIG. 7. This graph confirms the reduction in drag as the concentration increases.

It is noted that the drag reduction effect seen in FIG. 7 and FIG. 8 is a localized effect, and may occur when the particles in the cluster are very close together (localized, i.e. the particle concentration is very high) with clear fluid flowing around the cluster. In FIG. 7 and FIG. 8, the spacing between particles was 0.001. When the model was rerun with spacing between particles close to 0.1 and Re=0.01 such that the particles were spaced far apart and were not localized, the total drag on the "Middle" particles alone was equal to the total drag of the isolated particles at n=75. This indicates that drag increases if the particles in the cluster are not tightly packed, even at lower Re, which is consistent with literature.

The analytical model shows that with Stokes flow, fluid drag decreases dramatically once clumping begins. This results from the decrease in velocity between particles caused by shear forces dominant shear forces in the flowfield. It is thus desirable to have the particles cluster as quickly as possible to get good trapping. The lateral acoustic radiation forces generated by the multi-dimensional acoustic standing wave using a single acoustic transducer are capable of overcoming fluid drag force and driving the trapped particles to clustering regions, packing them more tightly until they gravity/buoyancy separate. Importantly, higher flowrates may be possible with the use of lower frequencies. Longer wavelengths at these lower frequencies result in a larger D/d ratio, which means the same acoustic force is capable of trapping the particle clusters with higher velocity flow. The analytical model further suggests that better trapping can be achieved with higher local concentration, which leads to tightly packed cylindrical clusters.

Prior to discussing further optimization of the systems, it is helpful to provide an explanation now of how multi-dimensional acoustic standing waves are generated. The multi-dimensional acoustic standing wave used for particle collection is obtained by driving an ultrasonic transducer composed of a piezoelectric material at a frequency that generates the acoustic standing wave and excites a fundamental 3D vibration mode of the transducer. The transducer may be composed of various materials that may be perturbed to generate an ultrasonic wave. For example, the transducer may be composed of a piezoelectric material, including a piezoelectric crystal or poly-crystal. Perturbation of the piezoelectric material, which may be a piezoelectric crystal or poly-crystal, in the ultrasonic transducer to achieve a multimode response allows for generation of a multidimensional acoustic standing wave. A piezoelectric material can be specifically designed to deform in a multimode response at designed frequencies, allowing for generation of a multi-dimensional acoustic standing wave. The multi-dimensional acoustic standing wave may be generated with distinct modes of the piezoelectric material such as a 3×3 mode that generates multidimensional acoustic standing waves. A multitude of multidimensional acoustic standing waves may also be generated by allowing the piezoelectric material to vibrate through many different mode shapes. Thus, the material can be selectively excited to operate in multiple modes such as a 0×0 mode (i.e. a piston mode), 1×1, 2×2, 1×3, 3×1, 3×3, and other higher order modes. The material can be operated to cycle through various modes, in a sequence or skipping past one or more modes, and not necessarily in a same order with each cycle. This switching or dithering of the material between modes allows for various multidimensional wave shapes, along with a single piston mode shape to be generated over a designated time.

Some further explanation of the ultrasonic transducers used in the devices, systems, and methods of the present disclosure may be helpful as well. In this regard, the transducers may be composed of a piezoelectric material, such as a piezoelectric crystal or poly-crystal, which may be made of PZT-8 (lead zirconate titanate). Such crystals may have a major dimension on the order of 1 inch and larger. The resonance frequency of the piezoelectric material may nominally be about 2 MHz, and may be operated at one or more frequencies. Each ultrasonic transducer module can have only one crystal, or can have multiple crystals that each act as a separate ultrasonic transducer and are either controlled by one or multiple controllers, which controllers may include signal amplifiers. The piezoelectric material can be square, rectangular, irregular polygon, or generally of any arbitrary shape. The transducer(s) is/are used to create a pressure field that generates forces of the same order of magnitude both orthogonal to the standing wave direction (lateral) and in the standing wave direction (axial).

Figure 9:
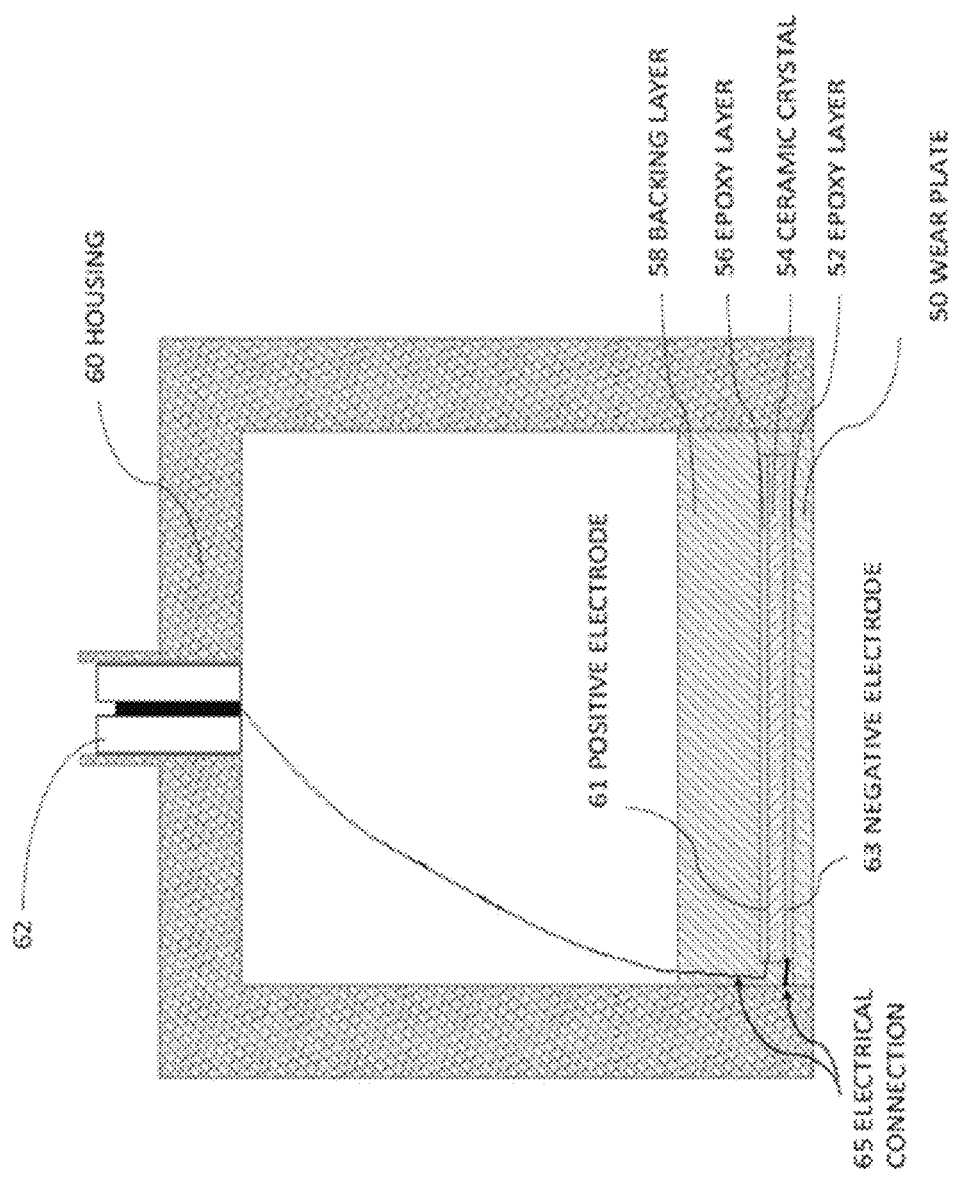
FIG. 9 is a cross-sectional diagram of a conventional ultrasonic transducer.

FIG. 9 is a cross-sectional diagram of a conventional ultrasonic transducer. This transducer has a wear plate 50 at a bottom end, epoxy layer 52, ceramic crystal 54 (made of, e.g. PZT), an epoxy layer 56, and a backing layer 58. On either side of the ceramic crystal, there is an electrode: a positive electrode 61 and a negative electrode 63. The epoxy layer 56 attaches backing layer 58 to the crystal 54. The entire assembly is contained in a housing 60 which may be made out of, for example, aluminum. An electrical adapter 62 provides connection for wires to pass through the housing and connect to leads (not shown) which attach to the crystal 54. Typically, backing layers are designed to add damping and to create a broadband transducer with uniform displacement across a wide range of frequency and are designed to suppress excitation at particular vibrational eigen-modes. Wear plates are usually designed as impedance transformers to better match the characteristic impedance of the medium into which the transducer radiates.

Figure 10:
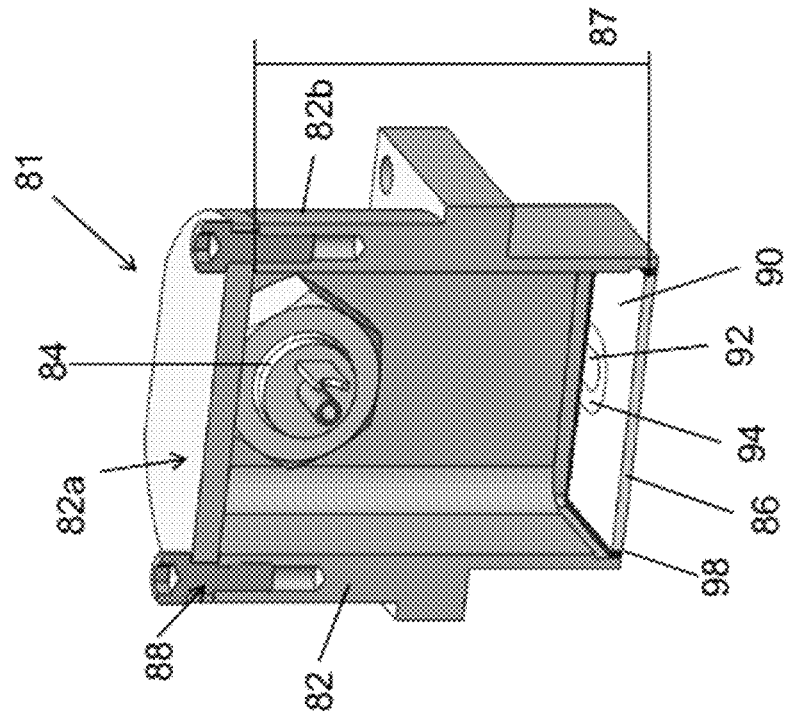
FIG. 10 is a cross-sectional diagram of an ultrasonic transducer of the present disclosure. An air gap is present within the transducer, and no backing layer or wear plate is present.

FIG. 10 is a cross-sectional view of an ultrasonic transducer 81 according to an example of the present disclosure. Transducer 81 is shaped as a disc or a plate, and has an aluminum housing 82. The piezoelectric crystal is a mass of perovskite ceramic crystals, each consisting of a small, tetravalent metal ion, usually titanium or zirconium, in a lattice of larger, divalent metal ions, usually lead or barium, and O2-ions. As an example, a PZT (lead zirconate titanate) crystal 86 defines the bottom end of the transducer, and is exposed from the exterior of the housing. The crystal has an interior surface and an exterior surface. The crystal is supported on its perimeter by a small elastic layer 98, e.g. silicone or similar material, located between the crystal and the housing. Put another way, no wear layer is present. In particular embodiments, the crystal is an irregular polygon, and in further embodiments is an asymmetrical irregular polygon.

Figure 11:
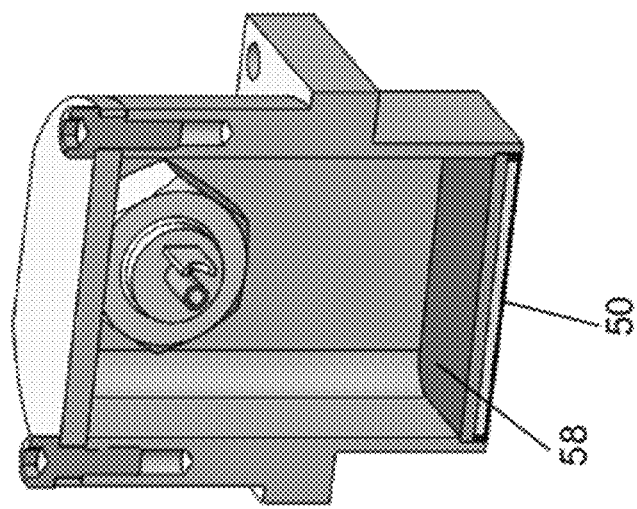
FIG. 11 is a cross-sectional diagram of an ultrasonic transducer of the present disclosure. An air gap is present within the transducer, and a backing layer and wear plate are present.

Screws 88 attach an aluminum top plate 82a of the housing to the body 82b of the housing via threads. The top plate includes a connector 84 for powering the transducer. The top surface of the PZT crystal 86 is connected to a positive electrode 90 and a negative electrode 92, which are separated by an insulating material 94. The electrodes can be made from any conductive material, such as silver or nickel. Electrical power is provided to the PZT crystal 86 through the electrodes on the crystal. Note that the crystal 86 has no backing layer or epoxy layer. Put another way, there is an air gap 87 in the transducer between aluminum top plate 82a and the crystal 86 (i.e. the housing is empty). A minimal backing 58 (on the interior surface) and/or wear plate 50 (on the exterior surface) may be provided in some embodiments, as seen in FIG. 11.

The transducer design can affect performance of the system. A typical transducer is a layered structure with the ceramic crystal bonded to a backing layer and a wear plate. Because the transducer is loaded with the high mechanical impedance presented by the standing wave, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers, there is no wear plate or backing, allowing the crystal to vibrate in one of its eigenmodes (i.e. near eigenfrequency) with a high Q-factor. The vibrating ceramic crystal/disk is directly exposed to the fluid flowing through the acoustic chamber.

Removing the backing (e.g. making the crystal air backed) also permits the ceramic crystal to vibrate at higher order modes of vibration with little damping (e.g. higher order modal displacement). In a transducer having a crystal with a backing, the crystal vibrates with a more uniform displacement, like a piston. Removing the backing allows the crystal to vibrate in a non-uniform displacement mode. The higher order the mode shape of the crystal, the more nodal lines the crystal has. The higher order modal displacement of the crystal creates more trapping lines, although the correlation of trapping line to node is not necessarily one to one, and driving the piezoelectric material/crystal at a higher frequency will not necessarily produce more trapping lines.

In some embodiments, the crystal may have a backing that minimally affects the Q-factor of the crystal (e.g. less than 5%). The backing may be made of a substantially acoustically transparent material such as balsa wood, foam, or cork which allows the crystal to vibrate in a higher order mode shape and maintains a high Q-factor while still providing some mechanical support for the crystal. The backing layer may be a solid, or may be a lattice having holes through the layer, such that the lattice follows the nodes of the vibrating crystal in a particular higher order vibration mode, providing support at node locations while allowing the rest of the crystal to vibrate freely. The goal of the lattice work or acoustically transparent material is to provide support without lowering the Q-factor of the crystal or interfering with the excitation of a particular mode shape.

Placing the crystal in direct contact with the fluid also contributes to the high Q-factor by avoiding the dampening and energy absorption effects of the epoxy layer and the wear plate. Other embodiments may have wear plates or a wear surface to prevent the PZT, which contains lead, from contacting the host fluid. This may be desirable in, for example, biological applications such as separating blood. Such applications might use a wear layer such as chrome, electrolytic nickel, or electroless nickel. Chemical vapor deposition could also be used to apply a layer of poly(p-xylylene) (e.g. Parylene) or other polymers or polymer films. Organic and biocompatible coatings such as silicone or polyurethane are also usable as a wear surface.

Figure 12:
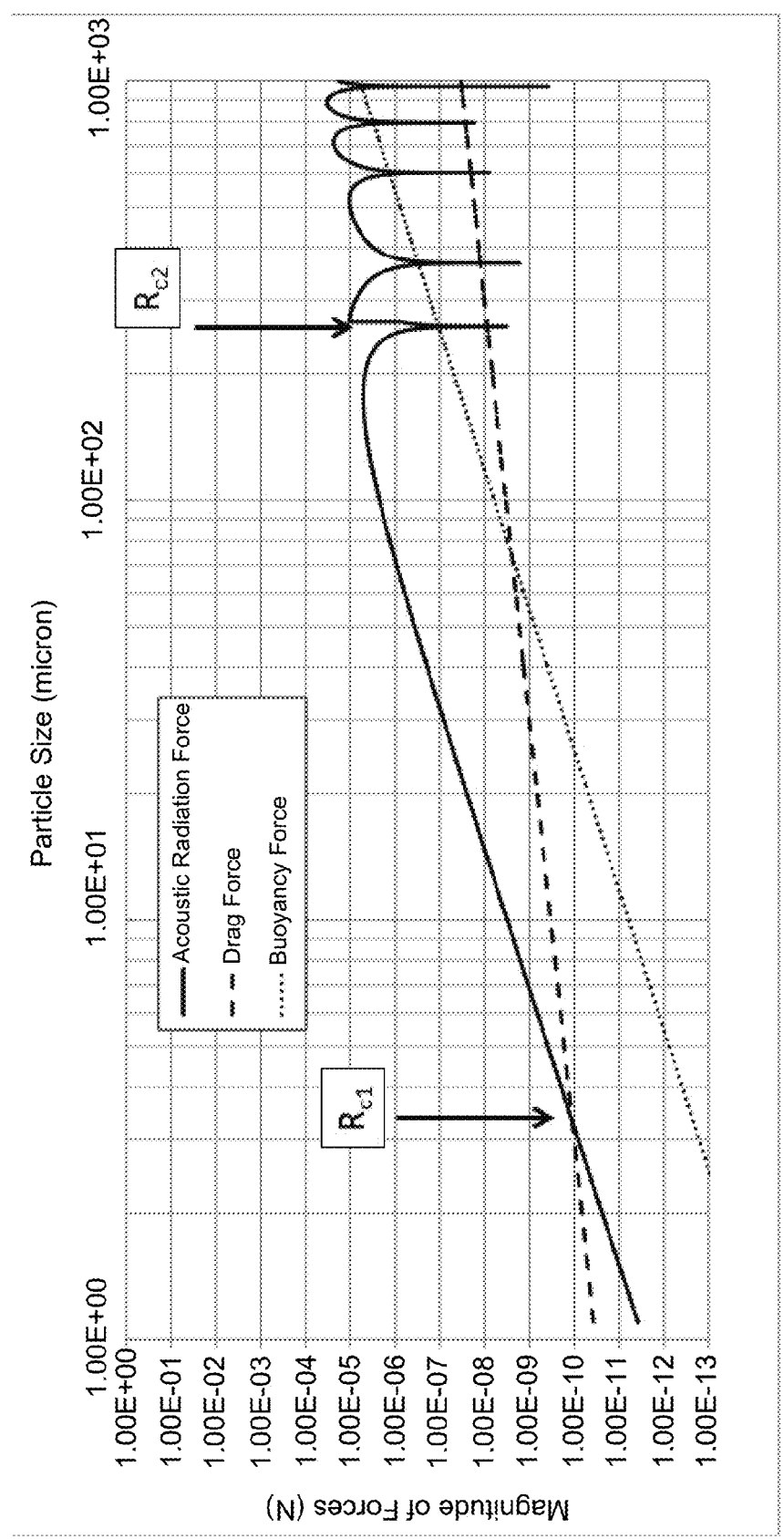
FIG. 12 is a graph showing the relationship of the acoustic radiation force, buoyancy force, and Stokes' drag force to particle size. The horizontal axis is in microns (μm) and the vertical axis is in Newtons (N).

FIG. 12 is a log-log graph (logarithmic y-axis, logarithmic x-axis) that shows the scaling of the acoustic radiation force, fluid drag force, and buoyancy force with particle radius, and provides an explanation for the separation of particles using acoustic radiation forces. The buoyancy force is a particle volume dependent force, and is therefore negligible for particle sizes on the order of micron, but grows, and becomes significant for particle sizes on the order of hundreds of microns. The fluid drag force (Stokes drag force) scales linearly with fluid velocity, and therefore typically exceeds the buoyancy force for micron sized particles, but is negligible for larger sized particles on the order of hundreds of microns. The acoustic radiation force scaling is different. When the particle size is small, Gor'kov's equation is accurate and the acoustic trapping force scales with the volume of the particle. Eventually, when the particle size grows, the acoustic radiation force no longer increases with the cube of the particle radius, and will rapidly vanish at a certain critical particle size. For further increases of particle size, the radiation force increases again in magnitude but with opposite phase (not shown in the graph). This pattern repeats for increasing particle sizes.

Initially, when a suspension is flowing through the system with primarily small micron sized particles, the acoustic radiation force balances the combined effect of fluid drag force and buoyancy force to permit a particle to be trapped in the standing wave. In FIG. 12 this trapping happens at a particle size labeled as $R_{c1}$. The graph then indicates that all larger particles will be trapped as well. Therefore, when small particles are trapped in the standing wave, particle clustering/coalescence/clumping/aggregation/agglomeration takes place, resulting in continuous growth of effective particle size. As particles cluster, the total drag on the cluster is much lower than the sum of the drag forces on the individual particles. In essence, as the particles cluster, they shield each other from the fluid flow and reduce the overall drag of the cluster. As the particle cluster size grows, the acoustic radiation force reflects off the cluster, such that the net acoustic radiation force decreases per unit volume. The acoustic lateral forces on the particles may be larger than the drag forces for the clusters to remain stationary and grow in size.

Particle size growth continues until the buoyancy force becomes dominant, which is indicated by a second critical particle size, $R_{c2}$. The buoyancy force per unit volume of the cluster remains constant with cluster size, since it is a function of the particle density, cluster concentration and gravity constant. Therefore, as the cluster size increases, the buoyancy force on the cluster increases faster than the acoustic radiation force. At the size $R_{c2}$, the particles will rise or sink, depending on their relative density with respect to the host fluid. At this size, acoustic forces are secondary, gravity/buoyancy forces become dominant, and the particles naturally drop out or rise out of the host fluid. Some particles may remain in the acoustic wave as clusters of others drop out, and those remaining particles and new particles entering the acoustic chamber with the flow of a fluid mixture continue to move to the three-dimensional nodal locations, repeating the growth and drop-out process. This phenomenon explains the quick drops and rises in the acoustic radiation force beyond size $R_{c2}$. Thus, FIG. 12 explains how small particles can be trapped continuously in a standing wave, grow into larger particles or clumps, and then eventually will rise or settle out because of increased buoyancy/gravity force.

In some examples, the size, shape, and thickness of the transducer can determine the transducer displacement at different frequencies of excitation. Transducer displacement with different frequencies may affect particle separation efficiency. Higher order modal displacements can generate three-dimensional acoustic standing waves with strong gradients in the acoustic field in all directions, thereby creating strong acoustic radiation forces in all directions, which forces may, for example be equal in magnitude, leading to multiple trapping lines, where the number of trapping lines correlate with the particular mode shape of the transducer.

Figure 13:
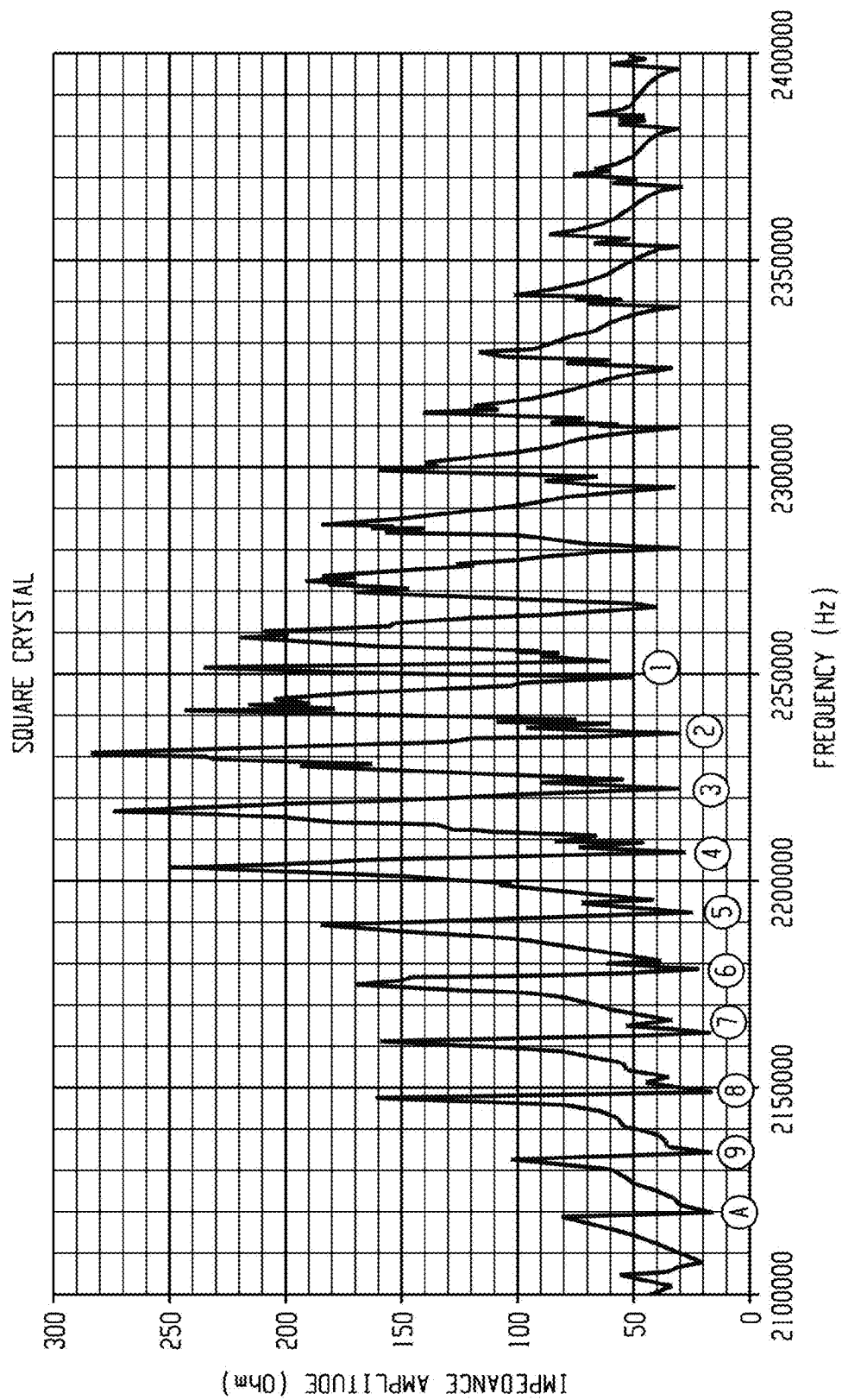
FIG. 13 is a graph of electrical impedance amplitude versus frequency for a square transducer driven at different frequencies.

FIG. 13 shows the measured electrical impedance amplitude of the transducer as a function of frequency in the vicinity of the 2.2 MHz transducer resonance. The minima in the transducer electrical impedance correspond to acoustic resonances of a water column and represent potential frequencies for operation. Numerical modeling has indicated that the transducer displacement profile varies significantly at these acoustic resonance frequencies, and thereby directly affects the acoustic standing wave and resulting trapping force. Since the transducer operates near its thickness resonance, the displacements of the electrode surfaces are essentially out of phase. The typical displacement of the transducer electrodes may not be uniform and varies depending on frequency of excitation. Higher order transducer displacement patterns result in higher trapping forces and multiple stable trapping lines for the captured particles.

To investigate the effect of the transducer displacement profile on acoustic trapping force and particle separation efficiencies, an experiment was repeated ten times, with all conditions identical except for the excitation frequency. Ten consecutive acoustic resonance frequencies, indicated by circled numbers 1-9 and letter A on FIG. 13, were used as excitation frequencies. The conditions were experiment duration of 30 min, a 1000 ppm oil concentration of approximately 5-micron SAE-30 oil droplets, a flow rate of 500 ml/min, and an applied power of 20 W.

As the emulsion passed by the transducer, the trapping lines of oil droplets were observed and characterized. The characterization involved the observation and pattern of the number of trapping lines across the fluid channel, as shown in FIG. 14A, for seven of the ten resonance frequencies identified in FIG. 13.

FIG. 14B shows an isometric view of the system in which the trapping line locations are being determined. FIG. 14C is a view of the system as it appears when looking down the inlet, along arrow 114. FIG. 14D is a view of the system as it appears when looking directly at the transducer face, along arrow 116.

The effect of excitation frequency clearly determines the number of trapping lines, which vary from a single trapping line at the excitation frequency of acoustic resonance 5 and 9, to nine trapping lines for acoustic resonance frequency 4. At other excitation frequencies four or five trapping lines are observed. Different displacement profiles of the transducer can produce different (more) trapping lines in the standing waves, with more gradients in displacement profile generally creating higher trapping forces and more trapping lines. It is noted that although the different trapping line profiles shown in FIG. 14A were obtained at the frequencies shown in FIG. 13, these trapping line profiles can also be obtained at different frequencies.

FIG. 14A shows the different crystal vibration modes possible by driving the piezoelectric material/crystal to vibrate at different fundamental frequencies of vibration. The 3D mode of vibration of the crystal is carried by the acoustic standing wave across the fluid in the chamber all the way to the reflector and back. The resulting multi-dimensional standing wave can be thought of as containing two components. The first component is a planar out-of-plane motion component (uniform displacement across crystal surface) of the crystal that generates a standing wave, and the second component is a displacement amplitude variation with peaks and valleys occurring in lateral directions across the crystal surface. Three-dimensional force gradients are generated by the standing wave. These three-dimensional force gradients result in lateral radiation forces that stop and trap the particles with respect to the flow by overcoming the viscous drag force. In addition, the lateral radiation forces are responsible for creating tightly packed clusters of particles. Therefore, particle separation and gravity-driven collection depends on generating a multi-dimensional standing wave that can overcome the particle drag force as the mixture flows through the acoustic standing wave. Multiple particle clusters are formed along trapping lines in the axial direction of the standing wave, as presented schematically in FIG. 14A.

Figure 15B:
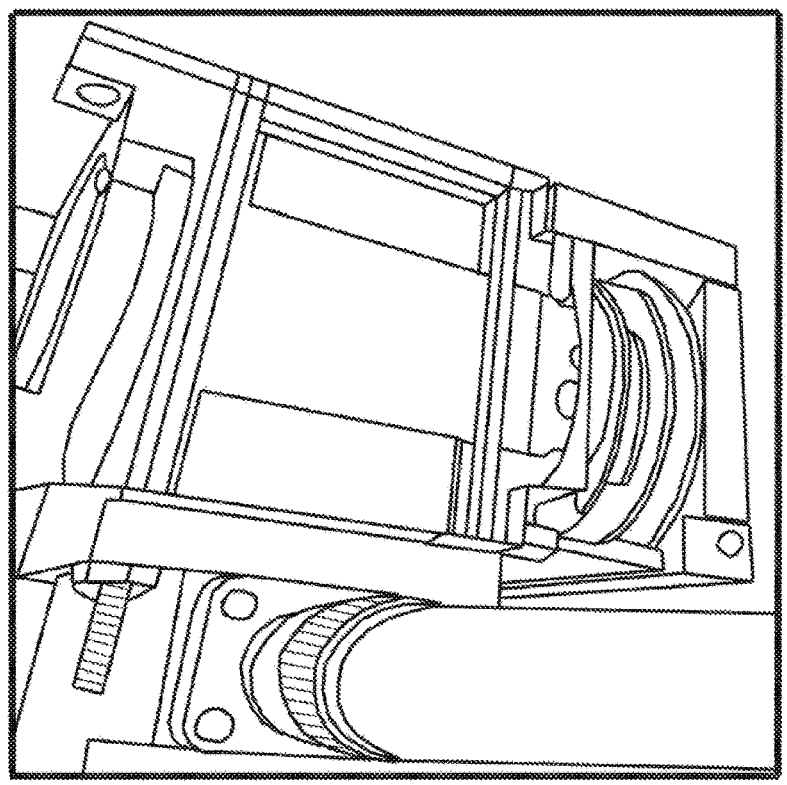
FIG. 15B is a side view.
Figure 15A:
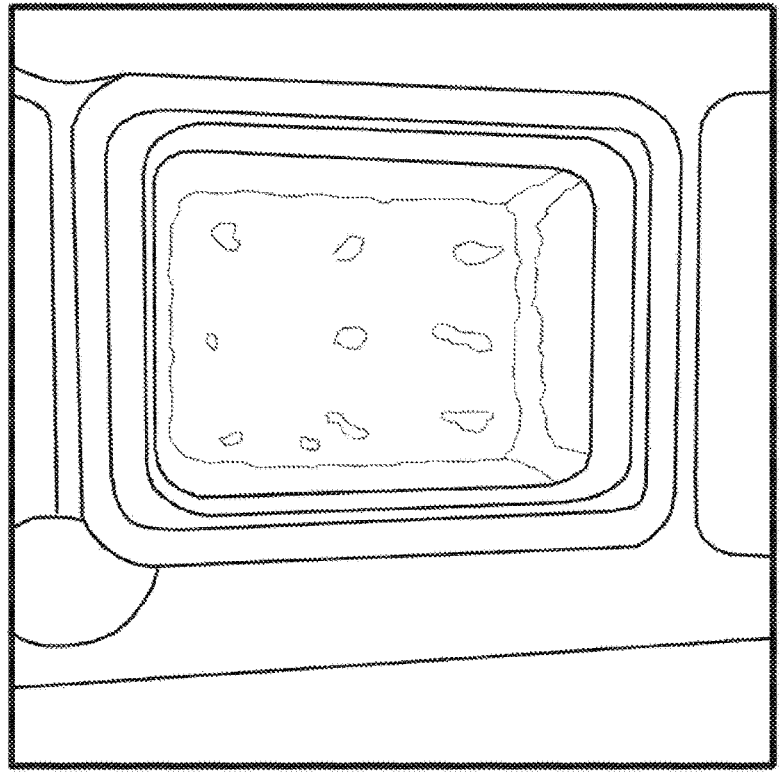
FIG. 15A is a front view photograph of a working 1 inch by 1 inch separator system using a 1 inch by 1 inch crystal driven to a (3,3) mode with a yeast mixture.

FIG. 15A is a photograph of a working 1 inch by 1 inch separator system using a 1 inch by 1 inch crystal driven to a 3×3 mode with a yeast mixture at a frequency of 2 MHz and a flow rate of 30 mL/min. This is a front view of the system, and shows nine trapping lines created by the lateral radiation forces of the multi-dimensional acoustic standing wave. FIG. 15B is a side view of the system, and shows that the trapping lines span the entire width of the acoustic chamber (i.e., between the transducer to the reflector). The system was operated continuously at near 90% clarification for a 1.5% yeast mixture with a packed cell mass of >50% in the concentrated cell stream.

Figure 16:
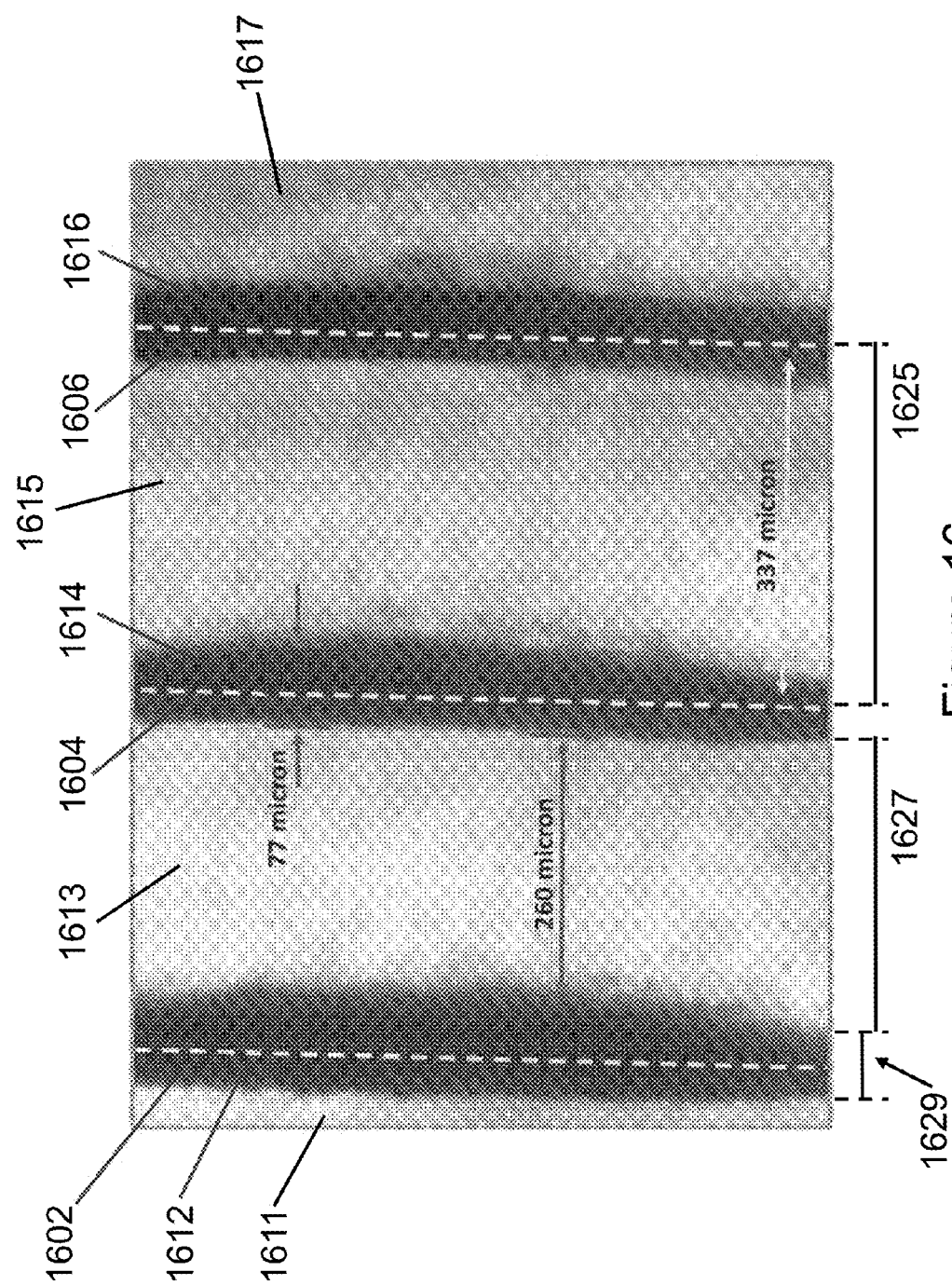
FIG. 16 is a screenshot of a video of a trapping line, showing yeast particle clusters parallel to the direction of flow (direction of flow is upward in screenshot), and clear channels of fluid between the clusters.

In FIG. 16, a 1 inch by 1 inch acoustic chamber was used with a fluid feed rate of 15 ml/minute (peristaltic). The ultrasonic transducer(s) was operated at a frequency of 2.23 MHz and ~7 W power to form multi-dimensional acoustic standing waves, and the fluid was a 3% yeast solution. FIG. 16 is a 200× magnification of the trapping that occurred, showing part of one trapping line with particle clusters that have a height of 260 microns separated from other particle clusters by a distance of approximately 77 microns, for a total of 337 microns. If the speed of sound is 1,484 m/s, the expected half wavelength at the operated frequency is 333 microns. As seen here, as the particles form clusters (260 microns in height), channels of clear fluid are formed between the clusters (77 microns in height). The dimensions of the particle clusters and the fluid channels can be controlled, thereby allowing for improved aggregation and separation of the particles. When the clusters in this example fall out of the trapping line, the clear fluid in the channels between clusters also falls. This response occurs because there is less viscous resistance for the fluid to go around the clusters than through these narrow channels between the clusters as they fall.

Figure 18:
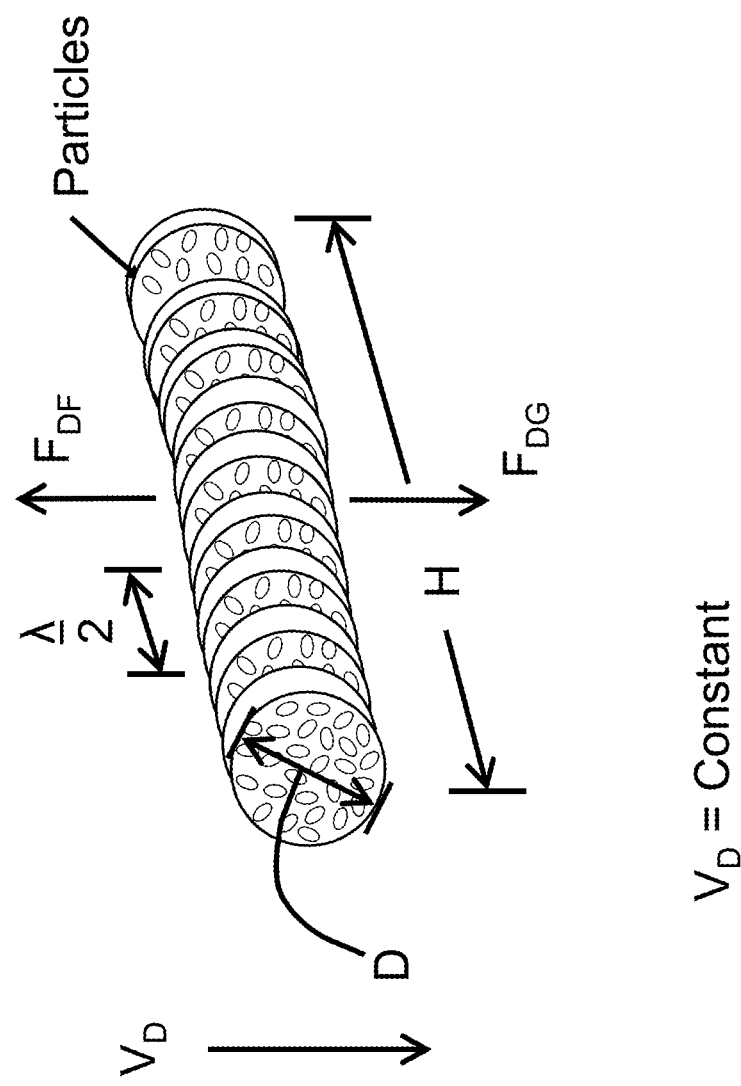
FIG. 18 is a diagram showing the cluster terminal velocity based upon the cluster drag and gravitational forces.

FIG. 18 is an illustration of a portion of a trapping line resulting from the application of a multi-dimensional acoustic standing wave. As seen here, the particle clusters are in the shape of cylindrical disks, or "hockey pucks", with a diameter D, a height that is orthogonal to the diameter, and a distance of λ/2 between their centers. The trapping line has a height H, and experiences several forces. $F_{DF}$ is the fluid draft force (i.e. the flow of fluid is in the upwards direction). $F_{DG}$ is the gravity drag force downwards. Not shown is the acoustic radiation forces, which may be axial (in the H direction) and lateral (transverse to the H direction). $V_D$ is the terminal velocity or cluster drop velocity.

The acoustophoretic devices disclosed herein generate the trapping lines and particulate clusters seen in FIG. 16 and FIG. 18. As explained herein, a multi-dimensional acoustic standing wave having a lateral radiation force and an axial radiation force that are of the same order of magnitude can be generated in the acoustic chamber of the acoustophoresis devices disclosed herein using a single transducer-reflector pair (or two opposing transducers). The acoustic standing wave can continuously trap particles in nodal trapping lines that are transverse to the direction of the standing wave. The shape and/or size of the trapped particle clusters in the nodal trapping lines can be controlled via the operating parameters of the transducer, such as by controlling the frequency, phase or amplitude of the transducer drive signal. The multi-dimensional acoustic standing waves can continuously trap particulates in vertically-staggered nodal trapping lines that are aligned in the direction of the acoustic wave by action of the lateral radiation force. This continuous trapping causes the particulates to cluster, agglomerate, aggregate, clump, or coalesce together into particulate clusters. It is noted that the ultrasonic transducer initially generates nodal planes, until the lateral forces build up enough to create the multi-dimensional acoustic standing wave. The dimensions of the nodal planes and the fluid channels therebetween can also be controlled as described above and further herein.

FIG. 16 shows a number of particulate clusters separated by fluid channels. Each particulate cluster can be generated from particulates that are initially clustered in a nodal plane via axial acoustic forces provided by operation of the transducer. The discussion provided herein with regard to particulate clusters is thus applicable to particulates formed into nodal planes. FIG. 16 illustrates a magnified view of a nodal trapping line showing a first particulate cluster 1611, a second particulate cluster 1613, a third particulate cluster 1615, and a fourth particulate cluster 1617. Adjacent particulate clusters in the nodal trapping line are separated by a fluid channel running therebetween. Put another way, each particulate cluster is generally bordered by two fluid channels, or each illustrated fluid channel is generally bordered by two particulate clusters. For example, as shown in FIG. 16, the second particulate cluster 1613 is bordered by a first fluid channel 1602 along its left side and a second fluid channel 1604 along its right side. Similarly, the third particulate cluster 1615 is bordered by the second fluid channel of fluid 1604 along its left side and a third fluid channel 1606 along its right side. The second fluid channel 1604 is bordered by second particulate cluster 1613 and third particulate cluster 1615.

In FIG. 16, the centers of each fluid channel are indicated with a dotted line 1612, 1614, 1616. The distance between these dotted lines indicates a half-wavelength at the frequency at which the acoustophoretic device is operated, and is marked with reference numeral 1625, and is referred to as a height. The height of the particulate cluster is indicated with reference numeral 1627, and the height of the fluid channel is indicated with reference numeral 1629. It is expected in some implementations that these heights will be regular, i.e. the heights of the particulate clusters will all be substantially the same, and the heights of the fluid channels will all be substantially the same. The term "substantially" refers to plus or minus 5% of the indicated number.

Using the acoustophoretic devices disclosed herein, the relative sizes of the particulate clusters and the fluid channels within the nodal trapping lines can be varied as desired. Put another way, the frequency of the voltage signal (i.e. the frequency of the multi-dimensional acoustic standing wave) can be selectively tuned to obtain desirable characteristics.

The height 1625 (i.e. half-wavelength) can be from about 200 micrometers to about 1700 micrometers. In more particular embodiments, the height 1625 can be from about 300 micrometers to about 850 micrometers.

The height 1627 of the particulate clusters can be from about 150 micrometers to about 1200 micrometers. In more particular embodiments, the height 1627 can be from about 200 micrometers to about 600 micrometers.

The height 1629 of the fluid channels can be from about 50 micrometers to about 500 micrometers. In more particular embodiments, the height 1629 can be from about 100 micrometers to about 250 micrometers.

It is specifically contemplated that, in certain embodiments, the ratio of the height of the particulate clusters to the height of the fluid channels can be from about 1:1 to about 5:1, and in more specific embodiments from about 3:1 to about 5:1. In other words, the particulate clusters desirably have a greater height than the fluid channels.

The system depicted in FIG. 1 includes an acoustophoretic device that can be implemented to achieve the results illustrated in FIG. 16. The example acoustophoretic device uses a 3 inch×3 inch×3 inch acoustic chamber with four 1.5 inch by 1.5 inch 2 MHz PZT-8 transducers. The system of FIG. 1 was operated continuously at near 90% clarification for a 1.5% yeast mixture with flowrates of about 270 ml/min, and a packed cell mass of >50% in the concentrated cell stream. The same system has been operated effectively for the clarification of protein from a CHO/protein cell mixture. Such applications are important in the advancement of the biopharmaceutical industry.

At low Reynolds numbers, the drag is a result primarily of shear forces, or the flow is fully viscous. Viscous flow prefers to move in planes, or laminar layers. Any three dimensionality tends to increase drag. Thus, at low Reynolds numbers, the following equations present drag coefficients (CD) as a function of particle Reynolds numbers (Re):

$$\text{Sphere: } C_D = \frac{24}{Re}(1 + 0.15 Re^{0.678}) \text{ for } 0 < Re \leq 2 \times 10^5$$

$$\text{Cylinder: } C_D \approx 1 + 10 Re^{-\frac{2}{3}} \text{ for } 1 < Re \leq 2 \times 10^5$$

The equations show that the drag coefficient of a cylinder is lower than a sphere at Reynolds numbers less than ten. Furthermore, a cylinder can carry significantly more particles for a given projected area. This means a cylindrical particle cluster will have higher gravity forces and lower resistance drag than a spherical particle cluster at low Reynolds numbers. Therefore, a cylindrical particle cluster will drop out or rise out of the fluid faster than other shapes. As a result, it is important to choose an electrical signal drive frequency for the acoustophoretic separation system that gives the best cylindrical cluster generation for drop out or rise out.

Figure 17:
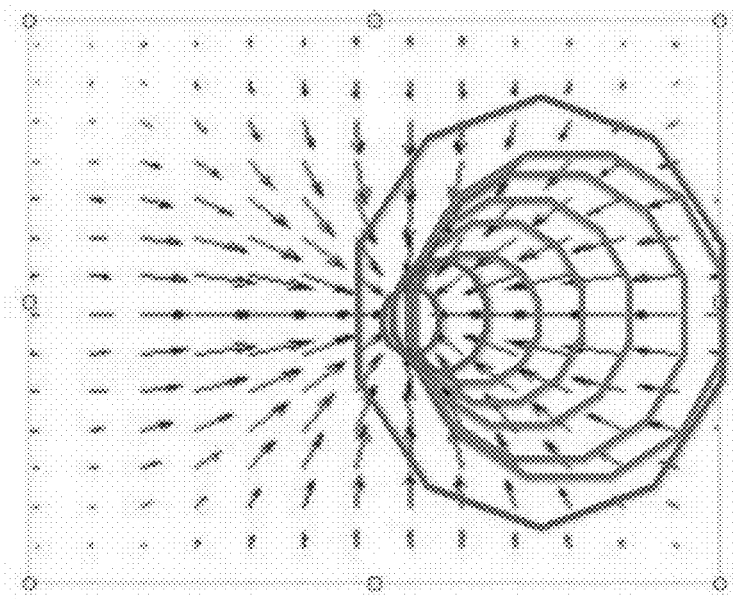
FIG. 17 is a schematic of the lateral forces near one trapping line, with several different particle cluster diameters shown.

FIG. 17 shows the effect of the lateral force variation on particle clustering. This figure shows the predicted lateral forces (based on a COMSOL simulation) near one node or trapping line, along with several different particle cluster diameters. The arrow lengths represent the lateral radiation force magnitude. At the center of the node, there is no force, and the other lateral forces will drive all the particles towards this location. This would be the cluster location if there were no other forces. Three different forces act on any cluster: FL, FD, and FG. FL represents the sum of all the lateral acoustic radiation particle forces. FD is the fluid drag force of the cylindrical cluster. FG is the force of gravity pulling down on the cluster particles. The drag force FD on a particle cluster will be an order of magnitude smaller than the lateral radiation force FL or gravity force FG on the cylindrical clusters. The gravity force is offset by the lateral radiation force. The cluster moves down slightly to have a net upwards lateral radiation force (lateral direction is the flow direction) to offset the gravity force. In other words, if each force vector inside a cluster represents a force on a particle in the cluster, the net force on the cylindrical cluster is the sum of all the particle forces. The particle forces get larger as the cluster moves downwards. Therefore, the net radiation force (or the sum of all the up vectors) on the cluster increases as the cluster moves down.

The upward forces on the enclosed particles vary from zero at the node to a maximum value at the anti-node. The total lateral radiation force per unit volume decreases with cluster size; it does not stay constant. The decrease in total lateral radiation force per unit volume is consistent with the decrease in drag force per unit particle as the cluster size increases. As the cluster diameter increases, the cluster includes particles with radiation forces acting in the downward direction.

The density of the particles and the volume of the cluster determines the gravity force, assuming the particle concentration of the cluster is constant. With this assumption, gravity force per unit volume is constant as a particle cluster increases in size. Therefore, the lateral radiation forces move the particles in the planes towards the nodes in clusters. These clusters will locate below the nodes at an equilibrium position where the radiation forces can hold the cluster in suspension as it grows. As the clusters grow in size, the net lateral force per unit volume decreases while the net gravity force per unit size remains constant. The center of the cluster continues to shift down with cluster size increase until it is at the maximum lateral force location. At some cluster size, the gravity force dominates, and the cluster falls out of suspension. When the cluster falls out of suspension, the cycle can repeat and new clusters are formed, thereby permitting the system to continuously operate.

The drop out cluster diameter is determined by the forces acting on the particles in the clusters. The lateral radiation force is a function of the lateral acoustic pressure field generated by the multi-dimensional acoustic standing wave. There are several formulations for radiation pressure experienced by a sphere inside an acoustic field. The most widely used formulation for acoustic radiation forces is by Gork'ov, where the primary acoustic radiation force $F_A$ is defined as a function of a field potential U, $F_A = -\nabla(U)$, where the field potential U is defined as $$U = V_0 \left[ \frac{\langle p^2(x,y,t) \rangle}{2 \rho_f c_f^2} f_1 - \frac{3 \rho_f \langle v^2(x,y,t) \rangle}{4} f_2 \right]$$

and $f_1$ and $f_2$ are the monopole and dipole contributions defined by $$f_1 = 1 - \frac{1}{\Lambda \sigma^2}$$

$$f_2 = \frac{2(\Lambda - 1)}{2\Lambda + 1},$$

where $$\sigma = \frac{c_p}{c_f}$$

$$\Lambda = \frac{\rho_p}{\rho_f}$$

$$\beta_f = \frac{1}{\rho_f c_f^2}$$

where p is the acoustic pressure, u is the fluid particle velocity, $\Lambda$ is the ratio of cell density $\rho_p$ to fluid density $\rho_f$, $\sigma$ is the ratio of cell sound speed $c_p$ to fluid sound speed $c_f$, $V_o$ is the volume of the cell, and <> indicates time averaging over the period of the wave.

Gork'ov's model is for a single particle in a standing wave and is limited to particle sizes that are small with respect to the wavelength of the sound fields in the fluid and the particle. It also does not take into account the effect of viscosity of the fluid and the particle on the radiation force. As a result, this model is not used for the macro-scale ultrasonic separators discussed herein since particle clusters can grow quite large. A more complex and complete model for acoustic radiation forces that is not limited by particle size is therefore used. The models that are implemented are based on the theoretical work of Yurii Ilinskii and Evgenia Zabolotskaya as described in AIP Conference Proceedings, Vol. 1474-1, pp. 255-258 (2012). These models also include the effect of fluid and particle viscosity, and therefore are a more accurate calculation of the acoustic radiation force.

The cluster terminal velocity is obtained by equating the cluster drag force ($F_{DF}$) and gravity drag force ($F_{DG}$). The resulting equations for a cylindrical cluster are presented in FIG. 19. In FIG. 19, $C_D$ is the drag coefficient of the cylinder; $\rho_p$ is the particle density; $\rho_f$ is the fluid density; g is the gravity of Earth, i.e. ~9.8 m/s$^2$; and $\phi$ is the percentage of the volume of the cluster that is occupied by particles (volume fraction of the cluster).

Figure 20:
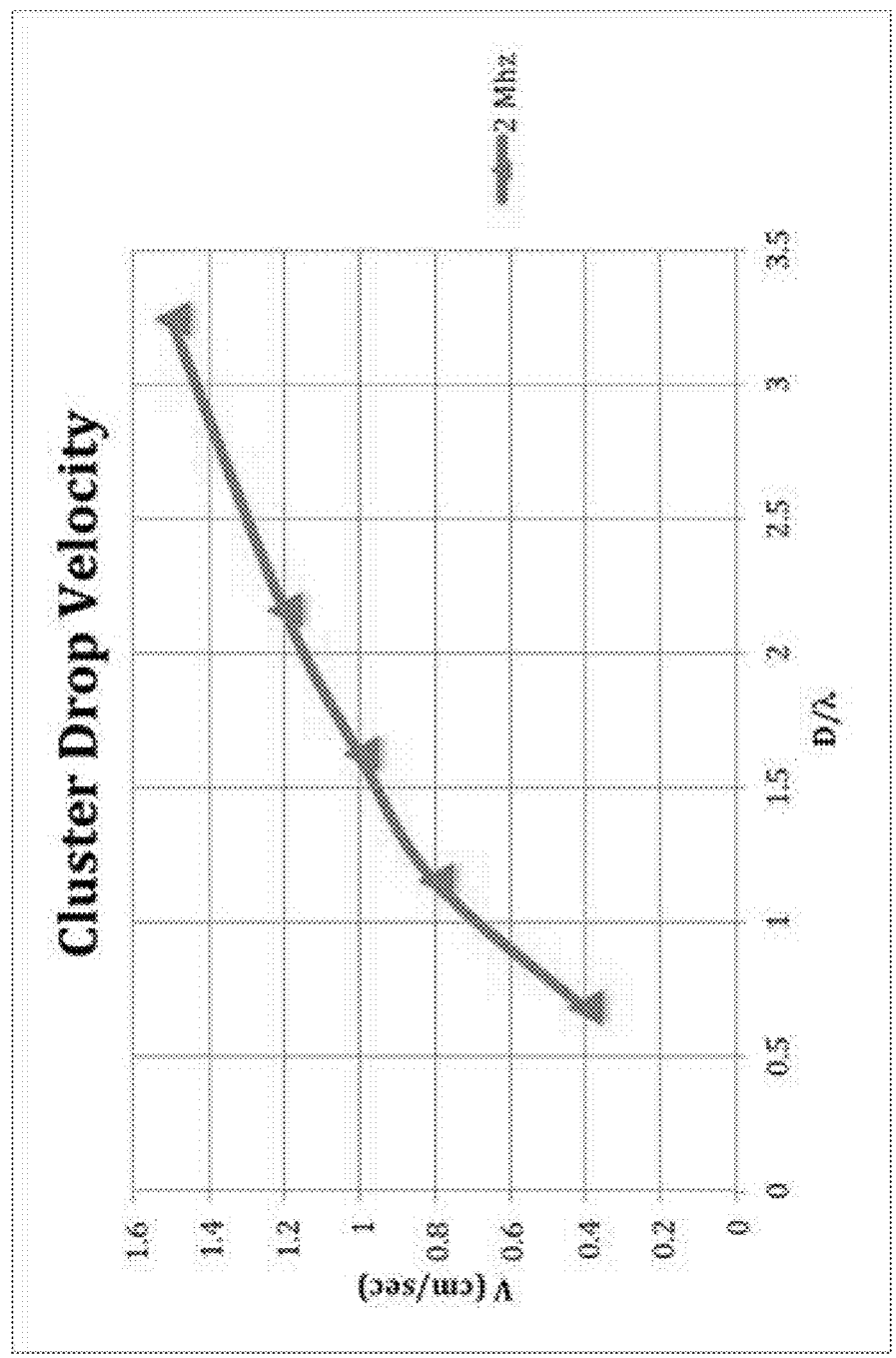
FIG. 20 is a graph showing the predicted cylindrical cluster drop velocity versus non-dimensional cluster diameter (D/λ) where lambda (λ) is the axial wavelength of the standing wave. The y-axis runs from 0 to 1.6 in intervals of 0.2. The x-axis runs from 0 to 3.5 in intervals of 0.5.
Figure 21:
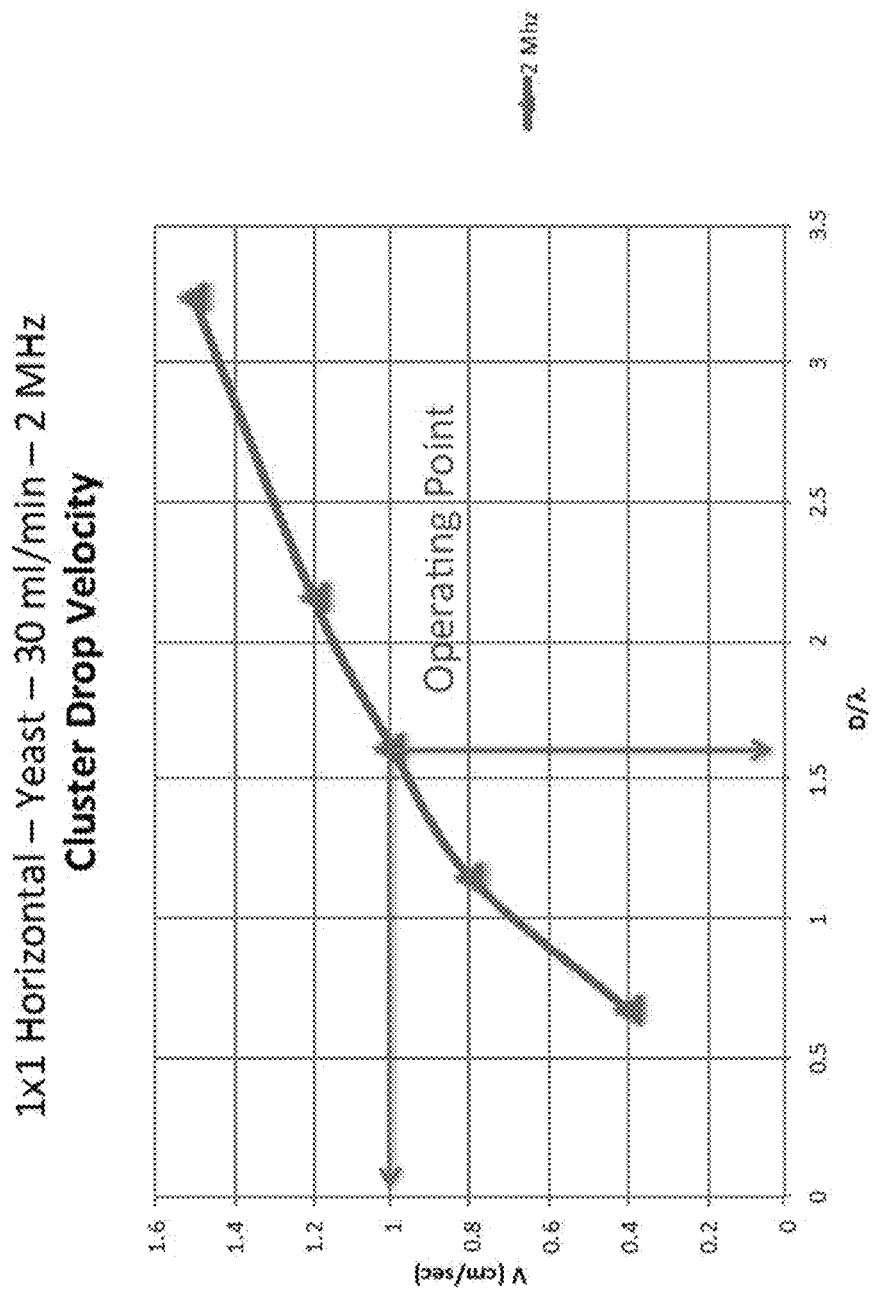
FIG. 21 is the graph of FIG. 20, showing the predicted cluster drop velocity for a cluster diameter D/λ=1.62 is approximately 1 cm/sec or 0.01 m/sec.
Figure 22:
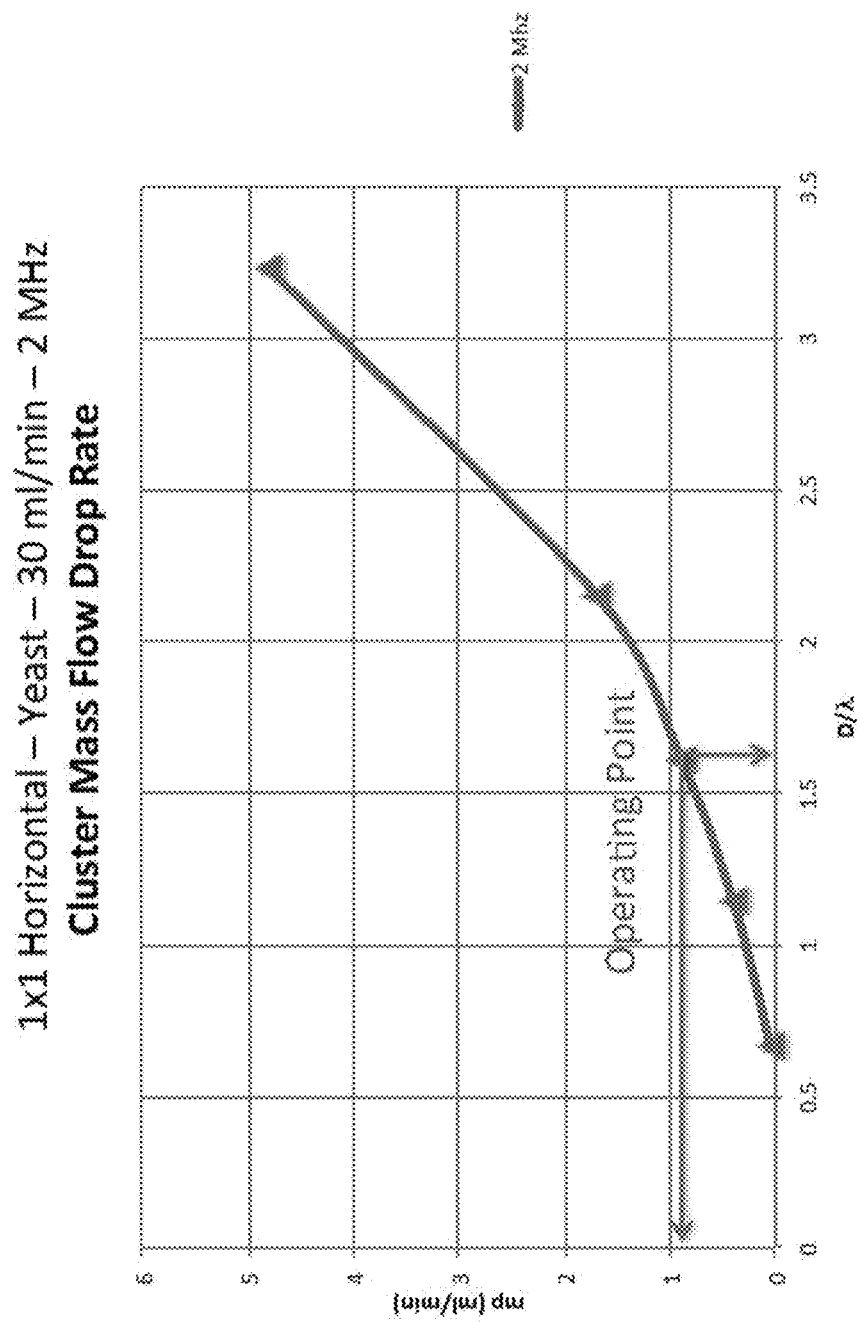
FIG. 22 is a graph showing particle collection flowrate in mL/min versus non-dimensional cluster diameter (D/λ) for the system of FIG. 20. The y-axis runs from 0 to 6 in intervals of 1. The x-axis runs from 0 to 3.5 in intervals of 0.5.
Figure 23:
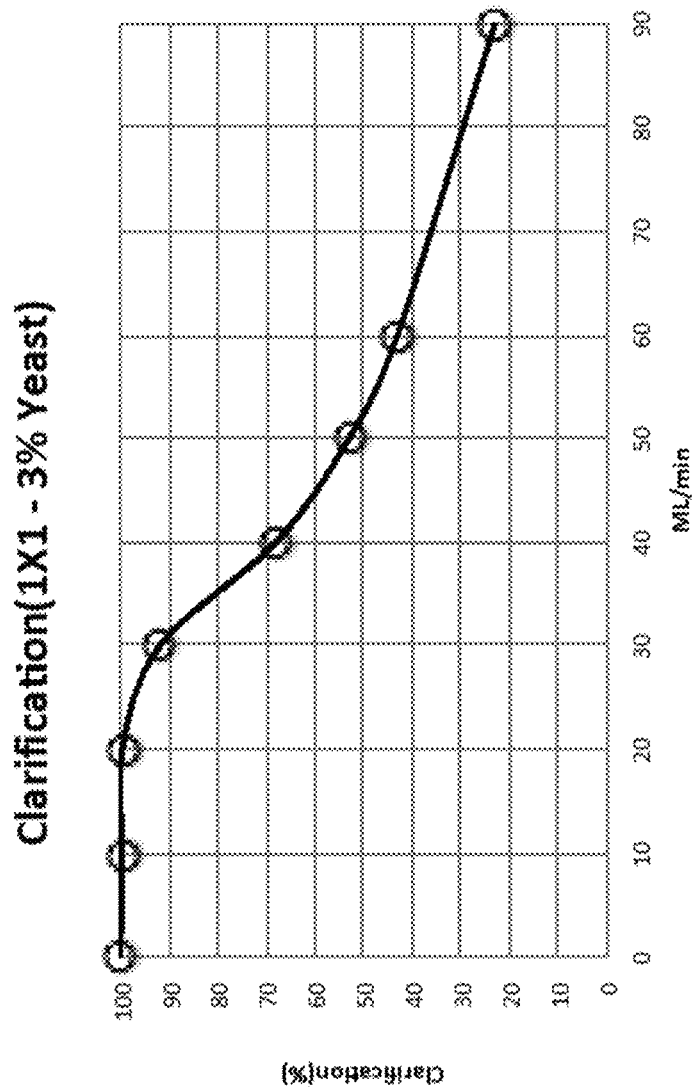
FIG. 23 is a graph of clarification performance (%) versus cluster particle flowrate (mL/min) for the system of FIG. 20. The y-axis runs from 0 to 100 in intervals of 10. The x-axis runs from 0 to 90 in intervals of 10.
Figure 24:
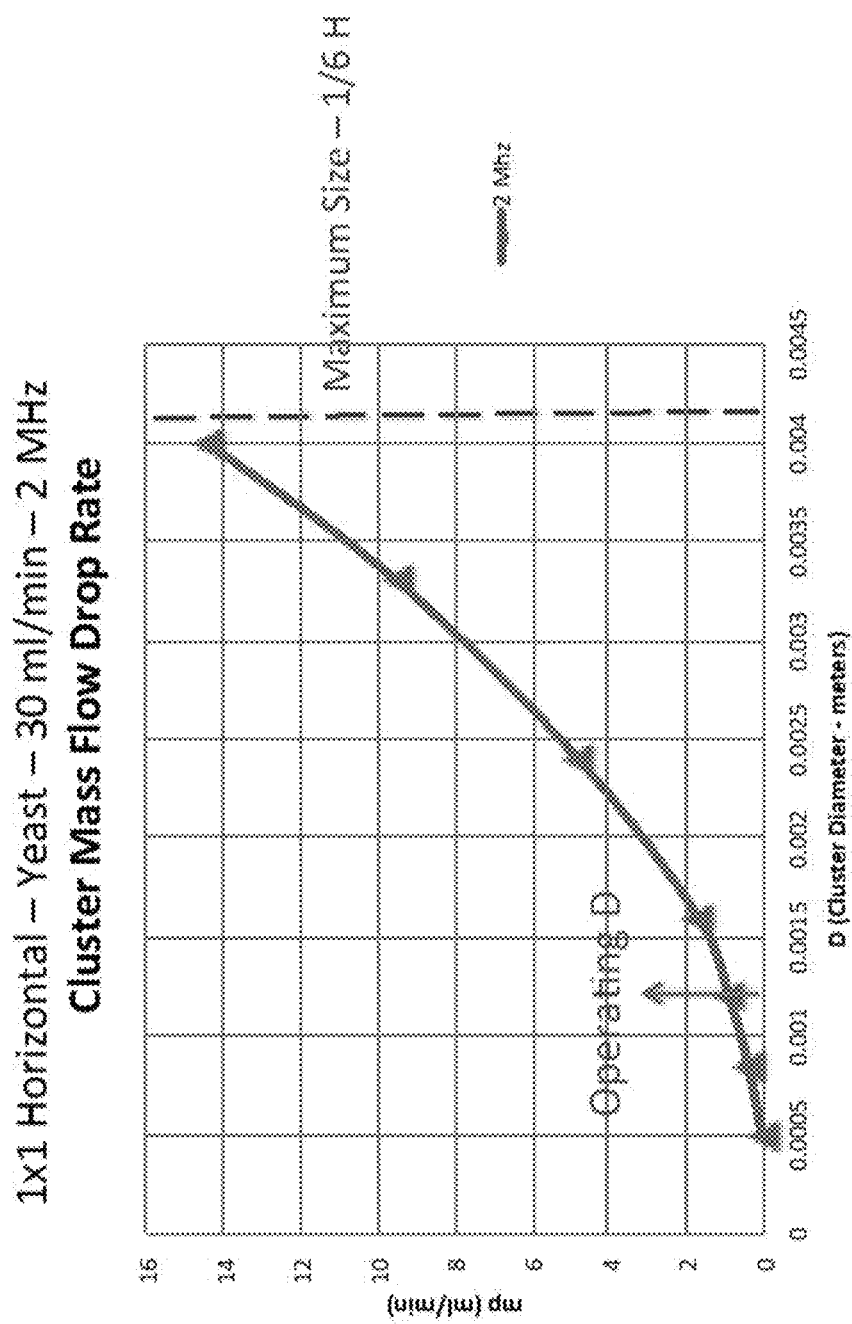
FIG. 24 is a graph showing predicted system particle collection potential (mL/min) versus non-dimensional cluster diameter (D/λ) for the system of FIG. 20. The y-axis runs from 0 to 16 in intervals of 2. The x-axis runs from 0 to 0.0045 in intervals of 0.0005.
Figure 25:
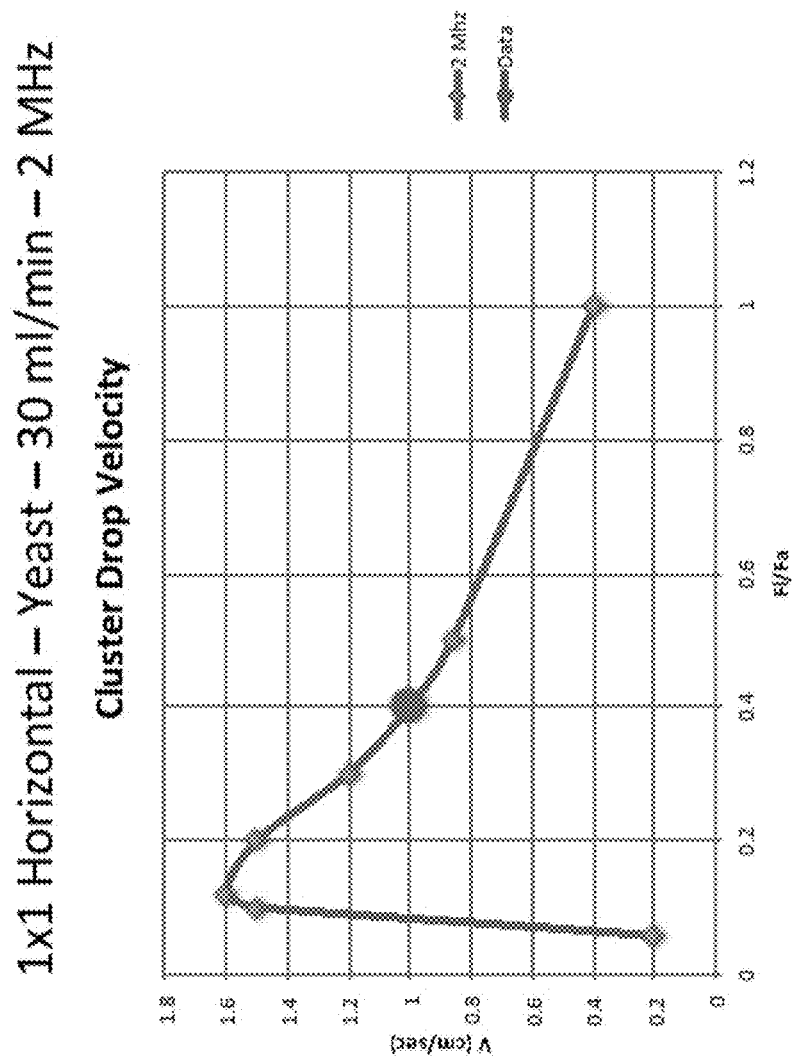
FIG. 25 is a graph showing the predicted cluster drop velocity (cm/sec) versus lateral-to-axial radiation force ratio ($F_L/F_A$) for the system of FIG. 20. The y-axis runs from 0 to 1.6 in intervals of 0.2. The x-axis runs from 0 to 1.2 in intervals of 0.2.

The equations can be solved to obtain estimated cluster drop velocity and collector effectiveness. FIG. 20 presents the predicted cylindrical cluster drop velocity as a function of non-dimensional cluster diameter (D/λ) where lambda (λ) is the axial wavelength of the standing wave (here 2 MHz). These results predict a significant increase in cluster drop out velocity with increase in cluster size. Larger clusters and higher drop velocities will result in more efficient particle collection. This means the system will separate and collect with higher concentrations, or at higher flowrates with the same concentration.

A functional representation of the important non-dimensional parameters of the physical process can be obtained as follows.

$$\frac{D}{\lambda} = f\left(R_{eD}, \frac{\rho_p}{\rho_f}, S, \frac{F_L}{F_A}, \frac{P}{\rho c^2}, \frac{h}{d}, \frac{P}{\rho V^2}\right)$$

where $R_{eD}$ is the Reynolds number; S is the acoustic contrast factor; $F_L$ is the lateral radiation force component; $F_A$ is the axial radiation force component; P is the acoustic pressure; V is the flow-through velocity of the particle/fluid mixture; and the other variables are as described above.

Non-dimensional parameters provide fewer and more universal variables for a given physical phenomenon. The cluster drop out size divided by the primary acoustic standing wavelength is seen to be a function of Reynolds number, density ratio, contrast factor, lateral to axial particle radiation force, acoustic pressure over speed of sound dynamic pressure, chamber dimension over particle diameter and acoustic pressure over fluid dynamic pressure. Reynolds number variations with different system operations are assumed small. For a fixed system, same mixture, same power input, and the same flowrate, the non-dimensional cluster drop out diameter can be determined experimentally.

The test illustrated in FIG. 15A was visually measured to determine the accuracy of the derived equations. Visual measurements of FIG. 15A indicated that D~0.0012 meters; V~0.01 m/s drop velocity; and λ~0.00074 meter wavelength, for a D/λ~1.62. According to the equations, with D/λ=1.62, the cylinder drop velocity is approximately 0.01 m/s, as indicated in FIG. 21. Also, the cylinder cluster diameter D=0.0012 meters, and the Reynolds number ReD=15, which agrees with the experimentally measured values.

FIG. 22 is a graph of particle collection flowrate in ml/min versus cluster drop out diameter. These values are obtained assuming only the three bottom cylindrical clusters dropped, which assumption is made because all other clusters are directly above the bottom row of clusters. That is, as the top cluster drops, it hits the middle cluster location, which drops and hits the bottom cluster location, and then drop out of the chamber and is collected. The same analysis can be carried out for higher order modes which give more number of clusters.

FIG. 23 is a graph showing the clarification performance of the system versus the cluster particle flowrate, using the cluster particle flowrate from FIG. 22. Again, the agreement with measured efficiency of the 1×1 system with yeast follows the analytical model. The model predicts good clarification up to a system flowrate of 30 mL/min. This prediction is consistent with the measured yeast performance of the acoustophoretic separator.

FIG. 24 is a graph showing predicted system particle collection potential versus cluster diameter. These results show that cluster size is key to collection improvement. A larger cluster size allows faster dropout and faster clarification. Moreover, cluster size can be increased by lowering the standing wave frequency. This increases lambda, and therefore increases cluster diameter, D. It can also be shown that cluster size can be increased by decreasing the lateral acoustic radiation forces by operating the crystal using an operating frequency that has a lower multi-mode amplitude and a higher planar mode amplitude.

Next, an analytical model linking lateral-to-axial radiation force ratio (X) to particle cluster size (D) can be developed by assuming a constant pressure through the cluster:

$$\rho_A = \rho_F$$

(i.e., the dense mixture in the fluid acts as a stationary fluid), and $$\rho_A = \frac{F_A}{\frac{\pi D^2}{4}} \text{ and } \rho_F = \frac{xF_A}{\frac{D\lambda}{2}}$$

where the dominant forces generating the pressure are the lateral and axial forces on the particles in the cluster. Solving the above equations, the expression can be reduced to:

$$D/\lambda = 0.64/x$$

This expression indicates that the cluster diameter increases inversely with the lateral to axial radiation force ratio. If the axial radiation force is fixed, the particle cluster diameter increases with a decrease in the lateral radiation force. The effect is similar to pushing inwards on a balloon, where the balloon dimension will be larger perpendicular to the direction in which the push is applied.

FIG. 25 is a graph showing the predicted cluster drop velocity versus the lateral-to-axial radiation force ratio. The velocity is seen to increase dramatically with lower lateral forces, with a peak when $F_L/F_A$ is between 0.1 and 0.2. This is due to larger cluster diameters. The drop off in velocity at extremely low lateral forces is a result of the large cluster diameters interfering with each other and retarding collection. As the particle clusters fall, there may be room between them allowing clear fluid to flow upward (satisfying continuity). At x=0, the clusters would theoretically have infinite diameter, i.e. be a plane of particles rather than a cluster. The $F_L/F_A$ ratio can be controlled by controlling the drive signal applied to the transducer where, for example, different operational modes can be selected at different frequencies.

Particle drop out occurs when the cluster size reduces the acoustic radiation force per unit volume below the constant gravity force per unit volume of the cluster. The change in acoustic radiation force per unit volume of a cluster is directly determined by the spatial varying radiation force field. The gravity force field is constant. The size of the particle clusters formed is therefore a function of the lateral radiation force generated on the particle clusters and the density of the particles. The lateral radiation force is controllable via control of the transducer. Lower density particles, for the same radiation force values, results in larger clusters. The cluster sizes in the tests discussed above have generally used yeast. Macro-scale, ultrasonic separators are proposed for separating out various particle or cells from a mixture. Separating Chinese Hamster Ovary (CHO) cells from its protein solution is one of the more important proposed applications. CHO cells have slightly different radiation force values than yeast, but have a much lower density. Therefore, the particle cluster size for CHO to drop out is dramatically larger than for yeast. CHO cluster sizes can even be large enough for particle clusters to vertically attach and allow high concentration mixture to flow down to the collector.

Figure 26:
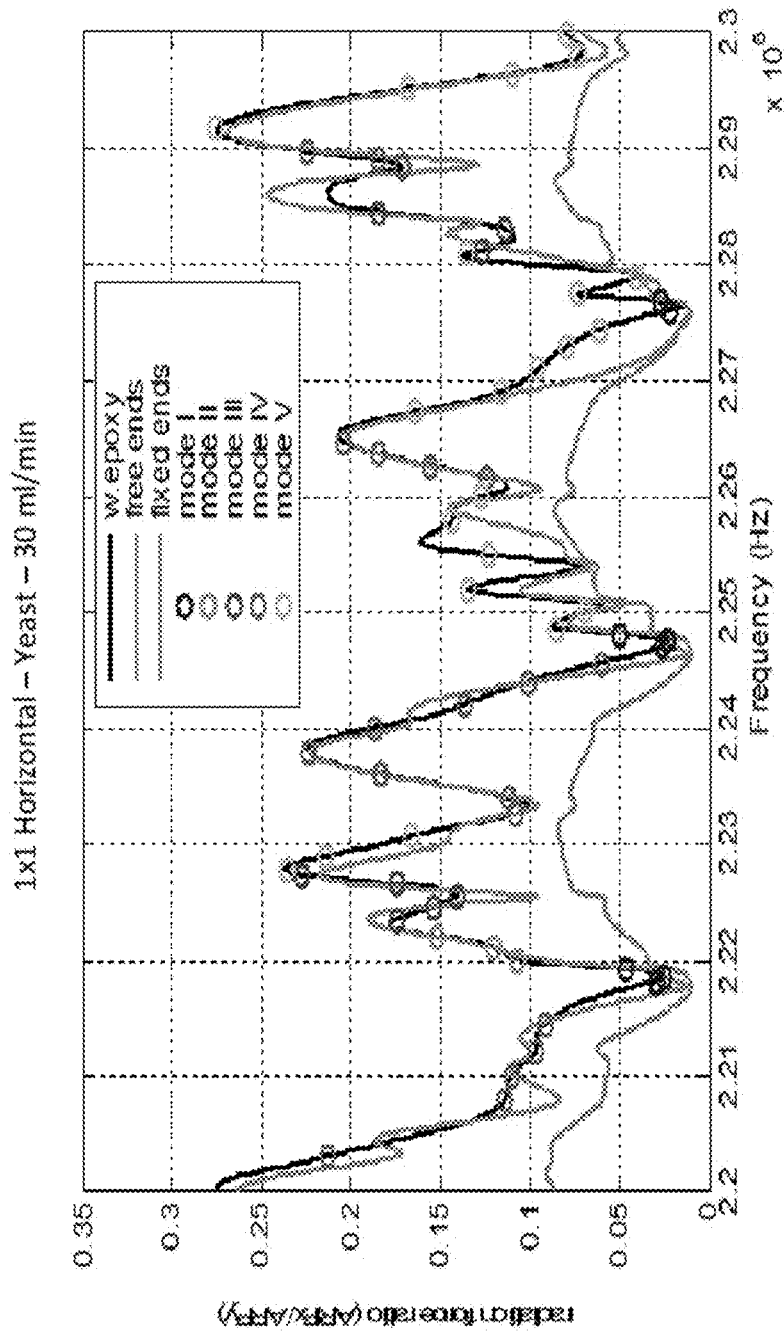
FIG. 26 is a COMSOL simulation showing the lateral-to-axial radiation force ratio ($F_L/F_A$) versus frequency (MHz) for many different operating modes of a crystal, including with different structures. The y-axis runs from 0 to 0.35 in intervals of 0.5. The x-axis runs from 2.2 to 2.3 in intervals of 0.01.

The piezoelectric crystals of the transducers described herein can be operated at various modes of response by changing the drive parameters, including frequency, for exciting the crystal. Each operation point has a theoretically infinite number of vibration modes superimposed, where one or more modes are dominant. In practice, multiple vibration modes are present at arbitrary operating points of the transducer, with some modes dominating at a given operating point. FIG. 26 presents COMSOL results for crystal vibration and lateral radiation forces on a typical particle size. The ratio of lateral to axial radiation force is plotted versus operating frequency. Points are labeled on the curve where a specific mode of vibration is dominant. Mode I represents the planar vibration mode of the crystal designed to generate a 2 MHz standing wave in a mixture. Mode III represents the 3×3 mode operation of a 1×1 crystal. These analytical results show that the 3×3 mode can be dominant with different levels of lateral radiation force. More specifically, operating the example system at a frequency of 2.283 MHz generates the lowest lateral force ratio of about 1.11 for a 3×3 mode. This operating point generates the largest cluster size and the best collection operation for the example system. Operating the devices and systems described herein at a frequency for a given configuration that produces a desired 3D mode with the lowest lateral force ratio is desirable to achieve the most efficient separation.

Figure 27:
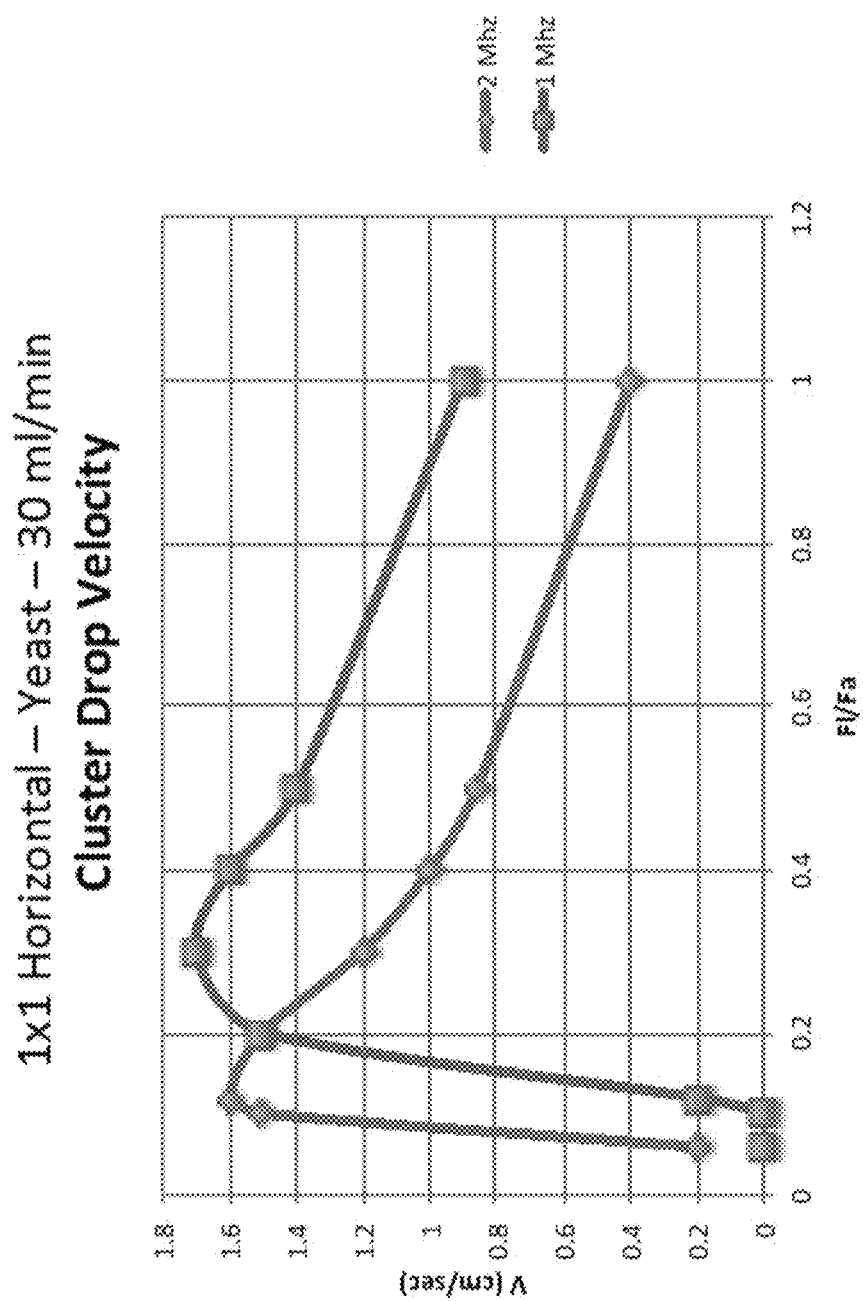
FIG. 27 is a graph showing predicted cluster drop velocity (cm/sec) versus lateral-to-axial radiation force ratio ($F_L/F_A$) for both 1 MHz and 2 MHz frequencies. The y-axis runs from 0 to 1.8 in intervals of 0.2. The x-axis runs from 0 to 1.2 in intervals of 0.2.
Figure 28:
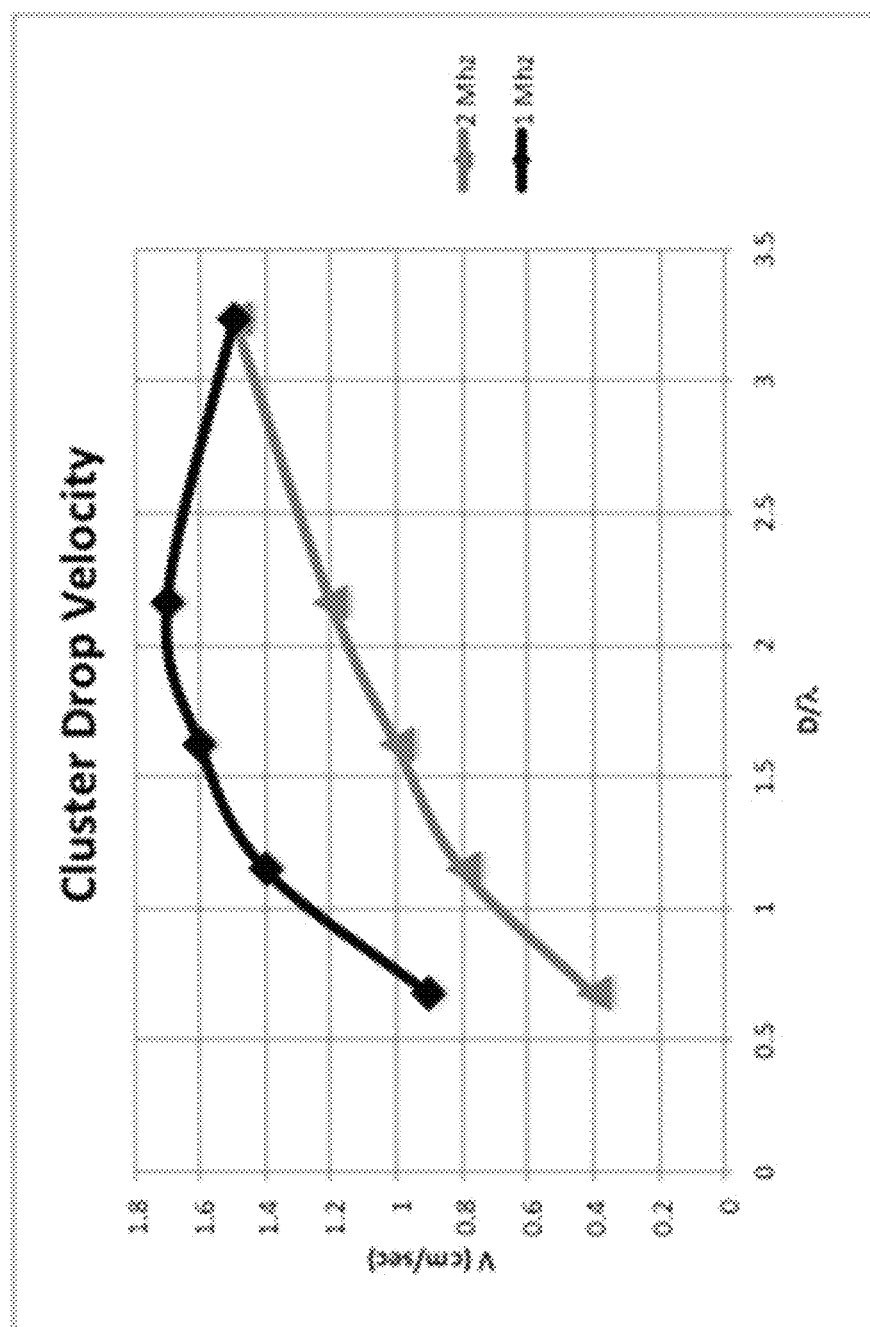
FIG. 28 is a graph plotting the predicted cluster drop velocity (cm/sec) of FIG. 27 versus non-dimensional cluster diameter (D/λ). The y-axis runs from 0 to 1.8 in intervals of 0.2. The x-axis runs from 0 to 3.5 in intervals of 0.5.
Figure 29:
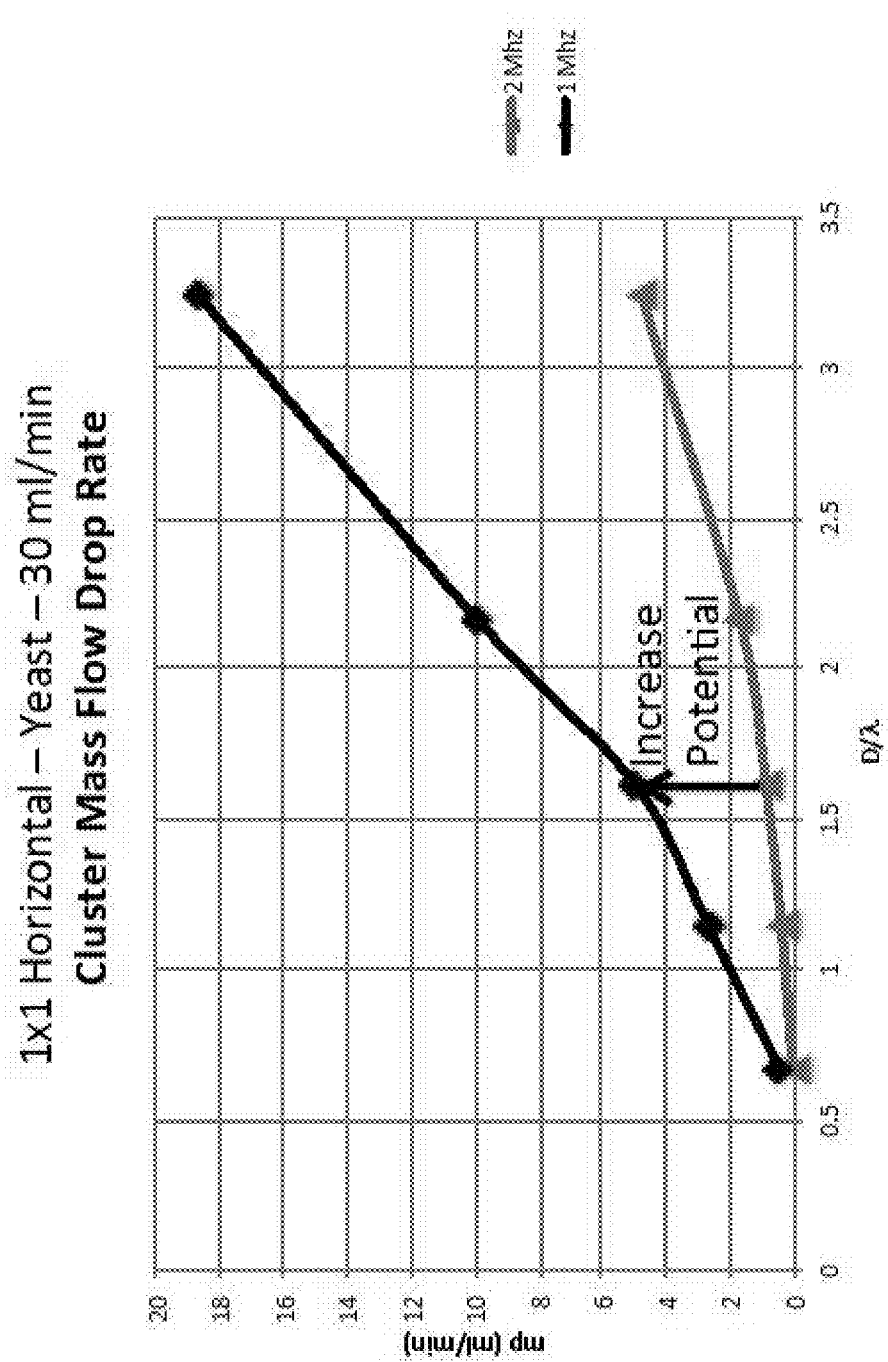
FIG. 29 is a graph showing the particle collection flowrate (mL/min) of FIG. 27 versus non-dimensional cluster diameter (D/λ). The y-axis runs from 0 to 20 in intervals of 2. The x-axis runs from 0 to 3.5 in intervals of 0.5.

Cluster size can also be increased by lowering the standing wave frequency. This reduction in frequency increases lambda, and therefore increases cluster diameter (D). FIG. 27 is a graph of predicted cluster drop velocity versus lateral-to-axial radiation force ratio for both 1 MHz and 2 MHz frequencies. These results show a significant increase in drop out velocity with the lower frequency, 1 MHz operation, with a peak between $F_L/F_A$ of 0.2 to 0.4. The increase in performance with lower frequency is a result of larger cluster diameters at all force ratios with the system operating at 1 MHz. This performance is verified in FIG. 28, which shows the cluster drop velocity versus the non-dimensional cluster diameter, and in FIG. 29, which shows the predicted particle collection rate versus non-dimensional cluster diameter. At a D/λ of 1.62, which represents the measured cluster diameter drop out size for yeast, operation at 1 MHz is seen to increase collection potential five times.

Figure 30:
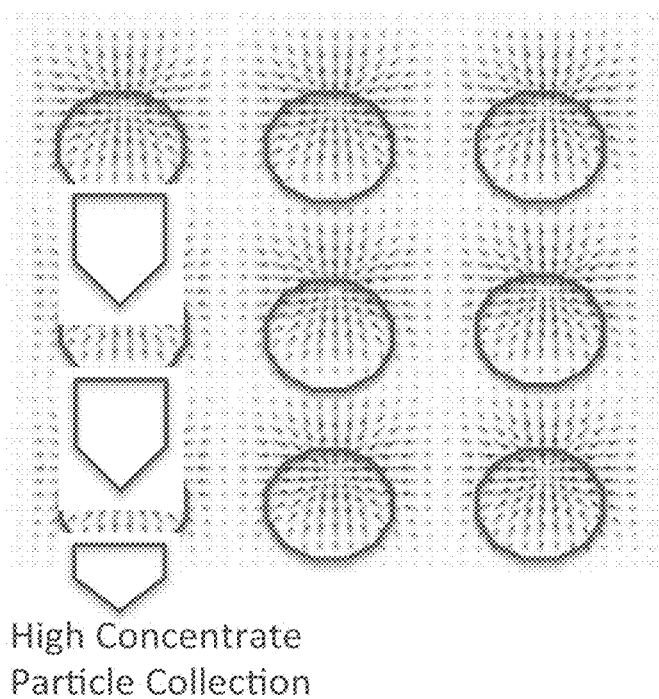
FIG. 30 is an illustration of clusters with large diameters bleeding into clusters below them, resulting in high concentrate particle collection.

At lower frequencies, however, different phenomena begin to occur. It was previously mentioned above with respect to FIG. 16 that when the particle clusters fall, the fluid in the channels between clusters also falls and fluid flows around the clusters rather than through the channels. In the example of FIG. 16, the frequency was 2 MHz. At a lower frequency of 1 MHz, the channels between the clusters doubles in size, so the fluid/particle mixture can flow between clusters. As a result, the particle clusters can grow without falling out. Rather, due to the distribution of the acoustic radiation force and gravity forces, there is a critical size where the cluster boundary intersects the downward particle radiation force region below the cluster (see prior discussion of FIG. 17). Particle clusters in trapping lines at this critical size begin to "bleed" into the trapping lines below them. This phenomena is depicted in FIG. 30. This type of action may also provide a benefit because the particle clusters drop out, not necessarily the fluid between them, which can be considered an increase in the concentration of particles.

Figure 31:
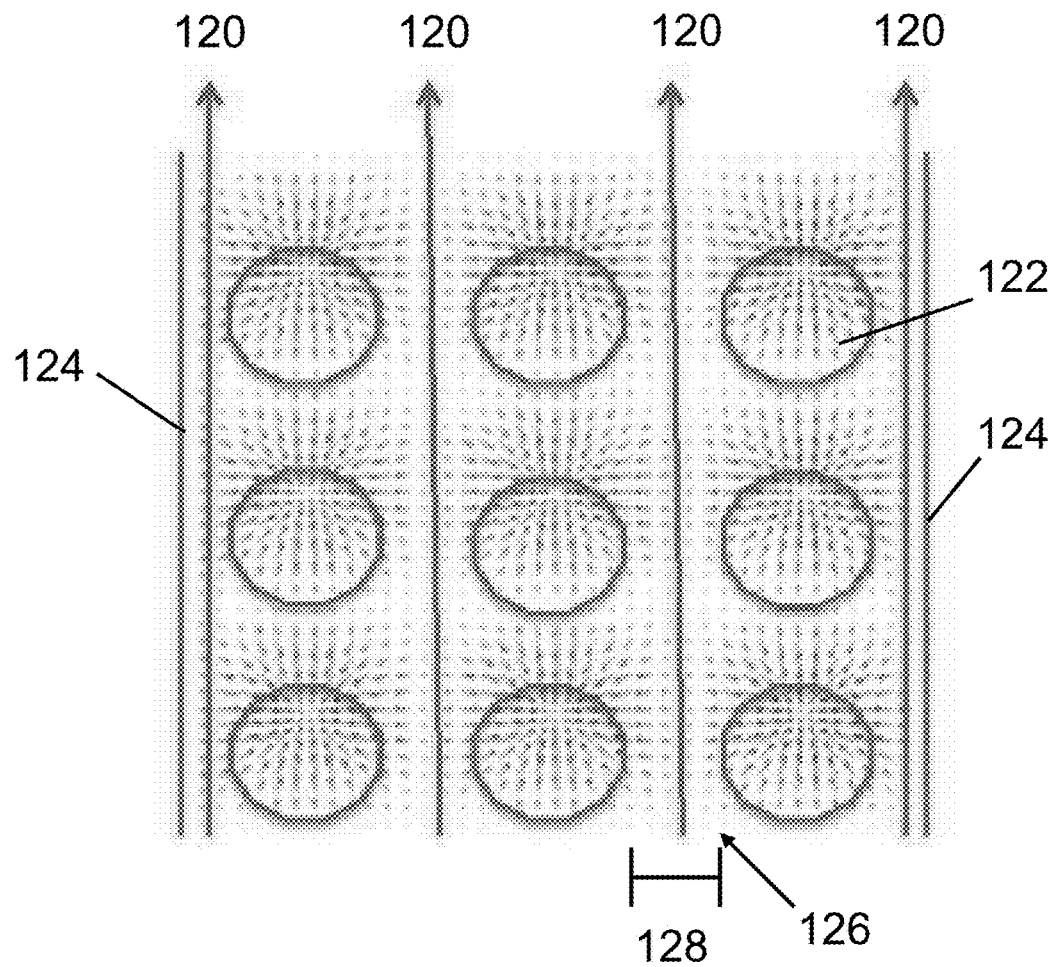
FIG. 31 shows a diagram of nine trapping lines with large channels between them, with the arrows representing leakage pathways in which there is little or no lateral forces.

In addition, it is possible to obtain particle clusters that have large diameters but low density. For example, large diameter clusters can be achieved with CHO cells at a number of different frequencies, including frequencies of 1 MHz and 2 MHz. With larger cluster diameters, the fluid/particle mixture flowing through and around the clusters has a higher velocity, and it becomes possible for the fluid drag force to dominate, such that large particles do not drop out/rise out of the host fluid. This operation is depicted in FIG. 31. In the cross-sectional view of FIG. 31, the fluid/particle mixture flows upward, as indicated by the arrows 120, against gravity, through and around nine circular particle clusters 122 within an acoustic chamber marked by walls 124. The particle clusters indicate the position of the nine trapping lines within the acoustic chamber (see FIG. 14A). As illustrated here, the arrows illustrate fluid flow through relatively straight vertical channels 126 having a cross-sectional area indicated by reference numeral 128. Without being bound by theory, along these "leakage pathways" there is little to no lateral forces, which may permit particles or secondary fluids to pass without being collected.

Figure 32B:
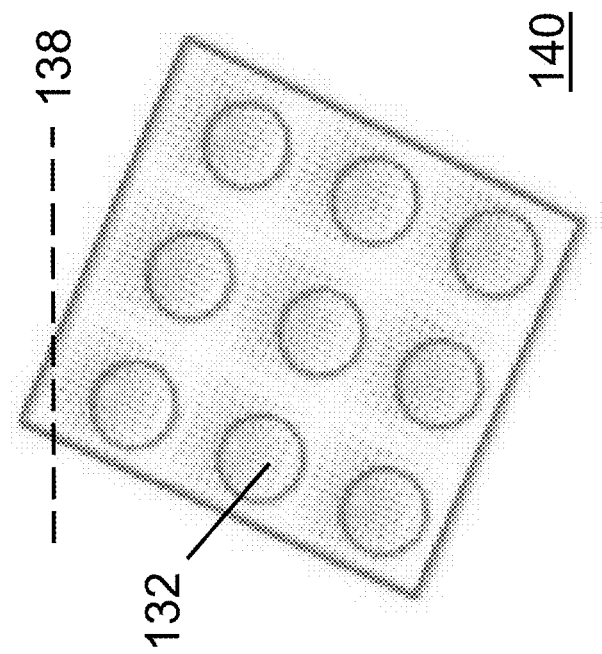
FIG. 32B illustrates another ultrasonic transducer according to the present disclosure where the transducer is tilted, such that long leakage pathways are not formed.
Figure 32A:
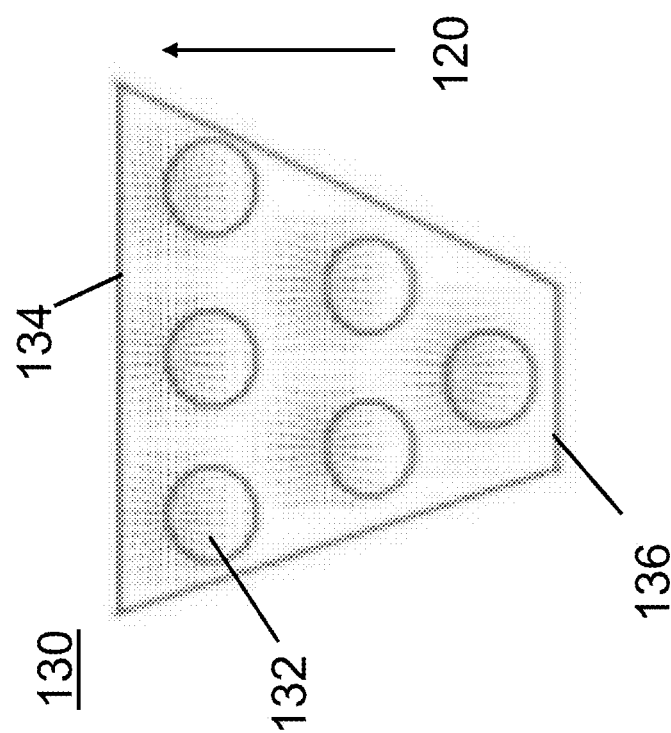
FIG. 32A illustrates an ultrasonic transducer of the present disclosure that has a crystal in the shape of an irregular polygon, such that long leakage pathways are not formed.

A solution to the leakage pathways is to orient the transducer so that the trapping lines produced with a multi-dimensional acoustic standing wave minimize the cross-sectional area for straight vertical channels between the trapping lines. This solution is ideally achieved by placing the trapping lines such that no two trapping lines are located vertically above each other. Two potential configurations are illustrated in FIG. 32A and FIG. 32B. In FIG. 32A, the transducer 130 has an irregular perimeter with four sides, i.e. is an irregular polygon. This transducer can be operated in a mode that generates six sets of trapping lines 132, with sides 134, 136 indicating a horizontal plane. Fluid flow is indicated by vertical arrow 120, which is normal to the horizontal plane. As can be seen here, there is very little vertical cross-sectional area for a straight vertical channel. Similarly, in FIG. 32B, dashed line 138 indicates a horizontal plane, and there is very little vertical cross-sectional area for a straight vertical channel. Here, the transducer is a square transducer 140 with nine trapping lines 132 as depicted in FIG. 14A, but tilted. The fluid flow in the active transducer configurations shown in FIG. 32A and FIG. 32B are circuitous, which reduces the upward fluid drag force, permitting particle clusters to eventually drop out based on increasing size. It is possible to control the drive signal provided to the transducers illustrated in FIGS. 31, 32A and 32B so that the clusters reach a certain size and are spaced from each other. Controlling the drive signal to the transducer can cause the clusters to not drop out, as discussed above with regard to FIG. 30. The configurations discussed herein can contribute the physical filtering of the fluid mixture processed in the acoustic chamber by determining the size and shape of channels between clusters (which includes channels between nodal trapping lines), which can be configured to block particles, especially particles of a certain size or shape.

Figure 33:
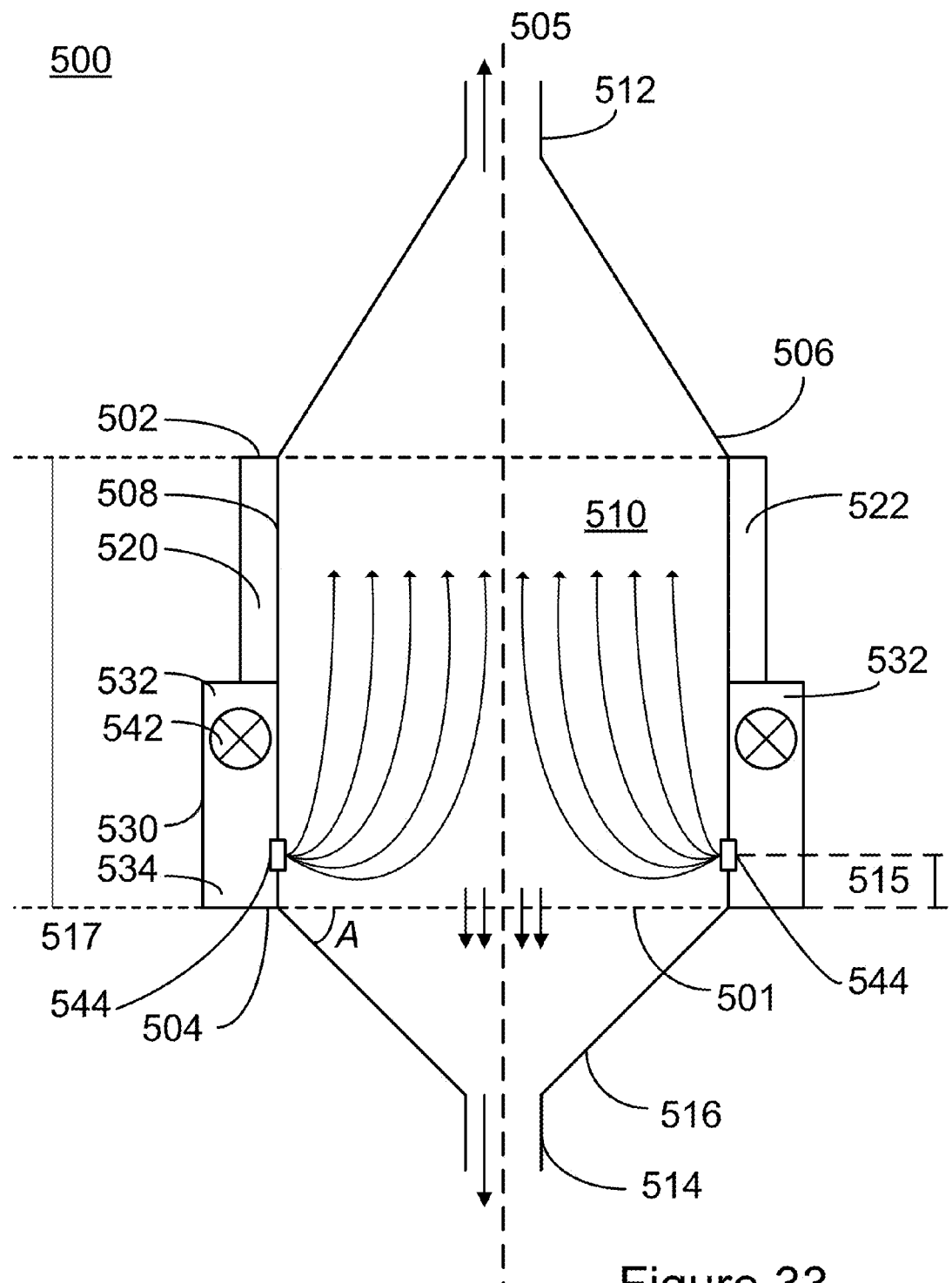
FIG. 33 is a cross-sectional diagram of an acoustophoretic device including two dump diffusers used to make the inflow more uniform.

FIG. 33 is a cross-sectional diagram of a configuration for an acoustophoretic device in which the methods of the present disclosure can be used. This device includes dump diffusers at the inlet(s) that create a more uniform flow through the device. The device 500 has a vertical orientation, with an upper end 502 and a lower end 504. The device also has two dump inlets and a collector design which provides a vertical plane or line of symmetry 505. Generally, the cross-section of the device in the flow direction is circular or rectangular. The device is formed from a housing 506 having a sidewall 508 that defines an acoustic chamber 510 therein. The acoustic chamber is empty, i.e. there is nothing within the chamber, and fluid flows through the acoustic chamber. At least one upper outlet 512 is present at the upper end of the acoustic chamber 510. At least one lower outlet 514 is present at the lower end 504 of the acoustic chamber. A shallow wall 516 is present at the lower end of the acoustic chamber, and leads to the outlet 514. The shallow wall has a shallow angle when measured relative to a horizontal plane (denoted here by the chamber bottom, line 501), with the angle A being in embodiments about 60° or less, including about 30° to about 45°. At least one ultrasonic transducer 520 is present on the sidewall 508, and at least one reflector 522 is present on the sidewall 508 opposite the ultrasonic transducer 520. The transducer 520 and the reflector 522 are located closer to the upper end 502 of the device.

This device 500 also includes a symmetrical, dual dump diffuser, plenum inlet configuration. Here, two dump diffusers 530 are placed on opposite sides of the device. Each dump diffuser has an upper end 532 and a lower end 534. An inlet 542 is located at the upper end 532, and at least one diffuser outlet 544 is located at the lower end. These diffuser outlets 544 also pass through the sidewall 508, and can be considered as diffuser inlets into the acoustic chamber. The diffuser outlet(s) can be in the form of a slot or a line of holes, and they are placed above the bottom of the acoustic chamber. In embodiments, the diffuser outlets are located above the chamber bottom 501 at a height 515 that is between 5% and 100% of the height 517 of the acoustic chamber, and more particularly between 5% and 25% of the height of the acoustic chamber. The diffuser outlets 544 provide a flow direction parallel to the axial direction of the acoustic standing waves generated by the ultrasonic transducer. The diffuser outlets are also arranged so that they are in opposing locations, so that the horizontal velocity will decrease to zero in the center of the acoustic chamber.

Each dump diffuser includes an entrance port 542 into which the mixture of host fluid/second fluid or particulate flows (the X refers to the flow direction into the paper). This eliminates downward flow in the acoustic chamber. The mixture fills up the chamber in the dump diffuser and then flows horizontally out of the diffuser outlet(s) 544 and enters the acoustic chamber, where the mixture flows vertically upwards and out of the upper outlet 512. The dump diffuser reduces/eliminates flow pulsations and flow non-uniformities that result from a horizontal inlet flow where gravity effects dominate. The diffuser outlets 544 then bring the heavier mixture into the acoustic chamber above the bottom of the chamber (line 501) and below the ultrasonic transducer and the nodal clusters that form in the ultrasonic standing waves. This minimizes any disturbances of the clusters set up by inflowing material.

The vertical plane or line of symmetry 505 is aligned with gravity forces. Also shown are flow streamlines which are desirably symmetrical, since this minimizes non-uniformities, eddy disturbances, circulation, and disturbance of clusters falling through outlet 514 to be collected. Symmetry also maximizes gravity forces in the inlet flow distribution and particle collection process. Because it is heavier than the permeate exiting at the top of the device, the (relatively) heavy incoming mixture comes in near the bottom of the acoustic chamber. The symmetrical inlets also assure that the incoming mixture spreads out across the bottom of the chamber due to gravity forces, and provides near uniform velocity profiles from bottom to top. The horizontal velocity of the mixture will decrease to zero as it approaches the center of the acoustic chamber due to the dual opposing inlet flows. A uniform velocity contributes to improved separation and collection results because the lateral acoustic forces overcome particle drag for the clusters to grow and continuously drop out of the acoustic chamber. A uniform velocity can also permit the elimination of an inlet flow distributor.

As the particle clusters drop out, the axial acoustic forces associated with the standing wave keeps the clusters intact. This phenomena assures rapid dropping of the clusters with high terminal velocities, on the order of 1 cm/sec. This speed is extremely fast compared to the chamber flow velocities, which are on the order of 0.1 cm/sec to 0.3 cm/sec. The shallow wall angle means the cylindrical particle clusters drop a short distance before they exit the acoustic chamber, so that little dispersion of the clusters occurs. Ideally, the system operates with 3 to 12 trapping lines per square inch of transducer. The symmetry, minimum flow disturbance in the central collection region, and shallow collector walls provide good collection results and can contribute to reduced use of baffles/laminar plates.

Figure 34:
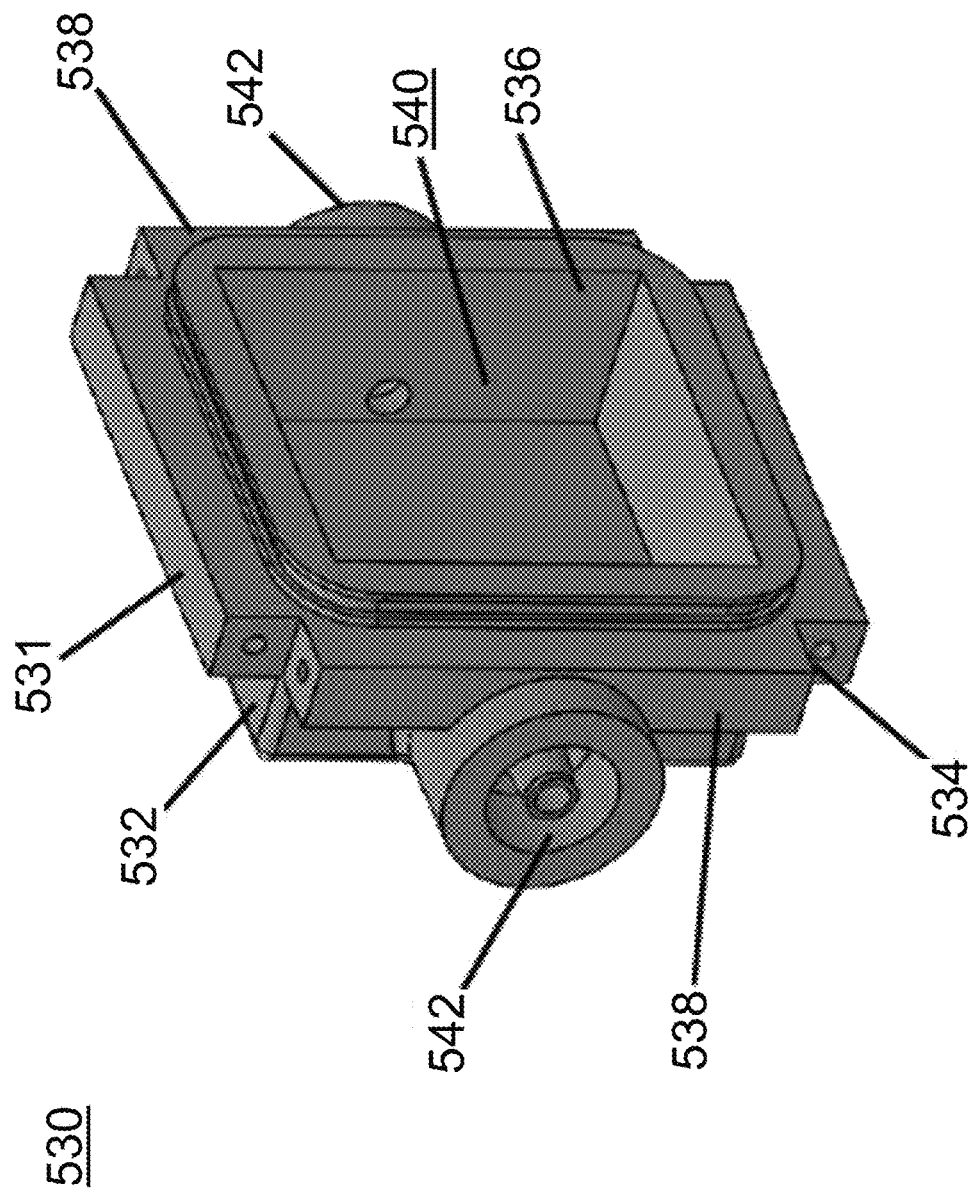
FIG. 34 is a perspective view of an example dump diffuser.
Figure 35:
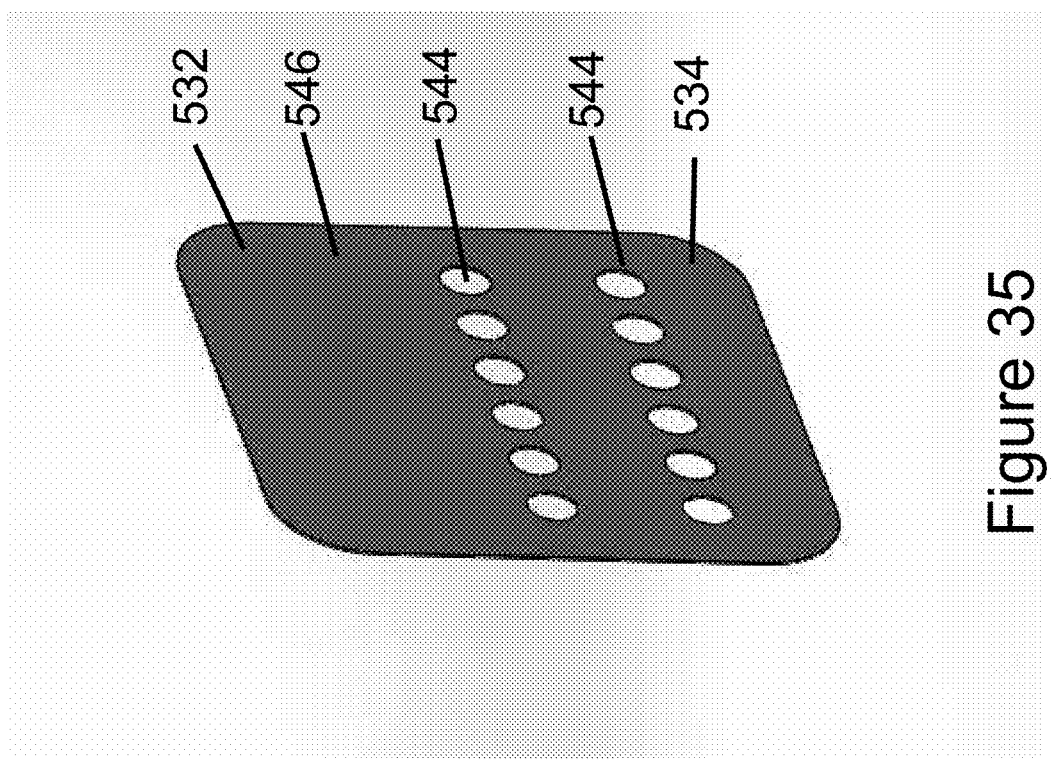
FIG. 35 is a perspective view of a plate with openings that is usable with the example dump diffuser of FIG. 34.

FIG. 34 and FIG. 35 provide additional detail on the dump diffusers that are used for providing a more uniform flow of the mixture of host fluid and particulate into the acoustic chamber 510. FIG. 34 is a perspective view with the front plate removed, showing both the interior and the exterior of a dump diffuser. FIG. 35 is a perspective view of the front plate of the dump diffuser. Starting with FIG. 34, the dump diffuser 530 includes a housing 531 having an upper end 532, an opposite lower end 534, two side faces 538, and a front face 536. A hollow chamber 540 is present within the housing 531. The dump diffuser also includes an entrance port 542 that receives the mixture and leads into the chamber 540. The entrance port 542 is present on the upper end and on a side face 538 of the housing; two entrance ports are visible here. FIG. 35 is a picture of the front plate 546 which is attached to the front face 536 of the housing. As illustrated here, the outlet 544 is located on the lower end 534 and is in the form of two lines of holes, though these could also be in the form of a thin slot. In use, the mixture of host fluid/second fluid or particulate enters through entrance ports 542 and fills up the chamber 540. Pressure then pushes the mixture uniformly out through outlets 544. The upper end of the front plate is solid, and has no holes or slots.

One specific application for the acoustophoresis devices and methods disclosed herein is in the processing of bioreactor materials. It is important to be able to filter all of the cells and cell debris from the expressed materials that are in the fluid stream. The expressed materials are composed of biomolecules such as recombinant proteins or monoclonal antibodies, and are the desired product to be recovered. Through the use of acoustophoresis, the separation of the cells and cell debris is very efficient and leads to very little loss of the expressed materials. This result is an improvement over current filtration processes (depth filtration, tangential flow filtration, and the like), which show limited efficiencies at high cell densities, so that the loss of the expressed materials in the filter beds themselves can be up to 5% of the materials produced by the bioreactor. The use of mammalian cell cultures including Chinese hamster ovary (CHO), NS0 hybridoma cells, baby hamster kidney (BHK) cells, and human cells has proven to be a very efficacious way of producing/expressing the recombinant proteins and monoclonal antibodies used in pharmaceuticals. The filtration of the mammalian cells and the mammalian cell debris through acoustophoresis aids in greatly increasing the yield of the bioreactor.

Another application for the acoustophoresis devices and methods discussed herein is directed to generating and collecting cells and/or cell vesicles, including oncosomes and exosomes, that can subsequently be used for therapeutic processes, including cell therapies. The biological cells or cell vesicles to be used in the cell therapy are cultured in a bioreactor and expanded (i.e. to increase the number of cells or cell vesicles in the bioreactor through cell reproduction). The cells may be lymphocytes such as T cells (e.g., regulatory T-cells (Tregs), Jurkat T-cells), B cells, or NK cells; their precursors, such as peripheral blood mononuclear cells (PBMCs); and the like. The cell vesicles may be derived from these or other cells. The cell culture media (aka host fluid), containing cells and/or cell vesicles, is filtered with a filtering device that produces an acoustic standing wave. In some examples, a portion of the cells and/or cell vesicles (product) is separated from the cell culture media using an acoustic standing wave. In some examples, the product is trapped and held in the acoustic standing wave, or are deflected from a fluid flow of the cell culture media. The remaining host fluid and other product in the remaining host fluid may be returned to the bioreactor. As the quantity of trapped product increases, larger clusters are formed that fall out of the acoustic standing wave at a critical size due to gravity forces. The clusters can fall into a product outlet outside a region of the acoustic standing wave, such as below the acoustic standing wave, from which the product can be recovered for use in cell therapy. In some examples, only a small portion of the product is trapped and removed from the bioreactor via the product outlet, and the remainder product continues to reproduce in the bioreactor, allowing for continuous production and recovery of the desired product.

In another application, acoustic standing waves are used to trap and hold biological cells and to separate the cells, including viruses (e.g. lentiviruses) or cell vesicles that are produced by the biological cells (collectively, product). In these embodiments, the product may be recovered for further processing for therapeutic purposes, or may be returned to the bioreactor post-separation to continue production.

In these applications, the acoustic devices and their operation according to the present disclosure can act as a product retention device. The acoustic product retention systems described herein operate over a range of product recirculation rates, and can efficiently retain product over a range of perfusion (or media removal) rates, or separate product from host media, and can be tuned to fully retain or selectively pass some percentage of cells through fluid flow rate, transducer power, frequency manipulation or other control parameters. Power, flow rates, frequency and other control parameters or sensed parameters can be monitored and used as feedback in an automated control system.

The product of interest may also be held in the flow chamber of the acoustic wave system through the use of an acoustic standing wave such that other moieties may be introduced in close proximity to and for the purpose of changing the target product. Such an operation would include the trapping of T cells and the subsequent introduction of modified lentivirus materials with a specific gene splice such that the lentivirus with a specific gene splice enters the T cell through transduction and generate a chimeric antigen receptor T cell also known as a CAR-T cell. Other genetic materials or vehicles may be used and introduced into the acoustic standing wave to permit transfection of T cells.

The acoustophoresis process, through the use of multidimensional acoustic waves, may also be coupled with a standard filtration process upstream or downstream, such as depth filtration using diatomaceous earth, tangential flow filtration (TFF), or other physical filtration processes.

It is contemplated that the acoustophoretic devices of the present disclosure can be used in a filter "train," in which multiple different filtration steps are used to clarify or purify an initial fluid/particle mixture to obtain the desired product and manage different materials from each filtration step. Each filtration step can be optimized to remove a particular material, improving the overall efficiency of the clarification process. An individual acoustophoretic device can operate as one or multiple filtration steps. For example, each individual ultrasonic transducer within a particular acoustophoretic device can to operated to trap materials within a given particle range. It is particularly contemplated that the acoustophoretic device can be used to remove large quantities of material, reducing the burden on subsequent downstream filtration steps/stages. However, it is contemplated that additional filtration steps/stages can be placed upstream or downstream of the acoustophoretic device. Of course, multiple acoustophoretic devices can be used as well. It is particularly contemplated that desirable biomolecules or cells can be recovered/separated after such filtration/purification.

The outlets of the acoustophoretic devices of the present disclosure (e.g. clarified fluid and concentrated cells) can be fluidly connected to any other filtration step or filtration stage. Such filtration steps can include various methods such as depth filtration, sterile filtration, size exclusion filtration, or tangential filtration. Depth filtration uses physical porous filtration mediums that can retain material through the entire depth of the filter. In sterile filtration, membrane filters with extremely small pore sizes are used to remove microorganisms and viruses, generally without heat or irradiation or exposure to chemicals. Size exclusion filtration separates materials by size and/or molecular weight using physical filters with pores of given size. In tangential filtration, the majority of fluid flow is across the surface of the filter, rather than into the filter.

Chromatography can also be used, including cationic chromatography columns, anionic chromatography columns, affinity chromatography columns, mixed bed chromatography columns. Other hydrophilic/hydrophobic processes can also be used for filtration purposes.

Desirably, flow rates through the devices of the present disclosure can be a minimum of 4.65 mL/min per $cm^2$ of cross-sectional area of the acoustic chamber. Even more desirably, the flow rate can be as high as 25 $mL/min/cm^2$, and can range as high as 40 $mL/min/cm^2$ to 270 $mL/min/cm^2$, or even higher. This is true for batch reactors, fed-batch bioreactors and perfusion bioreactors.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner.

The present disclosure has been described with reference to exemplary embodiments. Modifications and alterations may occur to others upon reading and understanding the preceding detailed description. It is intended that the present disclosure be construed as including all such modifications and alterations insofar as they come within the scope of the appended claims or the equivalents thereof.

The invention claimed is:

1. A method of generating particulate clusters, the method comprising:
    flowing a mixture of a host fluid and particulate through an acoustophoretic device, the device comprising:
        a housing that defines an acoustic chamber;
        at least one outlet from the acoustic chamber;
        at least one inlet to the acoustic chamber; and
        at least one ultrasonic transducer coupled to the acoustic chamber and at least one reflector coupled to the acoustic chamber opposite the at least one ultrasonic transducer, the at least one ultrasonic transducer including a piezoelectric material; and
    driving the at least one ultrasonic transducer to create a multi-dimensional acoustic standing wave in the acoustic chamber to generate at least a first particulate cluster and a second particulate cluster that are separated by a fluid channel running therebetween; and
    selectively driving the at least one ultrasonic transducer so as to selectively control either (a) a dimension of each particulate cluster, or (b) a dimension of the fluid channel.

2. The method of claim 1, further comprising driving the at least one ultrasonic transducer with a voltage signal, wherein the frequency of the voltage signal is selectively tuned such that a height of each of the first and second particulate clusters is from about 150 micrometers to about 1200 micrometers.

3. The method of claim 1, further comprising driving the at least one ultrasonic transducer with a voltage signal, wherein the frequency of the voltage signal is selectively tuned such that the fluid channel has a height of from about 50 micrometers to about 500 micrometers.

4. The method of claim 1, further comprising driving the at least one ultrasonic transducer with a voltage signal, wherein the frequency of the voltage signal is selectively tuned such that a ratio of the height of the first and second particulate clusters to the height of the fluid channel is from about 1:1 to about 5:1.

5. The method of claim 1, further comprising driving the at least one ultrasonic transducer with a voltage signal, wherein the frequency of the voltage signal is selectively tuned such that:
    the first and second particulate clusters are each about 150 micrometers to about 1200 micrometers in height; and
    the fluid channel has a height of from about 50 micrometers to about 500 micrometers; and
    a ratio of the height of the first and second particulate clusters to the height of the fluid channel is from about 1:1 to about 5:1.

6. The method of claim 1, further comprising driving the at least one ultrasonic transducer with a voltage signal, wherein the frequency of the voltage signal is selectively tuned such that:
    the first and second particulate clusters are each about 200 micrometers to about 600 micrometers in height; and
    the fluid channel has a height of from about 100 micrometers to about 250 micrometers; and
    a ratio of the height of the first and second particulate clusters to the height of the fluid channel is from about 1:1 to about 5:1.

7. The method of claim 1, wherein the particulates are selected from the group consisting of Chinese hamster ovary (CHO) cells, NS0 hybridoma cells, baby hamster kidney (BHK) cells, human cells, T cells, B cells, NK cells, algae, bacteria, viruses, or microcarriers.

8. The method of claim 1, wherein the acoustophoretic device is part of a filter train.

9. The method of claim 1, further comprising collecting the particulate clusters and sending the particulate clusters through at least one additional downstream filtration stage.

10. The method of claim 1, further comprising separating the particulate clusters from the host fluid to obtain a clarified host fluid, and sending the clarified host fluid through at least one additional downstream filtration stage.

11. A method of controlling particulate clusters, the method comprising:
    providing a mixture of a host fluid and particulate to an acoustophoretic device, the device comprising:
        an acoustic chamber; and
        at least one ultrasonic transducer coupled to the acoustic chamber and at least one reflector coupled to the acoustic chamber opposite the at least one ultrasonic transducer, the at least one ultrasonic transducer including a piezoelectric material;
    driving the at least one ultrasonic transducer to generate a multi-dimensional acoustic standing wave in the acoustic chamber to generate at least a first particulate cluster in a first nodal trapping line and a second particulate cluster in a second nodal trapping line that are spaced from each other in a direction of gravity; and
    selectively driving the at least one ultrasonic transducer such that one of the first particulate cluster or the second particulate cluster bleeds material into the other of the first particulate cluster or the second particulate cluster.

12. A method of controlling particulate clusters, the method comprising:
    providing a mixture of a host fluid and particulate to an acoustophoretic device, the device comprising:
        an acoustic chamber; and
        at least one ultrasonic transducer coupled to the acoustic chamber and at least one reflector coupled to the acoustic chamber opposite the at least one ultrasonic transducer, the at least one ultrasonic transducer including a piezoelectric material;
    driving the at least one ultrasonic transducer to generate a multi-dimensional acoustic standing wave in the acoustic chamber to generate at least a first particulate cluster and a second particulate cluster that are separated by a fluid channel running therebetween; and
    selectively driving the at least one ultrasonic transducer such that the first particulate cluster and the second particulate cluster are maintained in and do not leave the multi-dimensional acoustic standing wave.

* * * * *